(12) United States Patent
Hlavinka et al.

(10) Patent No.: US 8,987,394 B2
(45) Date of Patent: Mar. 24, 2015

(54) CATALYST COMPOSITIONS FOR THE POLYMERIZATION OF OLEFINS

(71) Applicant: Chevron Phillips Chemical Company LP, The Woodlands, TX (US)

(72) Inventors: Mark L. Hlavinka, Bartlesville, OK (US); Qing Yang, Bartlesville, OK (US); Youlu Yu, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/306,449

(22) Filed: Jun. 17, 2014

(65) Prior Publication Data

US 2014/0296453 A1 Oct. 2, 2014

Related U.S. Application Data

(63) Continuation of application No. 13/338,320, filed on Dec. 28, 2011, now Pat. No. 8,785,576.

(51) Int. Cl.

| | | |
|---|---|---|
| *C08F 4/76* | (2006.01) | |
| *C08F 4/64* | (2006.01) | |
| *C08F 4/52* | (2006.01) | |
| *B01J 31/22* | (2006.01) | |
| *C07F 7/00* | (2006.01) | |
| *C07F 7/28* | (2006.01) | |
| *C08F 2/01* | (2006.01) | |
| *C08F 4/02* | (2006.01) | |
| *C08F 4/16* | (2006.01) | |
| *C08F 110/02* | (2006.01) | |
| *C08F 4/659* | (2006.01) | |

(52) U.S. Cl.
CPC ............... *C08F 4/76* (2013.01); *B01J 31/2243* (2013.01); *C07F 7/003* (2013.01); *C07F 7/006* (2013.01); *C07F 7/28* (2013.01); *C08F 2/01* (2013.01); *C08F 4/025* (2013.01); *C08F 4/16* (2013.01); *C08F 4/52* (2013.01); *C08F 4/64158* (2013.01); *C08F 4/659* (2013.01); *C08F 110/02* (2013.01); *C08F 2500/03* (2013.01)
USPC ........... 526/161; 526/172; 526/170; 526/160; 526/127; 526/129; 526/130; 526/137; 526/348

(58) Field of Classification Search
USPC .................................................. 526/161, 172
See application file for complete search history.

(56) References Cited

U.S. PATENT DOCUMENTS

| | | |
|---|---|---|
| 3,242,099 A | 3/1966 | Manyik et al. |
| 3,248,179 A | 4/1966 | Norwood |

(Continued)

FOREIGN PATENT DOCUMENTS

| | | |
|---|---|---|
| WO | WO 2001/18010 | 3/2001 |
| WO | WO 2007/118008 | 10/2007 |

OTHER PUBLICATIONS

Tshuva et al. Organometallics, 2002, 21, 662-670.*

(Continued)

*Primary Examiner* — Rip A. Lee
(74) *Attorney, Agent, or Firm* — Merchant & Gould

(57) ABSTRACT

Catalyst compositions containing N,N-bis[2-hydroxidebenzyl]amine transition metal compounds are disclosed. Methods for making these transition metal compounds and for using such compounds in catalyst compositions for the polymerization of olefins also are provided.

20 Claims, 7 Drawing Sheets

TM-1

TM-2

TM-3

(56) References Cited

U.S. PATENT DOCUMENTS

| | | | |
|---|---|---|---|
| 4,060,480 | A | 11/1977 | Reed et al. |
| 4,452,910 | A | 6/1984 | Hopkins et al. |
| 4,501,885 | A | 2/1985 | Sherk et al. |
| 4,588,790 | A | 5/1986 | Jenkins, III et al. |
| 4,794,096 | A | 12/1988 | Ewen |
| 4,808,561 | A | 2/1989 | Welborn, Jr. |
| 5,352,749 | A | 10/1994 | DeChellis et al. |
| 5,376,611 | A | 12/1994 | Shveima |
| 5,436,304 | A | 7/1995 | Griffin et al. |
| 5,455,314 | A | 10/1995 | Burns et al. |
| 5,565,175 | A | 10/1996 | Hottovy et al. |
| 5,575,979 | A | 11/1996 | Hanson |
| 5,576,259 | A | 11/1996 | Hasegawa et al. |
| 5,739,220 | A | 4/1998 | Shamshoum et al. |
| 5,807,938 | A | 9/1998 | Kaneko et al. |
| 5,919,983 | A | 7/1999 | Rosen et al. |
| 6,015,779 | A | 1/2000 | Eaton et al. |
| 6,107,230 | A | 8/2000 | McDaniel et al. |
| 6,165,929 | A | 12/2000 | McDaniel et al. |
| 6,239,235 | B1 | 5/2001 | Hottovy et al. |
| 6,262,191 | B1 | 7/2001 | Hottovy et al. |
| 6,294,494 | B1 | 9/2001 | McDaniel et al. |
| 6,300,271 | B1 | 10/2001 | McDaniel et al. |
| 6,316,553 | B1 | 11/2001 | McDaniel et al. |
| 6,333,423 | B1 | 12/2001 | Kol et al. |
| 6,355,594 | B1 | 3/2002 | McDaniel et al. |
| 6,376,415 | B1 | 4/2002 | McDaniel et al. |
| 6,388,017 | B1 | 5/2002 | McDaniel et al. |
| 6,391,816 | B1 | 5/2002 | McDaniel et al. |
| 6,395,666 | B1 | 5/2002 | McDaniel et al. |
| 6,524,987 | B1 | 2/2003 | Collins et al. |
| 6,548,441 | B1 | 4/2003 | McDaniel et al. |
| 6,548,442 | B1 | 4/2003 | McDaniel et al. |
| 6,576,583 | B1 | 6/2003 | McDaniel et al. |
| 6,596,827 | B2 * | 7/2003 | Kol et al. .................. 526/161 |
| 6,613,712 | B1 | 9/2003 | McDaniel et al. |
| 6,632,894 | B1 | 10/2003 | McDaniel et al. |
| 6,667,274 | B1 | 12/2003 | Hawley et al. |
| 6,730,750 | B2 | 5/2004 | Eaton et al. |
| 6,750,302 | B1 | 6/2004 | McDaniel et al. |
| 6,833,415 | B2 | 12/2004 | Kendrick et al. |
| 7,247,594 | B2 | 7/2007 | Jayaratne et al. |
| 7,884,163 | B2 | 2/2011 | McDaniel et al. |
| 8,785,576 | B2 | 7/2014 | Hlavinka et al. |
| 8,791,217 | B2 | 7/2014 | Hlavinka et al. |
| 2004/0059070 | A1 | 3/2004 | Whitte et al. |
| 2007/0111883 | A1 | 5/2007 | Jayaratne et al. |
| 2013/0172497 | A1 | 7/2013 | Hlavinka et al. |
| 2013/0172498 | A1 | 7/2013 | Hlavinka et al. |

OTHER PUBLICATIONS

Tshuva et al. Chem. Commun. 2000, 379-380.*
Barroso et al. Eur. J. lnorg. Chem., 2011, 4277-4290.*
Gurubasavaraj et al. Organometallics, 2010, 29, 3500-3506.*
T.J. Pinnavaia, Science 220 (4595), pp. 365-371 (1983).
J.M. Thomas, Intercalation Chemistry, (S. Whittington and A. Jacobson, eds.) Ch. 3, pp. 55-99, Academic Press, Inc., (1972).
J. Am. Chem. Soc., 2005, 127, pp. 14756-14768.
Modern Plastics Encyclopedia, Mid-Nov. 1995 Issue, vol. 72, No. 12, 3 pages.
Film Extrusion Manual—Process, Materials, Properties, TAPPI Press, 1992, 13 pages.
Sokolowski, et al., entitled "Phenoxyl Radical Complexes of Zinc(II)" J. Am. Chem. Soc. 1997, 119, pp. 8889-8900.
Tshuva, et al. entitled "[ONXO]-Type Amine Bis(phenolate) Zirconium and Hafnium Complexes as Extremely Active 1-Hexene Polymerization Catalysts," Organometallics 2002, 21, pp. 662-670.
Tshuva, et al., entitled "Zirconium Complexes of Amine-Bis(phenolate) Ligands as Catalysts for 1-Hexene Polymerization: Peripheral Structural Parameters Strongly Affect Reactivity," Organometallics 2001, 20, pp. 3017-3028.
Tshuva, et al., entitled "Novel zirconium complexes of amine bis(phenolate) ligands. Remarkable reactivity in polymerization of hex-1-ene due to an extra donor arm," The Royal Society of Chemistry 2000, Chem Commun., 2000, pp. 379-380.
Gibson, et al, entitled "Advances in Non-Metallacene Olefin Polymerization Catalysis," Chem Rev. 2003, 103, pp. 283-315.
Hawley's Condensed Chemical Dictionary, 11th Ed., John Wiley & Sons, 1995, 3 pages.
Cotton et al., Advanced Inorganic Chemistry, 6th Ed., Wiley-Interscience, 1999, 4 pages.
International Search Report for Application No. PCT/US2012/0069358 dated Mar. 21, 2013, 4 pages.
International Search Report and Written Opinion for Application No. PCT/US2012/069388 dated Feb. 26, 2013, 12 pages.
Gurubasavaraj et al, entitled "Hetero-bimetallic Complexes of Titanatranes with Aluminum Alkyls: Synthesis, Structural Analysis, and Their Use in Catalysis for Ethylene Polymerization," Published in *Organometallics* 2010, vol. 29, pp. 3500-3506.
Groysman, et al., entitled "From THF to Furan: Activity Tuning and Mechanistic Insight via Sidearm Donor Replacement in Group IV Amine Bis(phenolate) Polymerization Catalysts," Published in *Organometallics* 2003, vol. 23, pp. 3013-3015.
Barroso, et al, entitled "Chiral Diamine Bis(phenolate) $Ti^{IV}$ and $Zr^{IV}$ Complexes—Synthesis, Structures and Reactivity," Published in *Eur. J. Inorg. Chem*, 2011, pp. 4277-4290.
U.S. Patent Application entitled "Catalyst Systems for Production of Alpha Olefin Oligomers and Polymers" having U.S. Appl. No. 14/307,517, filed on Jun. 18, 2014 (0072usc1).

\* cited by examiner

TM-1

TM-2

TM-3

TM-A

TM-B

TM-C

TM-D

CATALYST COMPOSITIONS FOR THE POLYMERIZATION OF OLEFINS

REFERENCE TO RELATED APPLICATION

This application is a continuation application of co-pending U.S. patent application Ser. No. 13/338,320, now U.S. Pat. No. 8,785,576, the disclosure of which is incorporated herein by reference in its entirety.

BACKGROUND OF THE INVENTION

Polyolefins such as high density polyethylene (HDPE) homopolymer and linear low density polyethylene (LLDPE) copolymer can be produced using various combinations of catalyst systems and polymerization processes. Examples of commercially viable catalyst systems include chromium-based, metallocene-based, and Ziegler-Natta based catalyst systems.

The present invention relates generally to the field of olefin polymerization catalysis, catalyst compositions, methods for the polymerization of olefins, and polyolefins. More specifically, this invention relates to amine bis(phenolate) transition metal compounds (e.g., N,N-bis[2-hydroxidebenzyl]amine transition metal compounds) and catalyst compositions employing such compounds.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention generally relates to new catalyst compositions, methods for preparing catalyst compositions, methods for using the catalyst compositions to polymerize olefins, the polymer resins produced using such catalyst compositions, and articles produced using these polymer resins. In particular, embodiments of the present invention are directed to amine bis(phenolate) or N,N-bis[2-hydroxidebenzyl]amine transition metal compounds, and catalyst compositions employing such transition metal compounds. Catalyst compositions of the present invention which contain these transition metal compounds can be used to produce, for example, ethylene-based homopolymers and copolymers.

In accordance with an embodiment of the present invention, disclosed and described herein are transition metal compounds having the formula:

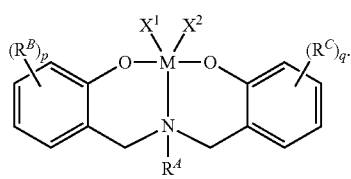

(Ia)

In formula (Ia), M can be Ti, Zr, or Hf, and $X^1$ and $X^2$ independently can be a monoanionic ligand. Each $R^B$ and $R^C$ independently can be a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group, wherein p and q independently can be 0, 1, 2, 3, or 4. $R^A$ in formula (Ia) can be a $C_1$ to $C_{36}$ hydrocarbyl group or a $C_1$ to $C_{36}$ halogenated hydrocarbyl group.

In accordance with another embodiment of the present invention, disclosed and described herein are transition metal compounds having the formula:

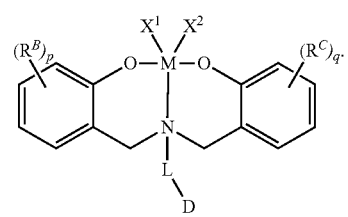

(IIa)

In formula (IIa), M can be Ti, Zr, or Hf, and $X^1$ and $X^2$ independently can be a monoanionic ligand. Each $R^B$ and $R^C$ independently can be a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group, wherein p and q independently are 0, 1, 2, 3, or 4. L in formula (IIa) can be a $C_1$ to $C_{18}$ hydrocarbylene group, while D can be a chemical group comprising at least one of nitrogen, oxygen, phosphorus, and sulfur.

In accordance with yet another embodiment of the present invention, disclosed and described herein are transition metal compounds having the formula:

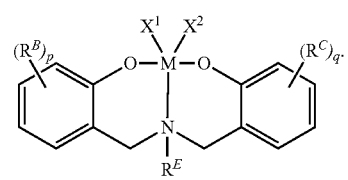

(IIIa)

In formula (IIIa), M can be Ti, Zr, or Hf, and $X^1$ and $X^2$ independently can be a monoanionic ligand. Each $R^B$ and $R^C$ independently can be a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group, wherein p and q independently can be 0, 1, 2, 3, or 4. $R^E$ in formula (IIIa) can be a $C_2$ to $C_{36}$ alkenyl group.

Catalyst compositions containing these transition metal complexes are also provided by the present invention. In one embodiment, a catalyst composition is disclosed which comprises an amine bis(phenolate) or N,N-bis[2-hydroxidebenzyl]amine transition metal complex and an activator-support. Optionally, this catalyst composition can further comprise a co-catalyst. In some aspects, the co-catalyst can comprise an organoaluminum compound, while in other aspects, the co-catalyst can comprise an aluminoxane compound, an organoboron or organoborate compound, an ionizing ionic compound, an organoaluminum compound, an organozinc compound, an organomagnesium compound, an organolithium compound, or combinations thereof. More than one co-catalyst can be present in catalyst compositions disclosed herein.

The present invention also contemplates and encompasses olefin polymerization processes. Such processes can comprise contacting a catalyst composition with an olefin monomer and optionally an olefin comonomer under polymerization conditions to produce an olefin polymer. Generally, the catalyst composition employed can comprise any of the transition metal compounds disclosed herein and any of the activator-supports and optional co-catalysts disclosed herein. For example, organoaluminum compounds can be utilized in the catalyst compositions and/or polymerization processes.

Polymers produced from the polymerization of olefins, resulting in homopolymers, copolymers, terpolymers, etc., can be used to produce various articles of manufacture.

DEFINITIONS

Figure 1:
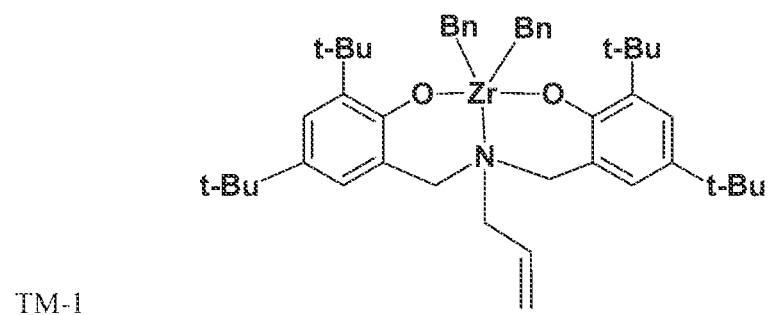
FIG. 1 presents the structures and abbreviations for compounds TM-1, TM-2, and TM-3 discussed herein.
Figure 1:
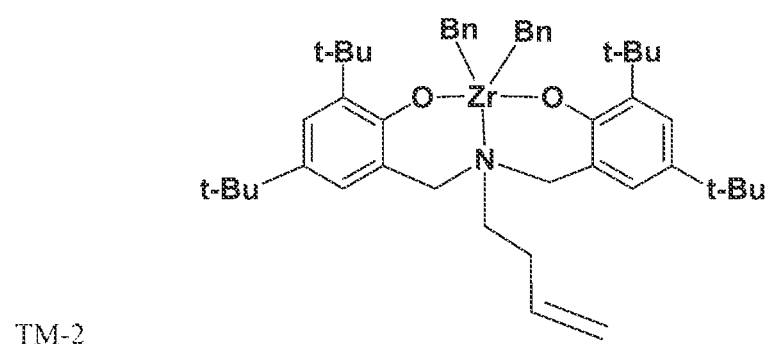
Figure 1:
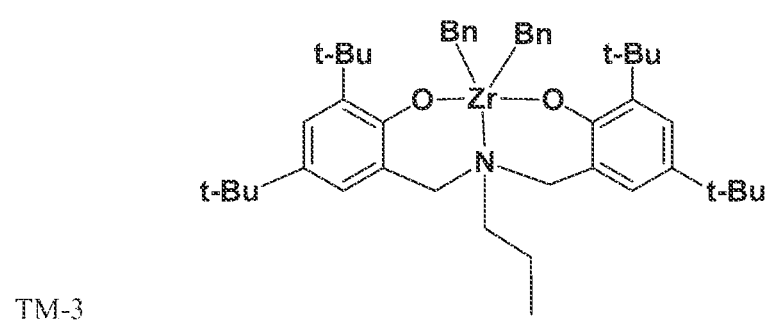

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of, apply only to feature class to which is utilized and it is possible to have different transitional terms or phrases utilized with different features within a claim. For example a method can comprise several recited steps (and other non-recited steps) but utilize a catalyst system preparation consisting of specific steps but utilize a catalyst system comprising recited components and other non-recited components. While compositions and methods are described in terms of "comprising" various components or steps, the compositions and methods can also "consist essentially of" or "consist of" the various components or steps, unless stated otherwise. For example, a catalyst composition consistent with embodiments of the present invention can comprise; alternatively, can consist essentially of; or alternatively, can consist of; (i) a transition metal compound, (ii) an activator-support, and (iii) optionally, a co-catalyst.

The terms "a," "an," "the," etc., are intended to include plural alternatives, e.g., at least one, unless otherwise specified. For instance, the disclosure of "an activator-support" or "a transition metal compound" is meant to encompass one, or mixtures or combinations of more than one, activator-support or transition metal compound, respectively, unless otherwise specified.

Groups of elements of the table are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogen atoms, as necessary for the situation, removed from the alkane. Throughout the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be aliphatic or aromatic, acyclic or cyclic groups, and/or linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane group, cycloalkyl, cycloalkylene, cycloalkane groups, aralkyl, aralkylene, and aralkane groups, respectively, among other groups as members.

An aliphatic compound is a class of acyclic or cyclic, saturated or unsaturated, carbon compounds, excluding aromatic compounds. An "aliphatic group" is a generalized group formed by removing one or more hydrogen atoms (as necessary for the particular group) from carbon atom of an aliphatic compound. That is, an aliphatic compound is a non-aromatic organic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, tertiary carbon atom, respectively, of an alkane. The n-alkyl group can be derived by removal of a hydrogen atom from a terminal carbon atom of a linear alkane. The groups $RCH_2$ ($R \neq H$), $R_2CH$ ($R \neq H$), and $R_3C$ ($R \neq H$) are primary, secondary, and tertiary alkyl groups, respectively.

A cycloalkane is a saturated cyclic hydrocarbon, with or without side chains, for example, cyclobutane. Other identifiers can be utilized to indicate the presence of particular groups in the cycloalkane (e.g. halogenated cycloalkane indicates that the presence of one or more halogen atoms replacing an equivalent number of hydrogen atoms in the cycloalkane). Unsaturated cyclic hydrocarbons having one endocyclic double or one triple bond are called cycloalkenes and cycloalkynes, respectively. Those having more than one such multiple bond are cycloalkadienes, cycloalkatrienes, and so forth. Other identifiers can be utilized to indicate the presence of particular groups in the cycloalkene, cycloalkadienes, cycloalkatrienes, and so forth.

A "cycloalkyl group" is a univalent group derived by removing a hydrogen atom from a ring carbon atom from a cycloalkane. For example, a 1-methylcyclopropyl group and a 2-methylcyclopropyl group are illustrated as follows.

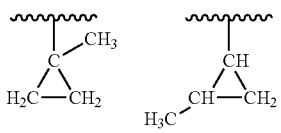

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. An "cycloalkane group" refers to a generalized group formed by removing one or more hydrogen atoms (as necessary for the particular group and at least one of which is a ring carbon) from a cycloalkane.

The term "alkene" whenever used in this specification and claims refers a linear or branched hydrocarbon olefin that has one carbon-carbon double bond and the general formula $C_nH_{2n}$. Alkadienes refer to a linear or branched hydrocarbon olefin having two carbon-carbon double bonds and the general formula $C_nH_{2n-2}$ and alkatrienes refer to linear or branched hydrocarbon olefins having three carbon-carbon and the general formula $C_nH_{2n-4}$. Alkenes, alkadienes, and alkatrienes can be further identified by the position of the carbon-carbon double bond(s). Other identifiers can be utilized to indicate the presence or absence of particular groups within an alkene, alkadiene, or alkatriene. For example, a haloalkene refers to an alkene having one or more hydrogen atoms replace with a halogen atom.

An "alkenyl group" is a univalent group derived from an alkene by removal of a hydrogen atom from any carbon atom of the alkene. Thus, "alkenyl group" includes groups in which the hydrogen atom is formally removed from an $sp^2$ hybridized (olefinic) carbon atom and groups in which the hydrogen atom is formally removed from any other carbon atom. For example and unless otherwise specified, 1-propenyl (—CH=CHCH$_3$), 2-propenyl [(CH$_3$)C=CH$_2$], and 3-propenyl (—CH$_2$CH=CH$_2$) groups are encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms.

An "alkene group" refers to a generalized group formed by removing one or more hydrogen atoms (as necessary for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond can both be specified. Other identifiers can be utilized to indicate the presence or absence of particular groups within an alkene group. Alkene groups can also be further identified by the position of the carbon-carbon double bond.

The term "alkyne" whenever used in this specification and claims refers to a linear or branched hydrocarbon olefin that has one carbon-carbon triple bond and the general formula $C_nH_{2n-2}$. Alkadiynes refer to a hydrocarbon olefin having two carbon-carbon double bonds and the general formula $C_nH_{2n-6}$ and alkatriynes refer to hydrocarbon olefins having three carbon-carbon and the general formula $C_nH_{2n-10}$. Alkynes, alkadiynes, and alkatriynes can be further identified by the position of the carbon-carbon triple bond(s). Other identifiers can be utilized to indicate the presence or absence of particular groups within an alkene, alkadiene, or alkatriene. For example, a haloalkyne refers to an alkyne having one or more hydrogen atoms replace with a halogen atom.

An "alkynyl group" is a univalent group derived from an alkyne by removal of a hydrogen atom from any carbon atom of the alkyne. Thus, "alkynyl group" includes groups in which the hydrogen atom is formally removed from an sp hybridized (acetylenic) carbon atom and groups in which the hydrogen atom is formally removed from any other carbon atom. For example and unless otherwise specified, 1-propynyl (—C≡CCH$_3$) and 3-propynyl (HC≡CCH$_2$—) groups are all encompassed with the term "alkynyl group." Similarly, an "alkynylene group" refers to a group formed by formally removing two hydrogen atoms from an alkyne, either two hydrogen atoms from one carbon atom if possible or one hydrogen atom from two different carbon atoms. An "alkyne group" refers to a generalized group formed by removing one or more hydrogen atoms (as necessary for the particular group) from an alkyne. Other identifiers can be utilized to indicate the presence or absence of particular groups within an alkyne group. Alkyne groups can also be further identified by the position of the carbon-carbon triple bond.

The term "olefin" whenever used in this specification and claims refers to compound that has at least one carbon-carbon double bond that is not part of an aromatic ring or ring system. The term "olefin" includes aliphatic, aromatic, cyclic or acyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins can also be further identified by the position of the carbon-carbon double bond. It is noted that alkenes, alkadienes, alkatrienes, cycloalkenes, cycloalkadienes, are members of the class of olefins. The olefin can be further identified by the position of the carbon-carbon double bond(s).

The term "alpha olefin" as used in this specification and claims refers to an olefin that has a double bond between the first and second carbon atom of a contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

A "heterocyclic compound" is a cyclic compound having at least two different elements as ring member atoms. For example, heterocyclic compounds can comprise rings containing carbon and nitrogen (for example, tetrahydropyrrole), carbon and oxygen (for example, tetrahydrofuran), or carbon and sulfur (for example, tetrahydrothiophene), among others. Heterocyclic compounds and heterocyclic groups can be either aliphatic or aromatic.

A "heterocyclyl group" is a univalent group formed by removing a hydrogen atom from a heterocyclic ring or ring system carbon atom of a heterocyclic compound. By specifying that the hydrogen atom is removed from a heterocyclic ring or ring system carbon atom, a "heterocyclyl group" is distinguished from a "cycloheteryl group," in which a hydrogen atom is removed from a heterocyclic ring or ring system heteroatom. For example, a pyrrolidin-2-yl group illustrated below is one example of a "heterocyclyl group," and a pyrrolidin-1-yl group illustrated below is one example of a "cycloheteryl" group."

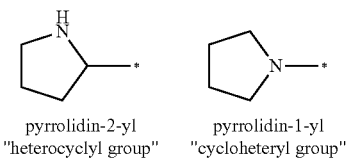

pyrrolidin-2-yl          pyrrolidin-1-yl
"heterocyclyl group"    "cycloheteryl group"

Similarly, a "heterocyclylene group" or more simply, a "heterocyclene group," refers to a group formed by removing two hydrogen atoms from a heterocyclic compound, at least one of which is from a heterocyclic ring or ring system carbon. Thus, in a "heterocyclylene group," at least one hydrogen is removed from a heterocyclic ring or ring system carbon atom, and the other hydrogen atom can be removed from any other carbon atom, including for example, the same heterocyclic ring or ring system carbon atom, a different heterocyclic ring or ring system ring carbon atom, or a non-ring carbon atom. A "heterocyclic group" refers to a generalized group formed by removing one or more hydrogen atoms (as necessary for the particular group and at least one of which is a heterocyclic ring carbon atom) from a heterocyclic compound. Generally, a heterocyclic compound can be aliphatic or aromatic unless otherwise specified.

A "cycloheteryl group" is a univalent group formed by removing a hydrogen atom from a heterocyclic ring or ring system heteroatom of a heterocyclic compound, as illustrated. By specifying that the hydrogen atom is removed from a heterocyclic ring or ring system heteroatom and not from a ring carbon atom, a "cycloheteryl group" is distinguished from a "heterocyclyl group" in which a hydrogen atom is removed from a heterocyclic ring or ring system carbon atom. Similarly, a "cycloheterylene group" refers to a group formed by removing two hydrogen atoms from an heterocyclic compound, at least one of which is removed from a heterocyclic ring or ring system heteroatom of the heterocyclic compound; the other hydrogen atom can be removed from any other atom, including for example, a heterocyclic ring or ring system ring carbon atom, another heterocyclic ring or ring system heteroatom, or a non-ring atom (carbon or heteroatom). A "cyclohetero group" refers to a generalized group formed by removing one or more hydrogen atoms (as necessary for the particular group and at least one of which is from a heterocyclic ring or ring system heteroatom) from a heterocyclic compound.

An arene is aromatic hydrocarbon, with or without side chains (e.g. benzene, toluene, or xylene, among others. An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

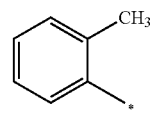

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g. the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g. the 2 carbon atom in the phenyl group of 6-phenylbenzofuran and a heteroarene group if the removed hydrogen carbon came from a heteroaromatic ring or ring system carbon atom (e.g. the 2 or 7 carbon atom of the benzofuran group or 6-phenylbenzofuran). It should be noted that according the definitions provided herein, general arene groups (including an aryl group and an areylene group) include those having zero, one, or more than one hydrocarbyl substituent groups located on an aromatic hydrocarbon ring or ring system carbon atom (e.g., a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphthyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

A heteroarene is aromatic compound, with or without side chains, having a heteroatom within the aromatic ring or aromatic ring system (e.g. pyridine, indole, or benzofuran, among others). A "heteroaryl group" is a class of "heterocyclyl group" and is a univalent group formed by removing a hydrogen atom from a heteroaromatic ring or ring system carbon atom of a heteroarene compound. By specifying that the hydrogen atom is removed from a ring carbon atom, a "heteroaryl group" is distinguished from an "arylheteryl group," in which a hydrogen atom is removed from a heteroaromatic ring or ring system heteroatom. For example, an indol-2-yl group illustrated below is one example of a "heteroaryl group," and an indol-1-yl group illustrated below is one example of an "arylheteryl" group."

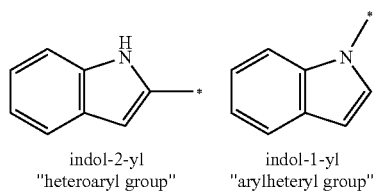

indol-2-yl "heteroaryl group"    indol-1-yl "arylheteryl group"

Similarly, a "heteroarylene group" refers to a group formed by removing two hydrogen atoms from a heteroarene compound, at least one of which is from a heteroarene ring or ring system carbon atom. Thus, in a "heteroarylene group," at least one hydrogen is removed from a heteroarene ring or ring system carbon atom, and the other hydrogen atom can be removed from any other carbon atom, including for example, a heteroarene ring or ring system carbon atom, or a non-heteroarene ring or ring system atom. A "heteroarene group" refers to a generalized group formed by removing one or more hydrogen atoms (as necessary for the particular group and at least one of which is a heteroarene ring or ring system carbon atom) from a heteroarene compound. If a hydrogen atom is removed from a heteroaromatic ring or ring system heteroatom and from a heteroaromatic ring or ring system carbon atom or an aromatic hydrocarbon ring or ring system carbon atom, the group is classified as an "arylheterylene group" or an "arylhetero group."

An "arylheteryl group" is a class of "cycloheteryl group" and is a univalent group formed by removing a hydrogen atom from a heteroaromatic ring or ring system heteroatom, as illustrated. By specifying that the hydrogen atom is removed from of a heteroaromatic ring or ring system heteroatom and not from a heteroaromatic ring or ring system carbon atom, an "arylheteryl group" is distinguished from a "heteroaryl group" in which a hydrogen atom is removed from a heteroaromatic ring or ring system carbon atom. Similarly, an "arylheterylene group" refers to a group formed by removing two hydrogen atoms from a heteroaryl compound, at least one of which is removed from a heteroaromatic ring or ring system heteroatom of the heteroaryl compound; the other hydrogen atom can be removed from any other atom, including for example, a heteroaromatic ring or ring system carbon atom, another heteroaromatic ring or ring system heteroatom, or a non-ring atom (carbon or heteroatom) from a heteroaromatic compound. An "arylhetero group" refers to a generalized group formed by removing one or more hydrogen atoms (as necessary for the particular group and at least one of which is from a heteroaromatic ring or ring system) heteroatom from a heteroarene compound.

An "aralkyl group" is an aryl-substituted alkyl group having a free valance at a non-aromatic carbon atom (e.g. a benzyl group, or a 2-phenyleth-1yl group, among others). Similarly, an "aralkylene group" is an aryl-substituted alkylene group having two free valences at a single non-aromatic carbon atom or a free valence at two non-aromatic carbon atoms while an "aralkane group" is a generalized is an aryl-substituted alkane group having one or more free valences at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having two free valences at a single non-heteroaromatic ring or ring system carbon atom or a free valence at two non-heteroaromatic ring or ring system carbon atoms while a "heteroaralkane group" is a generalized aryl-substituted alkane group having one or more free valences at a non-heteroaromatic ring or ring system carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g. the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning. Examples of halides include fluoride, chloride, bromide, and iodide.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer would be categorized an as ethylene/1-hexene copolymer.

In like manner, the scope of the term "polymerization" includes homopolymerization, copolymerization, terpolymerization, etc. Therefore, a copolymerization process would involve contacting one olefin monomer (e.g., ethylene) and one olefin comonomer (e.g., 1-hexene) to produce a copolymer.

The term "co-catalyst" is used generally herein to refer to compounds such as aluminoxane compounds, organoboron or organoborate compounds, ionizing ionic compounds, organoaluminum compounds, organozinc compounds, organomagnesium compounds, organolithium compounds, and the like, that can constitute one component of a catalyst composition, when used in addition to an activator-support. The term "co-catalyst" is used regardless of the actual function of the compound or any chemical mechanism by which the compound may operate.

The terms "chemically-treated solid oxide," "treated solid oxide compound," and the like, are used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide can comprise a calcined contact product of at least one solid oxide with at least one electron-withdrawing anion source compound. Typically, the chemically-treated solid oxide comprises at least one acidic solid oxide compound. The "activator-support" of the present invention can be a chemically-treated solid oxide. The terms "support" and "activator-support" are not used to imply these components are inert, and such components should not be construed as an inert component of the catalyst composition. The term "activator," as used herein, refers generally to a substance that is capable of converting a transition metal component into a catalyst that can polymerize olefins, or converting a contact product of a transition metal compound and a component that provides an activatable ligand (e.g., an alkyl, a hydride) to the transition metal compound, when the transition metal compound does not already comprise such a ligand, into a catalyst that can polymerize olefins. This term is used regardless of the actual activating mechanism. If the catalyst composition contains an activator-support, then aluminoxanes, organoboron or organoborate compounds, ionizing ionic compounds, and the like, are typically referred to as co-catalysts.

The term "fluoroorgano boron compound" is used herein with its ordinary meaning to refer to neutral compounds of the form $BY_3$. The term "fluoroorgano borate compound" also has its usual meaning to refer to the monoanionic salts of a fluoroorgano boron compound of the form $[cation]^+[BY_4]^-$, where Y represents a fluorinated organic group. Materials of these types are generally and collectively referred to as "organoboron or organoborate compounds."

Compounds having formula (Ia), (Ib), (IIa), (IIb), (IIIa), and/or (IIIb) can be described herein as amine bis(phenolate) complexes or compounds, N,N-bis[2-hydroxidebenzyl] amine complexes or compounds, bis[2-hydroxidebenzyl] amine complexes or compounds, or simply transition metal complexes or compounds, and such terminology will be used interchangeably throughout this disclosure to describe compounds having formulas (Ia), (Ib), (IIa), (IIb), (IIIa), and/or (IIIb).

The terms "catalyst composition," "catalyst mixture," "catalyst system," and the like, do not depend upon the actual product or composition resulting from the contact or reaction of the initial components of the claimed catalyst composition/mixture/system, the nature of the active catalytic site, or the fate of the co-catalyst, the transition metal compound(s), any olefin monomer used to prepare a precontacted mixture, or the activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, will be used interchangeably throughout this disclosure.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which can be blended, mixed, slurried, dissolved, reacted, treated, or otherwise contacted in some other manner.

The term "precontacted" mixture is used herein to describe a first mixture of catalyst components that are contacted for a first period of time prior to the first mixture being used to form a "postcontacted" or second mixture of catalyst components that are contacted for a second period of time. Typically, the precontacted mixture can describe a mixture of transition metal compound (one or more than one), olefin monomer (or monomers), and organoaluminum compound (or compounds), before this mixture is contacted with an activator-support(s) and optional additional organoaluminum compound. Thus, precontacted describes components that are used to contact each other, but prior to contacting the components in the second, postcontacted mixture. Accordingly, this invention can occasionally distinguish between a component used to prepare the precontacted mixture and that component after the mixture has been prepared. For example, according to this description, it is possible for the precontacted organoaluminum compound, once it is contacted with the transition metal compound and the olefin monomer, to have reacted to form at least one different chemical compound, formulation, or structure from the distinct organoaluminum compound used to prepare the precontacted mixture. In this case, the precontacted organoaluminum compound or component is described as comprising an organoaluminum compound that was used to prepare the precontacted mixture.

Additionally, the precontacted mixture can describe a mixture of transition metal compound(s) and organoaluminum compound(s), prior to contacting this mixture with an activator-support(s). This precontacted mixture also can describe a mixture of transition metal compound(s), olefin monomer(s), and activator-support(s), before this mixture is contacted with an organoaluminum co-catalyst compound or compounds.

Similarly, the term "postcontacted" mixture is used herein to describe a second mixture of catalyst components that are contacted for a second period of time, and one constituent of which is the "precontacted" or first mixture of catalyst components that were contacted for a first period of time. Typically, the term "postcontacted" mixture is used herein to describe the mixture of transition metal compound(s), olefin monomer(s), organoaluminum compound(s), and activator-support(s) formed from contacting the precontacted mixture of a portion of these components with any additional components added to make up the postcontacted mixture. Often, the activator-support can comprise a chemically-treated solid oxide. For instance, the additional component added to make up the postcontacted mixture can be a chemically-treated solid oxide (one or more than one), and optionally, can include an organoaluminum compound which is the same as or different from the organoaluminum compound used to prepare the precontacted mixture, as described herein. Accordingly, this invention can also occasionally distinguish between a component used to prepare the postcontacted mixture and that component after the mixture has been prepared.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants disclose several types of ranges in the present invention. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a $C_2$ to $C_{18}$ alkenyl group, or in alternative language an alkenyl group having from 2 to 18 carbon atoms, as used herein, refers to a moiety that can be selected independently from an alkenyl group having 2, 3, 4, 5, 6, 7, 8, 9, 10, 11, 12, 13, 14, 15, 16, 17, or 18 carbon atoms, as well as any range between these two numbers (for example, a $C_2$ to $C_8$ alkenyl group), and also including any combination of ranges between these two numbers (for example, a $C_2$ to $C_6$ and a $C_{12}$ to $C_{16}$ alkenyl group).

Similarly, another representative example follows for the catalyst activity of a catalyst composition provided in an aspect of this invention. By a disclosure that the catalyst activity can be in a range from about 4,000 to about 50,000 (g/g/hr), Applicants intend to recite that the catalyst activity can be about 4,000, about 5,000, about 6,000, about 7,000, about 8,000, about 9,000, about 10,000, about 15,000, about 20,000, about 25,000, about 30,000, about 35,000, about 40,000, about 45,000, or about 50,000 g/g/hr. Additionally, the catalyst activity can be within any range from about 4,000 to about 50,000 (for example, from about 7,000 to about 50,000), and this also includes any combination of ranges between about 4,000 and about 50,000 (for example, the activity can be in a range from about 4,000 to about 10,000, or from about 20,000 to about 50,000). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The following abbreviations are used in this disclosure:
Bn—benzyl
Et—ethyl
MAO—methylaluminoxane
Me—methyl
$M_w$—weight-average molecular weight
Ph—phenyl
t-Bu—tert-butyl
THF—tetrahydrofuran
TIBA—triisobutylaluminum

DETAILED DESCRIPTION OF THE INVENTION

The present invention is directed generally to new catalyst compositions, methods for preparing catalyst compositions, methods for using the catalyst compositions to polymerize olefins, the polymer resins produced using such catalyst compositions, and articles produced using these polymer resins. In particular, the present invention relates to amine bis(phenolate) or N,N-bis[2-hydroxidebenzyl]amine transition metal compounds, and catalyst compositions employing such transition metal compounds.

Amine Bis(Phenolate) Transition Metal Complexes

The present invention discloses novel amine bis(phenolate) complexes or compounds (e.g., N,N-bis[2-hydroxidebenzyl]amine complexes or compounds), and methods of making these complexes or compounds. In an embodiment of this invention, the N,N-bis[2-hydroxidebenzyl]amine compound can have the formula:

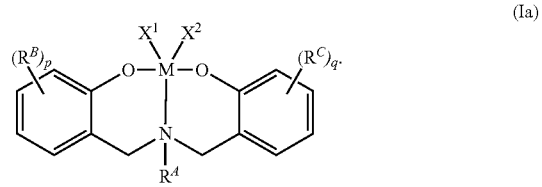

(Ia)

Within formula (Ia), M, $X^1$, $X^2$, $R^A$, $R^B$, $R^C$, p, and q are independent elements of the N,N-bis[2-hydroxidebenzyl]amine compound. Accordingly, the N,N-bis[2-hydroxidebenzyl]amine compound having formula (Ia) can be described using any combination of M, $X^1$, $X^2$, $R^A$, $R^B$, $R^C$, p, and q disclosed herein.

Unless otherwise specified, formula (Ia) above, any other structural formulas disclosed herein, and any N,N-bis[2-hydroxidebenzyl]amine complex, compound, or species disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In accordance with aspects of this invention, the metal in formula (Ia), M, can be Ti, Zr, or Hf. In one aspect, for instance, M can be Zr or Hf, while in another aspect, M can be Ti; alternatively, M can be Zr; or alternatively, M can be Hf.

$X^1$ and $X^2$ in formula (Ia) independently can be a monoanionic ligand. In some aspects, suitable monoanionic ligands can include, but are not limited to, H (hydride), $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $-OBR^1_2$, or $-OSO_2R^1$, wherein $R^1$ is a $C_1$ to $C_{36}$ hydrocarbyl group. It is contemplated that $X^1$ and $X^2$ can be either the same or a different monoanionic ligand.

In one aspect, $X^1$ and $X^2$ independently can be H, $BH_4$, a halide (e.g., F, Cl, Br, etc.), a $C_1$ to $C_{18}$ hydrocarbyl group, a $C_1$ to $C_{18}$ hydrocarboxy group, a $C_1$ to $C_{18}$ hydrocarbylaminyl group, a $C_1$ to $C_{18}$ hydrocarbylsilyl group, or a $C_1$ to $C_{18}$ hydrocarbylaminylsilyl group. Alternatively, $X^1$ and $X^2$ independently can be H, $BH_4$, a halide, $OBR^1_2$, or $OSO_2R^1$, wherein $R^1$ is a $C_1$ to $C_{18}$ hydrocarbyl group. In another aspect, $X^1$ and $X^2$ independently can be H, $BH_4$, a halide, a $C_1$ to $C_{12}$ hydrocarbyl group, a $C_1$ to $C_{12}$ hydrocarboxy group, a $C_1$ to $C_{12}$ hydrocarbylaminyl group, a $C_1$ to $C_{12}$ hydrocarbylsilyl group, a $C_1$ to $C_{12}$ hydrocarbylaminylsilyl group, $OBR^1_2$, or $OSO_2R^1$, wherein $R^1$ is a $C_1$ to $C_{12}$ hydrocarbyl group. In yet another aspect, $X^1$ and $X^2$ independently can be H, $BH_4$, a halide, a $C_1$ to $C_{10}$ hydrocarbyl group, a $C_1$ to $C_{10}$ hydrocarboxy group, a $C_1$ to $C_{10}$ hydrocarbylaminyl group, a $C_1$ to $C_{10}$ hydrocarbylsilyl group, a $C_1$ to $C_{10}$ hydrocarbylaminylsilyl group, $OBR^1_2$, or $OSO_2R^1$, wherein $R^1$ is a $C_1$ to $C_{10}$ hydrocarbyl group. In still another aspect, $X^1$ and $X^2$ independently can be H, $BH_4$, a halide, a $C_1$ to $C_8$ hydrocarbyl group, a $C_1$ to $C_8$ hydrocarboxy group, a $C_1$ to $C_8$ hydrocarbylaminyl group, a $C_1$ to $C_8$ hydrocarbylsilyl group, a $C_1$ to $C_8$ hydrocarbylaminylsilyl group, $OBR^1_2$, or $OSO_2R^1$, wherein $R^1$ is a $C_1$ to $C_8$ hydrocarbyl group.

The hydrocarbyl group which can be $X^1$ and/or $X^2$ in formula (Ia) can be a $C_1$ to $C_{36}$ hydrocarbyl group, including, but not limited to, a $C_1$ to $C_{36}$ alkyl group, a $C_2$ to $C_{36}$ alkenyl group, a $C_4$ to $C_{36}$ cycloalkyl group, a $C_6$ to $C_{36}$ aryl group, or a $C_7$ to $C_{36}$ aralkyl group. For instance, $X^1$ and $X^2$ independently can be a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, $X^1$ and $X^2$ independently can be a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; alternatively, $X^1$ and $X^2$ independently can be a $C_1$ to $C_{10}$ alkyl group, a $C_2$ to $C_{10}$ alkenyl group, a $C_4$ to $C_{10}$ cycloalkyl group, a $C_6$ to $C_{10}$ aryl group, or a $C_7$ to $C_{10}$ aralkyl group; or alternatively, $X^1$ and $X^2$ independently can be a $C_1$ to $C_5$ alkyl group, a $C_2$ to $C_5$ alkenyl group, a $C_5$ to $C_8$ cycloalkyl group, a $C_6$ to $C_8$ aryl group, or a $C_7$ to $C_8$ aralkyl group.

Accordingly, in some aspects, the alkyl group which can be $X^1$ and/or $X^2$ in formula (Ia) can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be $X^1$ and/or $X^2$ in formula (Ia) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

Suitable alkenyl groups which can be $X^1$ and/or $X^2$ in formula (Ia) can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. Such alkenyl groups can be linear or branched, and the double bond can be located anywhere in the chain. In one aspect, $X^1$ and/or $X^2$ in formula (Ia) can be an ethenyl group, a propenyl group, a butenyl group, a pentenyl group, a hexenyl group, a heptenyl group, an octenyl group, a nonenyl group, or a decenyl group, while in another aspect, $X^1$ and/or $X^2$ in formula (Ia) can be an ethenyl group, a propenyl group, a butenyl group, a pentenyl group, or a hexenyl group. For example, $X^1$ and/or $X^2$ can be an ethenyl group; alternatively, a propenyl group; alternatively, a butenyl group; alternatively, a pentenyl group; or alternatively, a hexenyl group. In yet another aspect, $X^1$ and/or $X^2$ can be a terminal alkenyl group, such as a $C_3$ to $C_{18}$ terminal alkenyl group, a $C_3$ to $C_{12}$ terminal alkenyl group, or a $C_3$ to $C_8$ terminal alkenyl group. Illustrative terminal alkenyl groups can include, but are not limited to, a prop-2-en-1-yl group, a bute-3-en-1-yl group, a pent-4-en-1-yl group, a hex-5-en-1-yl group, a hept-6-en-1-yl group, an octe-7-en-1-yl group, a non-8-en-1-yl group, a dece-9-en-1-yl group, and so forth.

$X^1$ and/or $X^2$ in formula (Ia) can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. For example, $X^1$ and/or $X^2$ in formula (Ia) can be a cyclopentyl group, a substituted cyclopentyl group, a cyclohexyl group, or a substituted cyclohexyl group. Moreover, $X^1$ and/or $X^2$ in formula (Ia) can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; alternatively, a cyclooctyl group or a substituted cyclooctyl group; alternatively, a cyclopentyl group; alternatively, a substituted cyclopentyl group; alternatively, a cyclohexyl group; or alternatively, a substituted cyclohexyl group. Substituents which can be utilized for the substituted cycloalkyl group are independently disclosed herein and can be utilized without limitation to further describe the substituted cycloalkyl group which can be $X^1$ and/or $X^2$ in formula (Ia).

In some aspects, the aryl group which can be $X^1$ and/or $X^2$ in formula (Ia) can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be $X^1$ and/or $X^2$ in formula (Ia).

In an aspect, the substituted phenyl group which can be $X^1$ and/or $X^2$ in formula (Ia) can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be the $X^1$ and/or $X^2$ group(s) in formula (Ia).

In some aspects, the aralkyl group which can be $X^1$ and/or $X^2$ group in formula (Ia) can be a benzyl group or a substituted benzyl group. In an aspect, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be the $X^1$ and/or $X^2$ group(s) in formula (Ia).

In an aspect, each non-hydrogen substituent(s) for the substituted cycloalkyl group, substituted aryl group, or substituted aralkyl group which can be $X^1$ and/or $X^2$ in formula (Ia) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups which can be $X^1$ and/or $X^2$ in formula (Ia). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group, and the like. Furthermore, the hydrocarbyl substituent can be a benzyl group, a phenyl group, a tolyl group, or a xylyl group, and the like.

A hydrocarboxy group is used generically herein to include, for instance, alkoxy, aryloxy, aralkoxy, and -(alkyl, aryl, or aralkyl)-O-(alkyl, aryl, or aralkyl) groups, and these groups can comprise up to about 36 carbon atoms (e.g., $C_1$ to $C_{36}$, $C_1$ to $C_{18}$, $C_1$ to $C_{10}$, or $C_1$ to $C_8$ hydrocarboxy groups). Illustrative and non-limiting examples of hydrocarboxy groups which can be $X^1$ and/or $X^2$ in formula (Ia) can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), and the like. In an aspect, the hydrocarboxy group which can be $X^1$ and/or $X^2$ in formula (Ia) can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; or alternatively, an acetylacetonate group.

The term hydrocarbylaminyl group is used generically herein to refer collectively to, for instance, alkylaminyl, arylaminyl, aralkylaminyl, dialkylaminyl, diarylaminyl, diaralkylaminyl, and -(alkyl, aryl, or aralkyl)-N-(alkyl, aryl, or aralkyl) groups, and unless otherwise specified, the hydrocarbylaminyl groups which can be $X^1$ and/or $X^2$ in formula (Ia) can comprise up to about 36 carbon atoms (e.g., $C_1$ to $C_{36}$, $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group which can be $X^1$ and/or $X^2$ in formula (Ia) can be, for instance, a methylaminyl group ($—NHCH_3$), an ethylaminyl group ($—NHCH_2CH_3$), an n-propylaminyl group ($—NHCH_2CH_2CH_3$), an iso-propylaminyl group ($—NHCH(CH_3)_2$), an n-butylaminyl group ($—NHCH_2CH_2CH_2CH_3$), a t-butylaminyl group ($—NHC(CH_3)_3$), an n-pentylaminyl group ($—NHCH_2CH_2CH_2CH_2CH_3$), a neo-pentylaminyl group ($—NHCH_2C(CH_3)_3$), a phenylaminyl group ($—NHC_6H_5$), a tolylaminyl group ($—NHC_6H_4CH_3$), or a xylylaminyl group ($—NHC_6H_3(CH_3)_2$); alternatively, a methylaminyl group; alternatively, an ethylaminyl group; alternatively, a propylaminyl group; or alternatively, a phenylaminyl group. In other aspects, the hydrocarbylaminyl group which can be $X^1$ and/or $X^2$ in formula (Ia) can be, for instance, a dimethylaminyl group ($—N(CH_3)_2$), a diethylaminyl group ($—N(CH_2CH_3)_2$), a di-n-propylaminyl group ($—N(CH_2CH_2CH_3)_2$), a di-iso-propylaminyl group ($—N(CH(CH_3)_2)_2$), a di-n-butylaminyl group ($—N(CH_2CH_2CH_2CH_3)_2$), a di-t-butylaminyl group ($—N(C(CH_3)_3)_2$), a di-n-pentylaminyl group ($—N(CH_2CH_2CH_2CH_2CH_3)_2$), a di-neo-pentylaminyl group ($—N(CH_2C(CH_3)_3)_2$), a di-phenylaminyl group ($—N(C_6H_5)_2$), a di-tolylaminyl group ($—N(C_6H_4CH_3)_2$), or a di-xylylaminyl group ($—N(C_6H_3(CH_3)_2)_2$); alternatively, a dimethylaminyl group; alternatively, a di-ethylaminyl group; alternatively, a di-n-propylaminyl group; or alternatively, a di-phenylaminyl group.

In accordance with some aspects disclosed herein, one or both of $X^1$ and $X^2$ independently can be a $C_1$ to $C_{36}$ hydrocarbylsilyl group; alternatively, a $C_1$ to $C_{24}$ hydrocarbylsilyl group; alternatively, a $C_1$ to $C_{18}$ hydrocarbylsilyl group; or alternatively, a $C_1$ to $C_8$ hydrocarbylsilyl group. In an aspect, each hydrocarbyl (one or more) of the hydrocarbylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). As used herein, hydrocarbylsilyl is intended to cover (mono) hydrocarbylsilyl (—$SiH_2R$), dihydrocarbylsilyl (—$SiHR_2$), and trihydrocarbylsilyl (—$SiR_3$) groups, with R being a hydrocarbyl group. In one aspect, the hydrocarbylsilyl group can be a $C_3$ to $C_{36}$ or a $C_3$ to $C_{18}$ trihydrocarbylsilyl group, such as, for example, a trialkylsilyl group or a triphenylsilyl group. Illustrative and non-limiting examples of hydrocarbylsilyl groups which can be the $X^1$ and/or $X^2$ group(s) in formula (Ia) can include, but are not limited to, trimethylsilyl, triethylsilyl, tripropylsilyl (e.g., triisopropylsilyl), tributylsilyl, tripentylsilyl, triphenylsilyl, allyldimethylsilyl, and the like.

A hydrocarbylaminylsilyl group is used herein to refer to groups containing at least one hydrocarbon moiety, at least one N atom, and at least one Si atom. Illustrative and non-limiting examples of hydrocarbylaminylsilyl groups which can be $X^1$ and/or $X^2$ can include, but are not limited to —$N(SiMe_3)_2$, —$N(SiEt_3)_2$, and the like. Unless otherwise specified, the hydrocarbylaminylsilyl groups which can be $X^1$ and/or $X^2$ can comprise up to about 36 carbon atoms (e.g., $C_1$ to $C_{36}$, $C_1$ to $C_{18}$, $C_1$ to $C_{12}$, or $C_1$ to $C_8$ hydrocarbylaminylsilyl groups). In an aspect, each hydrocarbyl (one or more) of the hydrocarbylaminylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). Moreover, hydrocarbylaminylsilyl is intended to cover —$NH(SiH_2R)$, —$NH(SiHR_2)$, —$NH(SiR_3)$, —$N(SiH_2R)_2$, —$N(SiHR_2)_2$, —$N(SiR_3)_2$, groups, among others, with R being a hydrocarbyl group.

In an aspect, $X^1$ and $X^2$ independently can be —$OBR^1_2$ or —$OSO_2R^1$, wherein $R^1$ is a $C_1$ to $C_{36}$ hydrocarbyl group, or alternatively, a $C_1$ to $C_{18}$ hydrocarbyl group. The hydrocarbyl group in $OBR^1_2$ and/or $OSO_2R^1$ independently can be any hydrocarbyl group disclosed herein, such as, for instance, a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; or a $C_1$ to $C_8$ alkyl group, a $C_2$ to $C_8$ alkenyl group, a $C_5$ to $C_8$ cycloalkyl group, a $C_6$ to $C_8$ aryl group, or a $C_7$ to $C_8$ aralkyl group.

In one aspect, $X^1$ and $X^2$ independently can be H, $BH_4$, a halide, or a $C_1$ to $C_{36}$ hydrocarbyl group, hydrocarboxy group, hydrocarbylaminyl group, hydrocarbylsilyl group, or hydrocarbylaminylsilyl group, while in another aspect, $X^1$ and $X^2$ independently can be H, $BH_4$, or a $C_1$ to $C_{18}$ hydrocarboxy group, hydrocarbylaminyl group, hydrocarbylsilyl group, or hydrocarbylaminylsilyl group. In yet another aspect, $X^1$ and $X^2$ independently can be a halide; alternatively, a $C_1$ to $C_{18}$ hydrocarbyl group; alternatively, a $C_1$ to $C_{18}$ hydrocarboxy group; alternatively, a $C_1$ to $C_{18}$ hydrocarbylaminyl group; alternatively, a $C_1$ to $C_{18}$ hydrocarbylsilyl group; or alternatively, a $C_1$ to $C_{18}$ hydrocarbylaminylsilyl group. In still another aspect, both $X^1$ and $X^2$ can be H; alternatively, F; alternatively, Cl; alternatively, Br; alternatively, I; alternatively, $BH_4$; alternatively, a $C_1$ to $C_{18}$ hydrocarbyl group; alternatively, a $C_1$ to $C_{18}$ hydrocarboxy group; alternatively, a $C_1$ to $C_{18}$ hydrocarbylaminyl group; alternatively, a $C_1$ to $C_{18}$ hydrocarbylsilyl group; or alternatively, a $C_1$ to $C_{18}$ hydrocarbylaminylsilyl group.

$X^1$ and $X^2$ independently can be, in some aspects, H, a halide, methyl, phenyl, benzyl, an alkoxy, an aryloxy, acetylacetonate, an alkylaminyl, a dialkylaminyl, a trihydrocarbylsilyl, or a hydrocarbylaminylsilyl; alternatively, H, a halide, methyl, phenyl, or benzyl; alternatively, an alkoxy, an aryloxy, or acetylacetonate; alternatively, an alkylaminyl or a dialkylaminyl; alternatively, a trihydrocarbylsilyl or hydrocarbylaminylsilyl; alternatively, H or a halide; alternatively, methyl, phenyl, benzyl, an alkoxy, an aryloxy, acetylacetonate, an alkylaminyl, or a dialkylaminyl; alternatively, H; alternatively, a halide; alternatively, methyl; alternatively, phenyl; alternatively, benzyl; alternatively, an alkoxy; alternatively, an aryloxy; alternatively, acetylacetonate; alternatively, an alkylaminyl; alternatively, a dialkylaminyl; alternatively, a trihydrocarbylsilyl; or alternatively, a hydrocarbylaminylsilyl. In these and other aspects, the alkoxy, aryloxy, alkylaminyl, dialkylaminyl, trihydrocarbylsilyl, and hydrocarbylaminylsilyl can be a $C_1$ to $C_{36}$, a $C_1$ to $C_{18}$, a $C_1$ to $C_{12}$, or a $C_1$ to $C_8$ alkoxy, aryloxy, alkylaminyl, dialkylaminyl, trihydrocarbylsilyl, and hydrocarbylaminylsilyl.

Moreover, $X^1$ and $X^2$ independently can be, in certain aspects, a halide or a $C_1$ to $C_{18}$ hydrocarbyl group; alternatively, a halide or a $C_1$ to $C_8$ hydrocarbyl group; alternatively, F, Cl, Br, I, methyl, benzyl, or phenyl; alternatively, Cl, methyl, benzyl, or phenyl; alternatively, a $C_1$ to $C_{18}$ alkoxy, aryloxy, alkylaminyl, dialkylaminyl, trihydrocarbylsilyl, or hydrocarbylaminylsilyl group; alternatively, a $C_1$ to $C_8$ alkoxy, aryloxy, alkylaminyl, dialkylaminyl, trihydrocarbylsilyl, or hydrocarbylaminylsilyl group; or alternatively, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl.

In formula (Ia), each $R^B$ and/or $R^C$ independently can be a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group. In some aspects, each $R^B$ and/or $R^C$ independently can be a halide; alternatively, a $C_1$ to $C_{18}$ hydrocarbyl group; alternatively, a $C_1$ to $C_{18}$ halogenated hydrocarbyl group; alternatively, a $C_1$ to $C_{18}$ hydrocarboxy group; or alternatively, a $C_1$ to $C_{18}$ hydrocarbylsilyl group. Importantly, each $R^B$ and/or $R^C$ can be either the same or a different substituent group. Moreover, each $R^B$ and/or $R^C$ can be at any of the four positions of the respective ring structure shown in formula (Ia). In an aspect, the number of $R^B$s and/or $R^C$s and/or the positions of each $R^B$ and/or $R^C$ are independent of each other. For instance, two or more $R^B$s can be different, or alternatively, all $R^B$s can be the same. Additionally or alternatively, two or more $R^C$s can be different, or alternatively, all $R^C$s can be the same. In another aspect, one or more of the $R^B$s can be different from the one or more of the $R^C$s, or alternatively, all $R^B$s can be the same as the $R^C$s. In these and other aspects, each $R^B$ and/or $R^C$ can be at any of the four positions of the respective ring structure shown in formula (Ia).

The halide, $C_1$ to $C_{36}$ hydrocarbyl group, $C_1$ to $C_{36}$ hydrocarboxy group, and $C_1$ to $C_{36}$ hydrocarbylsilyl group which can be a $R^B$ and/or $R^C$ in formula (Ia) can be any halide, $C_1$ to $C_{36}$ hydrocarbyl group, $C_1$ to $C_{36}$ hydrocarboxy group, and $C_1$ to $C_{36}$ hydrocarbylsilyl group described herein (e.g., as pertaining to $X^1$ and $X^2$ in formula (Ia)). A $R^B$ and/or $R^C$ in formula (Ia) can be, in certain aspects, a $C_1$ to $C_{36}$ halogenated hydrocarbyl group, where the halogenated hydrocarbyl group indicates the presence of one or more halogen atoms replacing an equivalent number of hydrogen atoms in the hydrocarbyl group. The halogenated hydrocarbyl group often can be a halogenated alkyl group, a halogenated alkenyl group, a halogenated cycloalkyl group, a halogenated aryl group, or a halogenated aralkyl group. Representative and non-limiting halogenated hydrocarbyl groups include pentafluorophenyl, trifluoromethyl ($CF_3$), and the like.

As a non-limiting example, each $R^B$ and/or $R^C$ in formula (Ia) independently can be Cl, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group (or other substituted aryl group), a benzyl group, a naphthyl group, a trimethylsilyl group, a triisopropylsilyl group, a triphenylsilyl group, or an allyldimethylsilyl group; alternatively, Cl; alternatively, $CF_3$; alternatively, a methyl group; alternatively, an ethyl group; alternatively, a propyl group; alternatively, a butyl group; alternatively, a pentyl group; alternatively, a hexyl group; alternatively, a heptyl group; alternatively, an octyl group, a nonyl group; alternatively, a decyl group; alternatively, an ethenyl group; alternatively, a propenyl group; alternatively, a butenyl group; alternatively, a pentenyl group; alternatively, a hexenyl group; alternatively, a heptenyl group; alternatively, an octenyl group; alternatively, a nonenyl group; alternatively, a decenyl group; alternatively, a phenyl group; alternatively, a tolyl group; alternatively, a benzyl group; alternatively, a naphthyl group; alternatively, a trimethylsilyl group; alternatively, a triisopropylsilyl group; alternatively, a triphenylsilyl group; or alternatively, an allyldimethylsilyl group.

In formula (Ia), p can be 0, 1, 2, 3, or 4, and, independently, q can be 0, 1, 2, 3, or 4. In some aspects, p can be 0, 1, or 2, and q can be 0, 1, or 2, while in other aspects, p can be 0 or 2, and q can be 0 or 2. For instance, p can be equal to 0, q can be equal to 0, or both p and q can be equal to 0. Alternatively, p can be equal to 2, q can be equal to 2, or both p and q can be equal to 2. As noted above, each $R^B$ and/or $R^C$ can be either the same or a different substituent group. For example, when p is 2, 3, or 4, each $R^B$ independently can be the same or different.

$R^A$ in formula (Ia) can be a $C_1$ to $C_{36}$ hydrocarbyl group or $C_1$ to $C_{36}$ halogenated hydrocarbyl group, and these groups can be any $C_1$ to $C_{36}$ hydrocarbyl group or $C_1$ to $C_{36}$ halogenated hydrocarbyl group described herein (e.g., as pertaining to $X^1$, $X^2$, $R^B$, and $R^C$ in formula (Ia)). In some aspects, $R^A$ can be a $C_1$ to $C_{24}$ hydrocarbyl group or a $C_1$ to $C_{24}$ halogenated hydrocarbyl group, while in other aspects, $R^A$ can be a $C_1$ to $C_{18}$ hydrocarbyl group or a $C_1$ to $C_{18}$ halogenated hydrocarbyl group. For example, $R^A$ can be a $C_1$ to $C_{12}$ hydrocarbyl group, such as a $C_1$ to $C_{12}$ alkyl group, a $C_1$ to $C_{10}$ alkyl group, a $C_1$ to $C_8$ alkyl group, a $C_2$ to $C_8$ alkyl group, a $C_2$ to $C_{12}$ alkenyl group, a $C_2$ to $C_{10}$ alkenyl group, a $C_2$ to $C_8$ alkenyl group, a $C_3$ to $C_{12}$ alkenyl group, a $C_3$ to $C_{10}$ alkenyl group, or a $C_3$ to $C_8$ alkenyl group, and the like. In one aspect, $R^A$ can be a methyl group, ethyl group, propyl group, butyl group, pentyl group, hexyl group, heptyl group, octyl group, nonyl group, decyl group, ethenyl group, propenyl group, butenyl group, pentenyl group, hexenyl group, heptenyl group, octenyl group, nonenyl group, decenyl group, phenyl group, tolyl group, benzyl group, phenylethyl group, or naphthyl group. In another aspect, $R^A$ can be a methyl group, ethyl group, propyl group, butyl group, pentyl group, hexyl group, propenyl group, butenyl group, pentenyl group, hexenyl group, phenyl group, benzyl group, or phenylethyl group. In yet another aspect, $R^A$ can an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group; alternatively, an ethenyl group, a propenyl group, a butenyl group, a pentenyl group, a hexenyl group, a heptenyl group, an octenyl group, a nonenyl group, or a decenyl group; alternatively, an ethenyl group, a propenyl group, a butenyl group, a pentenyl group, or a hexenyl group; alternatively, an ethenyl group; alternatively, a propenyl group; alternatively, a butenyl group; alternatively, a pentenyl group; or alternatively, a hexenyl group. In still another aspect, $R^A$ can be a terminal alkenyl group, such as a $C_3$ to $C_{36}$ terminal alkenyl group, a $C_3$ to $C_{24}$ terminal alkenyl group, a $C_3$ to $C_{18}$ terminal alkenyl group, a $C_3$ to $C_{12}$ terminal alkenyl group, or a $C_3$ to $C_8$ terminal alkenyl group.

In another embodiment of this invention, the N,N-bis[2-hydroxidebenzyl]amine compound can have the formula:

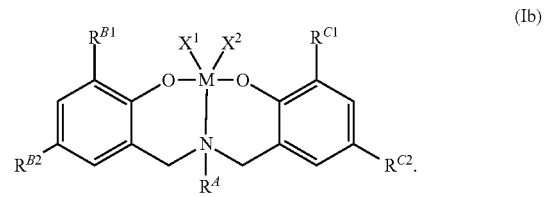

(Ib)

Within formula (Ib), M, $X^1$, $X^2$, $R^A$, $R^{B1}$, $R^{B2}$, $R^{C1}$, and $R^{C2}$ are independent elements of the N,N-bis[2-hydroxidebenzyl]amine compound. Accordingly, the N,N-bis[2-hydroxidebenzyl]amine compound having formula (Ib) can be described using any combination of M, $X^1$, $X^2$, $R^A$, $R^{B1}$, $R^{B2}$, $R^{C1}$, and $R^{C2}$ disclosed herein.

The selections for M, $X^1$, $X^2$, and $R^A$ in formula (Ib) are the same as those described herein above for formula (Ia). $R^{B1}$, $R^{B2}$, $R^{C1}$, and $R^{C2}$ independently can be a halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group, and these groups can be any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group described herein (e.g., as pertaining to $R^B$ and $R^C$ in formula (Ia)).

In one aspect, for example, $R^{B1}$, $R^{B2}$, $R^{C1}$, and $R^{C2}$ independently can be a methyl group, ethyl group, propyl group, butyl group (e.g., t-Bu), pentyl group, hexyl group, propenyl group, butenyl group, pentenyl group, hexenyl group, phenyl group, tolyl group, benzyl group, trimethylsilyl group, triisopropylsilyl group, triphenylsilyl group, allyldimethylsilyl group, $CF_3$, or Cl. In another aspect, $R^{B1}$, $R^{B2}$, $R^{C1}$ and $R^{C2}$ independently can be a methyl group, ethyl group, propyl group, butyl group, pentyl group, hexyl group, propenyl group, butenyl group, pentenyl group, hexenyl group, phenyl group, tolyl group, or benzyl group. In yet another aspect, at least one of $R^{B1}$, $R^{B2}$, $R^{C1}$, and $R^{C2}$ (or alternatively, each of $R^{B1}$, $R^{B2}$, $R^{C1}$, and $R^{C2}$) can be a methyl group; alternatively, an ethyl group; alternatively, a propyl group; alternatively, a butyl group; alternatively, a pentyl group; alternatively, a hexyl group; alternatively, a propenyl group; alternatively, a butenyl group; alternatively, a pentenyl group; alternatively, a hexenyl group; alternatively, a phenyl group; alternatively, a tolyl group; alternatively, a benzyl group; alternatively, a trimethylsilyl group; alternatively, a triisopropylsilyl group; alternatively, a triphenylsilyl group; alternatively, an allyldimethylsilyl group; alternatively, $CF_3$; or alternatively, Cl. In these and other aspects, $R^A$ in formula (Ib) can be a $C_1$ to $C_{18}$ hydrocarbyl group or $C_1$ to $C_{18}$ halogenated hydrocarbyl group, examples of which can include, but are not limited to, a methyl group, ethyl group, propyl group, butyl group, pentyl group, hexyl group, propenyl group, butenyl group, pentenyl group, hexenyl group, phenyl group, benzyl group, phenylethyl group, and the like.

Illustrative and non-limiting examples of N,N-bis[2-hydroxidebenzyl]amine compounds having formula (Ia) and formula (Ib) can include, but are not limited to, compounds TM-1, TM-2, and TM-3 illustrated in FIG. 1.

Methods of making transition metal complexes of the present invention also are provided herein. Examples 1-8 that follow provide representative procedures for synthesizing compounds having formula (Ia) and formula (Ib), or for synthesizing precursor compounds useful in the subsequent synthesis of compounds having formula (Ia) and formula (Ib). Additional methods for preparing compounds having formula (Ia) and formula (Ib) can be found in U.S. Pat. Nos. 6,333,423 and 6,596,827, the disclosures of which are incorporated herein by reference in their entirety. Using analogous synthesis schemes to those provided herein or known to those of skill in the art, transition metal complexes similar to TM-1, TM-2, and TM-3, but with monoanionic ligands other than benzyl (e.g., halide, hydrocarbylaminyl, hydrocarbylsilyl, other hydrocarbyl, etc.), and/or with substituents other than tert-butyl (e.g., halide, hydrocarboxy, hydrocarbylsilyl, other hydrocarbyl, etc.), can be derived.

In another embodiment of this invention, the N,N-bis[2-hydroxidebenzyl]amine compound can have the formula:

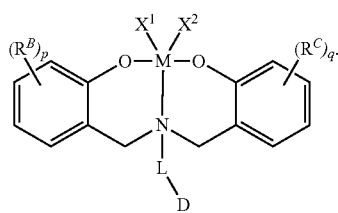
(IIa)

Within formula (IIa), M, $X^1$, $X^2$, $R^B$, $R^C$, p, q, L, and D are independent elements of the N,N-bis[2-hydroxidebenzyl] amine compound. Accordingly, the N,N-bis[2-hydroxidebenzyl]amine compound having formula (IIa) can be described using any combination of M, $X^1$, $X^2$, $R^B$, $R^C$, p, q, L, and D disclosed herein.

The selections for M, $X^1$, $X^2$, $R^B$, $R^C$, p, and q in formula (IIa) are the same as those described herein above for formula (Ia). For instance, M can be Ti, Zr, or Hf; alternatively, M can be Ti; alternatively, M can be Zr; or alternatively, M can be Hf. $X^1$ and $X^2$ in formula (IIa) independently can be any monoanionic ligand disclosed herein, and this includes, but is not limited to, H, $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $-OBR^1_2$, or $-OSO_2R^1$, wherein $R^1$ is a $C_1$ to $C_{36}$ hydrocarbyl group. In some aspects, it is contemplated that $X^1$ and $X^2$ independently can be a $C_1$ to $C_{18}$ hydrocarbyl group, a $C_1$ to $C_{18}$ hydrocarboxy group, a $C_1$ to $C_{18}$ hydrocarbylaminyl group, a $C_1$ to $C_{18}$ hydrocarbylsilyl group, or a $C_1$ to $C_{18}$ hydrocarbylaminylsilyl group, while in other aspects, $X^1$ and $X^2$ independently can be a halide or a $C_1$ to $C_{18}$ hydrocarbyl group. In formula (IIa), each $R^B$ and/or $R^C$ independently can be any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group disclosed herein. For example, each $R^B$ and/or $R^C$ independently can be Cl, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, a naphthyl group, a trimethylsilyl group, a triisopropylsilyl group, a triphenylsilyl group, or an allyldimethylsilyl group. The integers, p and q, independently can be 0, 1, 2, 3, or 4, such as, for instance, p can be 0, 1, or 2, and q can be 0, 1, or 2.

L in formula (IIa) can be a $C_1$ to $C_{18}$ hydrocarbylene group. Selections for the $C_1$ to $C_{18}$ hydrocarbylene group can be any $C_1$ to $C_{18}$ hydrocarbyl group disclosed herein from which another hydrogen atom can be removed. In one aspect, the hydrocarbylene group which can be L in formula (IIa) can be a $C_1$ to $C_{18}$ alkylene group, a $C_4$ to $C_{18}$ cycloalkylene group, a $C_6$ to $C_{18}$ arylene group, or a $C_7$ to $C_{18}$ aralkylene group. In another aspect, L can be a $C_2$ to $C_{18}$ hydrocarbylene group, a $C_2$ to $C_{15}$ hydrocarbylene group, a $C_2$ to $C_8$ hydrocarbylene group, a $C_2$ to $C_4$ hydrocarbylene group, a $C_1$ to $C_{15}$ hydrocarbylene group, a $C_1$ to $C_8$ hydrocarbylene group, or a $C_1$ to $C_4$ hydrocarbylene group. In yet another aspect, L can be a $C_1$ to $C_{15}$ alkylene group, a $C_4$ to $C_{15}$ cycloalkylene group, a $C_6$ to $C_{15}$ arylene group, or a $C_7$ to $C_{15}$ aralkylene group; alternatively, a $C_1$ to $C_{12}$ alkylene group, a $C_4$ to $C_{12}$ cycloalkylene group, a $C_6$ to $C_{12}$ arylene group, or a $C_7$ to $C_{12}$ aralkylene group; alternatively, a $C_1$ to $C_{10}$ alkylene group, a $C_4$ to $C_{10}$ cycloalkylene group, a $C_6$ to $C_{10}$ arylene group, or a $C_7$ to $C_{10}$ aralkylene group; or alternatively, a $C_2$ to $C_5$ alkylene group, a $C_5$ to $C_8$ cycloalkylene group, a $C_6$ to $C_8$ arylene group, or a $C_7$ to $C_8$ aralkylene group.

In some aspects, the alkylene group which can be L in formula (IIa) can be a methylene group, an ethylene group, a propylene group, a butylene group, a pentylene group, a hexylene group, a heptylene group, an octylene group, a nonylene group, a decylene group, a undecylene group, a dodecylene group, a tridecylene group, a tetradecylene group, a pentadecylene group, a hexadecylene group, a heptadecylene group, or an octadecylene group; alternatively, a methylene group, an ethylene group, a propylene group, a butylene group, a pentylene group, a hexylene group, a heptylene group, an octylene group, a nonylene group, or a decylene group; alternatively, a methylene group, an ethylene group, a propylene group, a butylene group, or a pentylene group. In other aspects, L can be a methylene group; alternatively, an ethylene group ($-CH_2CH_2-$); alternatively, a propylene group; alternatively, a butylene group; alternatively, a pentylene group; alternatively, a hexylene group; alternatively, a heptylene group; alternatively, an octylene group; alternatively, a nonylene group; alternatively, a decylene group; alternatively, a undecylene group; alternatively, a dodecylene group; alternatively, a tridecylene group; alternatively, a tetradecylene group; alternatively, a pentadecylene group; alternatively, a hexadecylene group; alternatively, a heptadecylene group; or alternatively, an octadecylene group. Moreover, L can be an eth-1,2-ylene group, a prop-1,3-ylene group, a but-1,4-ylene group, a but-2,3-ylene group, a pent-1,5-ylene group, a 2,2-dimethylprop-1,3-ylene group, a hex-1,6-ylene group, or a 2,3-dimethylbut-2,3-ylene group; alternatively, an eth-1,2-ylene group, a prop-1,3-ylene group, a but-1,4-ylene group, a pent-1,5-ylene group, or a hex-1,6-ylene group; alternatively, an eth-1,2-ylene group; alternatively, a prop-1, 3-ylene group; alternatively, a but-1,4-ylene group; alternatively, a but-2,3-ylene group; alternatively, a pent-1,5-ylene group; alternatively, a 2,2-dimethylprop-1,3-ylene group; alternatively, a hex-1,6-ylene group; or alternatively, a 2,3-dimethylbut-2,3-ylene group.

L in formula (IIa) can be a cycloalkylene group, including, but not limited to, a cyclobutylene group, a substituted cyclobutylene group, a cyclopentylene group, a substituted cyclopentylene group, a cyclohexylene group, a substituted cyclohexylene group, a cycloheptylene group, a substituted cycloheptylene group, a cyclooctylene group, or a substituted cyclooctylene group. For example, L can be a cyclobutylene group or a substituted cyclobutylene group; alternatively, a cyclopentylene group or a substituted cyclopentylene group; alternatively, a cyclohexylene group or a substituted cyclohexylene group; alternatively, a cycloheptylene group or a substituted cycloheptylene group; alternatively, a cyclooctylene group or a substituted cyclooctylene group; alternatively, a cyclopentylene group; alternatively, a substituted cyclopentylene group; alternatively, a cyclohexylene group; or alternatively, a substituted cyclohexylene group. In an aspect, L can be a cyclopent-1,3-ylene group, a substituted cyclopent-1,3-ylene group, a cyclohex-1,3-ylene group, a substituted cyclohex-1,3-ylene group, a cyclohex-1,4-ylene group, or a substituted cyclohex-1,4-ylene group; alternatively, a cyclopent-1,3-ylene group, a cyclohex-1,3-ylene group, or a cyclohex-1,4-ylene group. In another aspect, L can be a cyclopent-1,3-ylene group or a substituted cyclopent-1,3-ylene group; alternatively, a cyclohex-1,3-ylene group, a substituted cyclohex-1,3-ylene group, a cyclohex-1,4-ylene group, or a substituted cyclohex-1,4-ylene group; alternatively, a cyclohex-1,3-ylene group or a substituted cyclohex-1,3-ylene group; alternatively, a cyclohex-1,4-ylene group or a substituted cyclohex-1,4-ylene group; alternatively, a cyclopent-1,3-ylene group, a cyclohex-1,3-ylene group, or a cyclohex-1,4-ylene group; or alternatively, a substituted cyclopent-1,3-ylene group, a substituted cyclohex-1,3-ylene group, or a substituted cyclohex-1,4-ylene group. In another aspect, L can be a cyclopent-1,3-ylene group; alternatively, a substituted cyclopent-1,3-ylene group; alternatively, a cyclohex-1,3-ylene group; alternatively, a substituted cyclohex-1,3-ylene group; alternatively, a cyclohex-1,4-ylene group; or alternatively, a substituted cyclohex-1,4-ylene group. In another aspect, L can be a 2-substituted cyclopen-1,3-ylene group, a 4,5-disubstituted cyclopen-1,3-ylene group, a 2,5-disubstituted cyclopen-1,3-ylene group, or a 2,4,5-trisubstituted cyclopen-1,3-ylene group; alternatively, a 2-substituted cyclopen-1,3-ylene group; alternatively, a 4,5-disubstituted cyclopen-1,3-ylene group; alternatively, a 2,5-disubstituted cyclopen-1,3-ylene group; alternatively, a 2,4,5-trisubstituted cyclopen-1,3-ylene group. In another aspect, L can be a 2,6-disubstituted cyclohex-1,4-ylene group, a 2,3-disubstituted cyclohex-1,4-ylene group, a 2,5-disubstituted cyclohex-1,4-ylene group, or a 2,3,5,6-tetrasubstituted cyclohex-1,4-ylene group. In another aspect, L can be a 2,6-disubstituted cyclohex-1,4-ylene group or a 2,5-disubstituted cyclohex-1,4-ylene group; alternatively, a 2,6-disubstituted cyclohex-1,4-ylene group; alternatively, a 2,3-disubstituted cyclohex-1,4-ylene group; alternatively, a 2,5-disubstituted cyclohex-1,4-ylene group; or alternatively, a 2,3,5,6-tetrasubstituted cyclohex-1,4-ylene group. In yet another aspect, L can be a 2-substituted cyclohex-1,3-ylene group, a 2,4-disubstituted cyclohex-1,3-ylene group, a 4,6-disubstituted cyclohex-1,3-ylene group, or a 2,4,6-trisubstituted cyclohex-1,3-ylene group. In still another aspect, L can be a 2-substituted cyclohex-1,3-ylene group; alternatively, a 2,4-disubstituted cyclohex-1,3-ylene group; alternatively, a 4,6-disubstituted cyclohex-1,3-ylene group; or alternatively, a 2,4,6-trisubstituted cyclohex-1,3-ylene group. The substituent(s) for a substituted cycloalkylene group in formula (IIa) can be any substituent (e.g., a $C_1$ to $C_{12}$ hydrocarbyl group, a $C_1$ to $C_8$ alkyl group, etc.) disclosed herein above, e.g., in relation to substituted cycloalkyl groups in formula (Ia).

In formula (IIa), L can be an arylene group, e.g., a phenylene group, a substituted phenylene group, a naphthylene group, or a substituted naphthylene group. In one aspect, L can be a phenylene group; alternatively, a substituted phenylene group; alternatively, a naphthylene group; or alternatively, a substituted naphthylene group. In another aspect, L can be a phen-1,2-ylene group or a substituted phen-1,2-ylene group; alternatively, a phen-1,2-ylene group; or alternatively, a substituted phen-1,2-ylene group. In another aspect, L can be a phen-1,3-ylene group or a substituted phen-1,3-ylene group; alternatively, a phen-1,3-ylene group; or alternatively, a substituted phen-1,3-ylene group. In another aspect, L can be a phen-1,4-ylene group or a substituted phen-1,4-ylene group; alternatively, a phen-1,4-ylene group; or alternatively, a substituted phen-1,4-ylene group. In another aspect, L can be a phen-1,2-ylene group, a phen-1,3-ylene group, or a phen-1,4-ylene group; alternatively, a phen-1,3-ylene group or a phen-1,4-ylene group. In another aspect, L can be a substituted phen-1,2-ylene group, a substituted phen-1,3-ylene group, or a substituted phen-1,4-ylene group; alternatively, a substituted phen-1,3-ylene group or a substituted phen-1,4-ylene group. In another aspect, L can be a 2,6-disubstituted phen-1,4-ylene group, a 2,3-disubstituted phen-1,4-ylene group, a 2,5-disubstituted phen-1,4-ylene group, or a 2,3,5,6-tetrasubstituted phen-1,4-ylene group. In another aspect, L can be a 2,6-disubstituted phen-1,4-ylene group or a 2,5-disubstituted phen-1,4-ylene group; alternatively, a 2,6-disubstituted phen-1,4-ylene group; alternatively, a 2,3-disubstituted phen-1,4-ylene group; alternatively, a 2,5-disubstituted phen-1,4-ylene group; or alternatively, a 2,3,5,6-tetrasubstituted phen-1,4-ylene group. In yet another aspect, L can be a 2-substituted phen-1,3-ylene group, a 2,4-disubstituted phen-1,3-ylene group, a 4,6-disubstituted phen-1,3-ylene group, or a 2,4,6-trisubstituted phen-1,3-ylene group. In still another aspect, L can be a 2-substituted phen-1,3-ylene group; alternatively, a 2,4-disubstituted phen-1,3-ylene group; alternatively, a 4,6-disubstituted phen-1,3-ylene group; or alternatively, a 2,4,6-trisubstituted phen-1,3-ylene group. In some aspects, L can be a naphth-1,3-ylene group, a substituted naphth-1,3-ylene group, a naphth-1,4-ylene group, a substituted naphth-1,4-ylene group, a naphth-1,5-ylene group, a substituted naphth-1,5-ylene group, a naphth-1,6-ylene group, a substituted naphth-1,6-ylene group, a naphth-1,7-ylene group, a substituted naphth-1,7-ylene group, a naphth-1,8-ylene group, or a substituted naphth-1,8-ylene group. In other aspects, L can be a naphth-1,3-ylene group or a substituted naphth-1,3-ylene group; alternatively, a naphth-1,4-ylene group or a substituted naphth-1,4-ylene group; alternatively, a naphth-1,5-ylene group or a substituted naphth-1,5-ylene group; alternatively, a naphth-1,6-ylene group or a substituted naphth-1,6-ylene group; alternatively, a naphth-1,7-ylene group or a substituted naphth-1,7-ylene group; or alternatively, a naphth-1,8-ylene group or a substituted naphth-1,8-ylene group. Yet, in other aspects, L can be a naphth-1,3-ylene group; alternatively, a substituted naphth-1,3-ylene group; alternatively, a naphth-1,4-ylene group; alternatively, a substituted naphth-1,4-ylene group; alternatively, a naphth-1,5-ylene group; alternatively, a substituted naphth-1,5-ylene group; alternatively, a naphth-1,6-ylene group; alternatively, a substituted naphth-1,6-ylene group; alternatively, a naphth-1,7-ylene group; alternatively, a substituted naphth-1,7-ylene group; alternatively, a naphth-1,8-ylene group; or alternatively, a substituted naphth-1,8-ylene group. The substituent(s) for a substituted arylene group in formula (IIa) can be any substituent (e.g., a $C_1$ to $C_{12}$ hydrocarbyl group, a $C_1$ to $C_8$ alkyl group, etc.) disclosed herein above, e.g., in relation to substituted aryl groups in formula (Ia).

In an aspect, L can be a di(methylene)benzene group or a substituted di(methylene)benzene group; or alternatively, a di(methylene)benzene group. In another aspect, L can be a 1,2-di(methylene)benzene group, a substituted 1,2-di(methylene)benzene group, a 1,3-di(methylene)benzene group, a substituted 1,3-di(methylene)benzene group, a 1,4-di(methylene)benzene group, or a substituted 1,4-di(methylene)benzene group; alternatively, a 1,2-di(methylene)benzene group, a 1,3-di(methylene)benzene group, or a 1,4-di(methylene)benzene group. In yet another aspect, L can be a 1,2-di(methylene)benzene group or a substituted 1,2-di(methylene)benzene group; alternatively, a 1,3-di(methylene)benzene group or a substituted 1,3-di(methylene)benzene group; alternatively, a 1,4-di(methylene)benzene group or a substituted 1,4-di(methylene)benzene group; alternatively, a 1,2-di(methylene)benzene group; alternatively, a 1,3-di(methylene)benzene group; or alternatively, a 1,4-di(methylene)benzene group. The substituent(s) for a substituted di(methylene)benzene group in formula (IIa) can be any substituent (e.g., a $C_1$ to $C_{12}$ hydrocarbyl group, a $C_1$ to $C_8$ alkyl group, etc.) disclosed herein above, e.g., in relation to substituted aryl groups in formula (Ia).

In formula (IIa), D can be a chemical group comprising at least one of nitrogen, oxygen, phosphorus, and sulfur. In some aspects, the heteroatom-containing D group can complex and/or coordinate with the metal, M. D can be a $C_1$ to $C_{36}$ group comprising at least one of nitrogen, oxygen, phosphorus, and sulfur; alternatively, a $C_1$ to $C_{24}$ group comprising at least one of nitrogen, oxygen, phosphorus, and sulfur; alternatively, a $C_1$ to $C_{18}$ group comprising at least one of nitrogen, oxygen, phosphorus, and sulfur; alternatively, a $C_1$ to $C_{10}$ group comprising at least one of nitrogen, oxygen, phosphorus, and sulfur; or alternatively, a $C_1$ to $C_5$ group comprising at least one of nitrogen, oxygen, phosphorus, and sulfur. In some aspects, the heteroatom can be oxygen; alternatively, sulfur; alternatively, nitrogen; alternatively, phosphorus; alternatively, nitrogen and oxygen; or alternatively, nitrogen and sulfur. Hence, D can contain more than one heteroatom (e.g., nitrogen and oxygen, two nitrogens, etc.). Optionally, D can contain inert heteroatoms other than nitrogen, oxygen, phosphorus, and sulfur, which do not complex and/or coordinate with the metal (e.g., halides or silicon).

In an aspect, D can be a dihydrocarbyl aminyl group, a dihydrocarbyl phosphinyl group, a hydrocarbyl etheryl group, or a hydrocarbyl sulfidyl group. In another aspect, D can be a dihydrocarbyl aminyl group; alternatively, a dihydrocarbyl phosphinyl group; alternatively, a hydrocarbyl etheryl group; or alternatively, a hydrocarbyl sulfidyl group. In these and other aspects, each hydrocarbyl group of the dihydrocarbyl aminyl group, the dihydrocarbyl phosphinyl group, the hydrocarbyl etheryl group, and the hydrocarbyl sulfidyl group can be any hydrocarbyl group disclosed herein, such as, for example, an alkyl group, an alkenyl group, a cycloalkyl group, an aryl group, or an aralkyl group; alternatively, an alkyl group; alternatively, an alkenyl group; alternatively, a cycloalkyl group; alternatively, an aryl group; or alternatively, an aralkyl group. Suitable alkyl groups, alkenyl groups, cycloalkyl groups, aryl groups, and aralkyl groups are independently disclosed herein and can be utilized without limitation to further describe D in formula (IIa).

In accordance with an aspect of the invention, D can be a dialkylaminyl group, a dicycloalkylaminyl group, a di(substituted cycloalkyl)aminyl group, an N-(alkyl)-N-(cycloalkyl)aminyl group, an N-(alkyl)-N-(substituted cycloalkyl)aminyl group, an N-(cycloalkyl)-N-(substituted cycloalkyl)aminyl group, a diarylaminyl group, a di(substituted aryl)aminyl group, an N-aryl N-(substituted aryl)aminyl group, an N-alkyl N-arylaminyl group, an N-alkyl N-(substituted aryl)aminyl group, a dialkylphosphinyl group, a dicycloalkylphosphinyl group, a di(substituted cycloalkyl) phosphinyl group), an N (alkyl)-N-(cycloalkyl)phosphinyl group, an N-(alkyl)-N-(substituted cycloalkyl)phosphinyl group, an N-(cycloalkyl)-N-(substituted cycloalkyl)phosphinyl group, a diarylphosphinyl group, a di(substituted aryl) phosphinyl group, a P-aryl P-(substituted aryl)phosphinyl group, a P-alkyl P-arylphosphinyl group, a P-alkyl P-(substituted aryl)phosphinyl group, an alkoxy group, an aroxy group, a substituted aroxy group, an alkylsulfidyl group, an arylsulfidyl group, a substituted arylsulfidyl group, a furanyl group, a substituted furanyl group, a thienyl group, a substituted thienyl group, a tetrahydrofuranyl group, a substituted tetrahydrofuranyl group, a thiophanyl group, a substituted thiophanyl group, a pyridinyl group, a substituted pyridinyl group, a morphilinyl group, a substituted morphilinyl group, a pyranyl group, a substituted pyranyl group, a tetrahydropyranyl group, a substituted tetrahydropyranyl group, a quinolinyl group, a substituted quinolinyl group, a pyrrolyl group, a substituted pyrrolyl group, a pyrrolidinyl group, a substituted pyrrolidinyl group, a piperidinyl group, or a substituted piperidinyl group. For any of the cyclic or heterocyclic groups, L can bond to any position of the respective ring structure that is consistent with the rules of chemical valence. For any of the substituted groups, the substituent(s) can be any substituent (e.g., a $C_1$ to $C_{12}$ hydrocarbyl group, a $C_1$ to $C_8$ alkyl group, etc.) disclosed herein, such as above in relation to substituted groups pertaining to formula (Ia). Similarly, the alkyl, cycloalkyl, aryl, and aralkyl groups can be any alkyl, cycloalkyl, aryl, and aralkyl, groups disclosed herein.

In another aspect, D can be a dialkylaminyl group, a dicycloalkylaminyl group, a di(substituted cycloalkyl)aminyl group, an N-(alkyl)-N-(cycloalkyl)aminyl group, an N-(alkyl)-N-(substituted cycloalkyl)aminyl group, an N-(cycloalkyl)-N-(substituted cycloalkyl)aminyl group, a diarylaminyl group, a di(substituted aryl)aminyl group, an N-aryl N-(substituted aryl)aminyl group, an N-alkyl N-arylaminyl group, or an N-alkyl N-(substituted aryl)aminyl group. In another aspect, D can be a dialkylphosphinyl group, a dicycloalkylphosphinyl group, a di(substituted cycloalkyl)phosphinyl group), an N (alkyl)-N-(cycloalkyl)phosphinyl group, an N-(alkyl)-N-(substituted cycloalkyl)phosphinyl group, an N-(cycloalkyl)-N-(substituted cycloalkyl)phosphinyl group, a diarylphosphinyl group, a di(substituted aryl)phosphinyl group, a P-aryl P-(substituted aryl)phosphinyl group, a P-alkyl P-arylphosphinyl group, or a P-alkyl P-(substituted aryl)phosphinyl group. In another aspect, D can be an alkoxy group, an aroxy group, or a substituted aroxy group. Yet, in another aspect, D can be an alkylsulfidyl group, an arylsulfidyl group, or a substituted arylsulfidyl group. In still another aspect, D can be a furanyl group, a substituted furanyl group, a thienyl group, a substituted thienyl group, a tetrahydrofuranyl group, a substituted tetrahydrofuranyl group, a thiophanyl group, a substituted thiophanyl group, a pyridinyl group, a substituted pyridinyl group, a morphilinyl group, a substituted morphilinyl group, a pyranyl group, a substituted pyranyl group, a tetrahydropyranyl group, a substituted tetrahydropyranyl group, a quinolinyl group, a substituted quinolinyl group, a pyrrolyl group, a substituted pyrrolyl group, a pyrrolidinyl group, a substituted pyrrolidinyl group, a piperidinyl group, or a substituted piperidinyl group.

In another aspect, D can be a dialkylaminyl group; alternatively, a dicycloalkylaminyl group; alternatively, a di(substituted cycloalkyl)aminyl group; alternatively, an N-(alkyl)-N-(cycloalkyl)aminyl group; alternatively, an N-(alkyl)-N-(substituted cycloalkyl)aminyl group; alternatively, an N-(cycloalkyl)-N-(substituted cycloalkyl)aminyl group; alternatively, a diarylaminyl group; alternatively, a di(substituted aryl)aminyl group; alternatively, an N-aryl N-(substituted aryl)aminyl group; alternatively, an N-alkyl N-arylaminyl group; alternatively, an N-alkyl N-(substituted aryl)aminyl group; alternatively, a dialkylphosphinyl group; alternatively, a dicycloalkylphosphinyl group; alternatively, a di(substituted cycloalkyl)phosphinyl group); alternatively, an N (alkyl)-N-(cycloalkyl)phosphinyl group; alternatively, an N-(alkyl)-N-(substituted cycloalkyl)phosphinyl group; alternatively, an N-(cycloalkyl)-N-(substituted cycloalkyl)phosphinyl group; alternatively, a diarylphosphinyl group; alternatively, a di(substituted aryl)phosphinyl group; alternatively, a P-aryl P-(substituted aryl)phosphinyl group; alternatively, a P-alkyl P-arylphosphinyl group; alternatively, a P-alkyl P-(substituted aryl)phosphinyl group; alternatively, an alkoxy group; alternatively, an aroxy group; alternatively, a substituted aroxy group; alternatively, an alkylsulfidyl group; alternatively, an arylsulfidyl group; alternatively, a substituted arylsulfidyl group; alternatively, a furanyl group; alternatively, a substituted furanyl group; alternatively, a thienyl group; alternatively, a substituted thienyl group; alternatively, a tetrahydrofuranyl group; alternatively, a substituted tetrahydrofuranyl group; alternatively, a thiophanyl group; alternatively, a substituted thiophanyl group; alternatively, a pyridinyl group; alternatively, a substituted pyridinyl group; alternatively, a morphilinyl group; alternatively, a substituted morphilinyl group; alternatively, a pyranyl group; alternatively, a substituted pyranyl group; alternatively, a tetrahydropyranyl group; alternatively, a substituted tetrahydropyranyl group; alternatively, a quinolinyl group; alternatively, a substituted quinolinyl group; alternatively, a pyrrolyl group; alternatively, a substituted pyrrolyl group; alternatively, a pyrrolidinyl group; alternatively, a substituted pyrrolidinyl group; alternatively, a piperidinyl group; or alternatively, a substituted piperidinyl group.

In an aspect, D in formula (IIa) can have Structure Q1, Structure Q2, Structure Q3, Structure Q4, Structure Q5, Structure Q6, Structure Q7, Structure Q8, Structure Q9, Structure Q10, Structure Q11, Structure Q12, Structure Q13, Structure Q14, Structure Q15, Structure Q16, Structure Q17, Structure Q18, Structure Q19, Structure Q20, Structure Q21, or Structure Q22, and these structures are illustrated in the table below.

| Table of Structures Q1 to Q22 | |
|---|---|
| —OR$^{q1}$ | Structure Q1 |
| —SR$^{q2}$ | Structure Q2 |
| —NR$^{q3}$R$^{q4}$ | Structure Q3 |
| —PR$^{q5}$R$^{q6}$ | Structure Q4 |
| 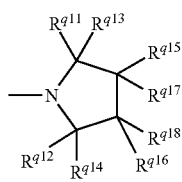 | Structure Q5 |
| 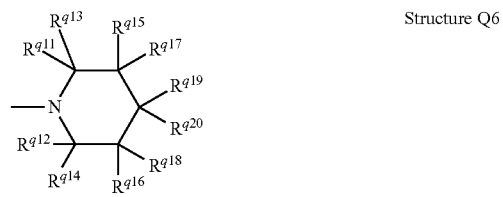 | Structure Q6 |
| 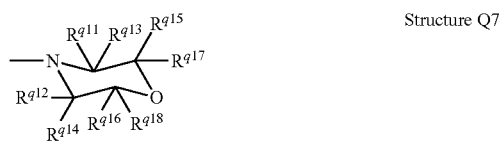 | Structure Q7 |
| 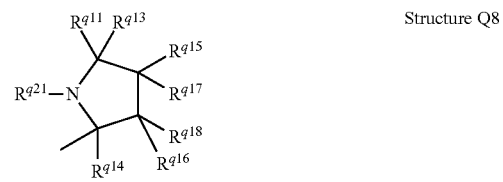 | Structure Q8 |
| 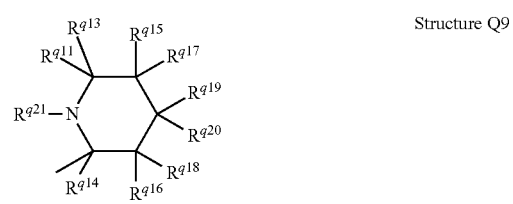 | Structure Q9 |
| 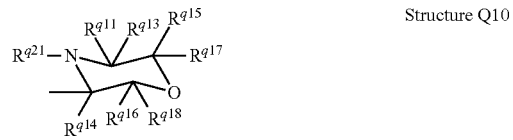 | Structure Q10 |
|  | Structure Q11 |
|  | Structure Q12 |
| 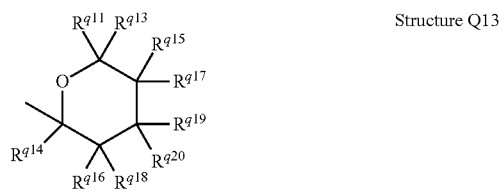 | Structure Q13 |
| 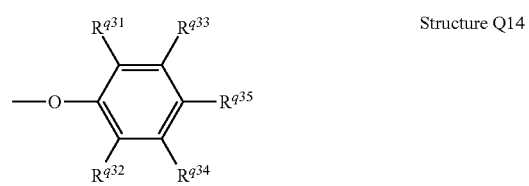 | Structure Q14 |

Table of Structures Q1 to Q22

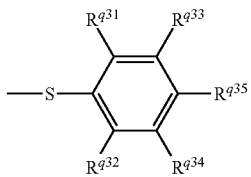
Structure Q15

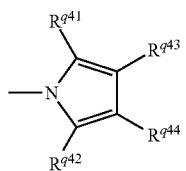
Structure Q16

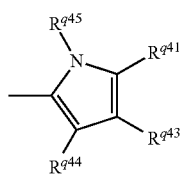
Structure Q17

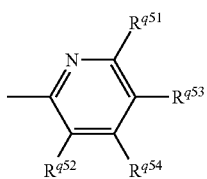
Structure Q18

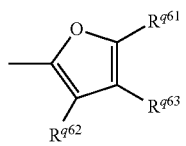
Structure Q19

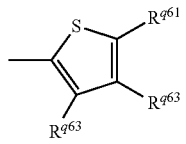
Structure Q20

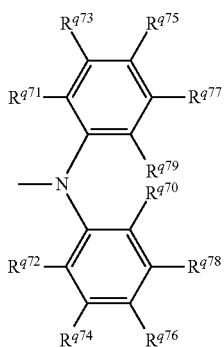
Structure Q21

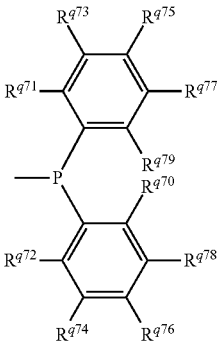
Structure Q22

In another aspect, D can have Structure Q1, Structure Q2, Structure Q3, Structure Q4, Structure Q5, Structure Q6, Structure Q7, Structure Q8, Structure Q9, Structure Q10, Structure Q11, Structure Q12, Structure Q13, Structure Q16, Structure Q17, Structure Q18, Structure Q19, or Structure Q20. In yet another aspect, D can have Structure Q1, Structure Q2, Structure Q3, or Structure Q4; alternatively, Structure Q1 or Structure Q2; alternatively, Structure Q3 or Structure Q4; alternatively, Structure Q5 or Structure Q6; alternatively, Structure Q7 or Structure Q10; alternatively, Structure Q8 or Structure Q9; alternatively, Structure Q11 or Structure Q12; alternatively, Structure Q11 or Structure Q13; alternatively, Structure Q19 or Structure Q20; alternatively, Structure Q1; alternatively, Structure Q2; alternatively, Structure Q3; alternatively, Structure Q4; alternatively, Structure Q5; alternatively, Structure Q6; alternatively, Structure Q7; alternatively, Structure Q8; alternatively, Structure Q9; alternatively, Structure Q10; alternatively, Structure Q11; alternatively, Structure Q12; alternatively, Structure 13; alternatively, Structure Q16; alternatively, Structure Q17; alternatively, Structure Q18; alternatively, Structure Q19; or alternatively, Structure Q20. In still another aspect, D can have Structure Q14, Structure Q15, Structure Q21, or Structure Q22; alternatively, Structure Q14 or Structure Q15; alternatively, Structure Q21 or Structure Q22; alternatively, Structure Q14; alternatively, Structure Q15; alternatively, Structure Q21; or alternatively, Structure Q22.

In some aspects, $R^{q1}$, $R^{q2}$, $R^{q3}$, $R^{q4}$, $R^{q5}$, and $R^{q6}$ within Structure Q1, Structure Q2, Structure Q3, or Structure Q4 can be any $C_1$ to $C_{18}$ hydrocarbyl group, $C_1$ to $C_{15}$ hydrocarbyl group, $C_1$ to $C_{10}$ hydrocarbyl group, or $C_1$ to $C_5$ hydrocarbyl group disclosed herein. For instance, $R^{q1}$, $R^{q2}$, $R^{q3}$, $R^{q4}$, $R^{q5}$, and $R^{q6}$ within Structure Q1, Structure Q2, Structure Q3, or Structure Q4 independently can be any $C_1$ to $C_{18}$ alkyl group, $C_4$ to $C_{18}$ cycloalkyl group, $C_6$ to $C_{18}$ aryl group, $C_7$ to $C_{18}$ aralkyl group, or $C_2$ to $C_{18}$ alkenyl group disclosed herein, or any $C_1$ to $C_5$ alkyl group, $C_4$ to $C_8$ cycloalkyl group, $C_6$ to $C_{10}$ aryl group, $C_7$ to $C_{10}$ aralkyl group, or $C_3$ to $C_8$ alkenyl group (e.g., propenyl, butenyl, pentenyl, etc.) disclosed herein. In a similar manner, $R^{q21}$ in Structure Q8, Structure Q9, and Structure Q10 can be any $C_1$ to $C_{18}$ hydrocarbyl group (e.g., alkyl group, cycloalkyl group, aryl group, aralkyl group, alkenyl group, etc.) disclosed herein.

In some aspects, each $R^{q11}$, $R^{q12}$, $R^{q13}$, $R^{q14}$, $R^{q15}$, $R^{q16}$, $R^{q17}$, $R^{q18}$, $R^{q19}$, $R^{q20}$, $R^{q31}$, $R^{q32}$, $R^{q33}$, $R^{q34}$, $R^{q35}$, $R^{q41}$, $R^{q42}$, $R^{q43}$, $R^{q44}$, $R^{q45}$, $R^{q51}$, $R^{q52}$, $R^{q53}$, $R^{q54}$, $R^{q61}$, $R^{q62}$, $R^{q63}$, $R^{q71}$, $R^{q72}$, $R^{q73}$, $R^{q74}$, $R^{q75}$, $R^{q76}$, $R^{q77}$, $R^{q78}$, $R^{q79}$, and/or $R^{q80}$ of Structures Q5-Q22 independently can be hydrogen or any $C_1$ to $C_{18}$ hydrocarbyl group disclosed herein. Accordingly, each $R^{q11}$-$R^{q20}$, $R^{q31}$-$R^{q35}$, $R^{q41}$-$R^{q45}$, $R^{q51}$-$R^{q54}$, $R^{q61}$-$R^{q63}$, and/or $R^{q71}$-$R^{q80}$ non-hydrogen substituent in Structures Q5-Q22 can be any alkyl group, cycloalkyl group, aryl group, aralkyl group, alkenyl group, etc., disclosed herein.

In particular aspects contemplated herein, D in formula (IIa) can be —N(CH$_3$)$_2$, —P(CH$_3$)$_2$, —N(CH$_2$CH$_3$)$_2$, —P(CH$_2$CH$_3$)$_2$, —N(Ph)$_2$, —P(Ph)$_2$, —OCH$_3$, —SCH$_3$, —OCH$_2$CH$_3$, —SCH$_2$CH$_3$, —OPh, or —SPh. For instance, D can be —N(CH$_3$)$_2$, —P(CH$_3$)$_2$, —N(CH$_2$CH$_3$)$_2$, —P(CH$_2$CH$_3$)$_2$, —N(Ph)$_2$, or —P(Ph)$_2$; alternatively, —OCH$_3$, —SCH$_3$, —OCH$_2$CH$_3$, —SCH$_2$CH$_3$, —OPh, or —SPh; alternatively, —N(CH$_3$)$_2$, —P(CH$_3$)$_2$, —N(CH$_2$CH$_3$)$_2$, —P(CH$_2$CH$_3$)$_2$; alternatively, —N(Ph)$_2$, or —P(Ph)$_2$; alternatively, —OCH$_3$, —SCH$_3$, —OCH$_2$CH$_3$, or —SCH$_2$CH$_3$; or alternatively, —OPh or —SPh.

In another embodiment of this invention, the N,N-bis[2-hydroxidebenzyl]amine compound can have the formula:

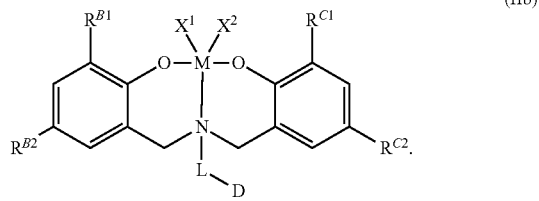

(IIb)

Within formula (IIb), M, $X^1$, $X^2$, L, D, $R^{B1}$, $R^{B2}$, $R^{C1}$, and $R^{C2}$ are independent elements of the N,N-bis[2-hydroxidebenzyl]amine compound. Accordingly, the N,N-bis[2-hydroxidebenzyl]amine compound having formula (IIb) can be described using any combination of M, $X^1$, $X^2$, L, D, $R^{B1}$, $R^{B2}$, $R^{C1}$, and $R^{C2}$ disclosed herein.

The selections for M, $X^1$, $X^2$, L, and D in formula (IIb) are the same as those described herein above for formula (IIa). $R^{B1}$, $R^{B2}$, $R^{C1}$, and $R^{C2}$ independently can be a halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group, and these groups can be any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group described herein (e.g., as pertaining to $R^B$ and $R^C$ in formula (Ia)).

In one aspect, for example, $R^{B1}$, $R^{B2}$, $R^{C1}$, and $R^{C2}$ independently can be a methyl group, ethyl group, propyl group, butyl group (e.g., t-Bu), pentyl group, hexyl group, propenyl group, butenyl group, pentenyl group, hexenyl group, phenyl group, tolyl group, benzyl group, trimethylsilyl group, triisopropylsilyl group, triphenylsilyl group, allyldimethylsilyl group, CF$_3$, or Cl. In another aspect, $R^{B1}$, $R^{B2}$, $R^{C1}$, and $R^{C2}$ independently can be a methyl group, ethyl group, propyl group, butyl group, pentyl group, hexyl group, propenyl group, butenyl group, pentenyl group, hexenyl group, phenyl group, tolyl group, or benzyl group. In yet another aspect, at least one of $R^{B1}$, $R^{B2}$, $R^{C1}$, and $R^{C2}$ (or alternatively, each of $R^{B1}$, $R^{B2}$, $R^{C1}$, and $R^{C2}$) can be a methyl group; alternatively, an ethyl group; alternatively, a propyl group; alternatively, a butyl group; alternatively, a pentyl group; alternatively, a hexyl group; alternatively, a propenyl group; alternatively, a butenyl group; alternatively, a pentenyl group; alternatively, a hexenyl group; alternatively, a phenyl group; alternatively, a tolyl group; alternatively, a benzyl group; alternatively, a trimethylsilyl group; alternatively, a triisopropylsilyl group; alternatively, a triphenylsilyl group; alternatively, an allyldimethylsilyl group; alternatively, CF$_3$; or alternatively, Cl. In these and other aspects, L in formula (IIb) can be a $C_1$ to $C_{18}$ hydrocarbylene group, examples of which can include, but are not limited to, a $C_1$ to $C_4$ alkylene group, a $C_5$ to $C_8$ cycloalkylene group, a $C_6$ to $C_8$ arylene group, a $C_7$ to $C_8$ aralkylene group, and the like; and D can be a chemical group comprising at least one of nitrogen, oxygen, phosphorus, and sulfur, examples of which can include, but are not limited to, —N(CH$_3$)$_2$, —P(CH$_3$)$_2$, —N(CH$_2$CH$_3$)$_2$, —P(CH$_2$CH$_3$)$_2$, —N(Ph)$_2$, —P(Ph)$_2$, —OCH$_3$, —SCH$_3$, —OCH$_2$CH$_3$, —SCH$_2$CH$_3$, —OPh, —SPh, and the like.

Figure 2:
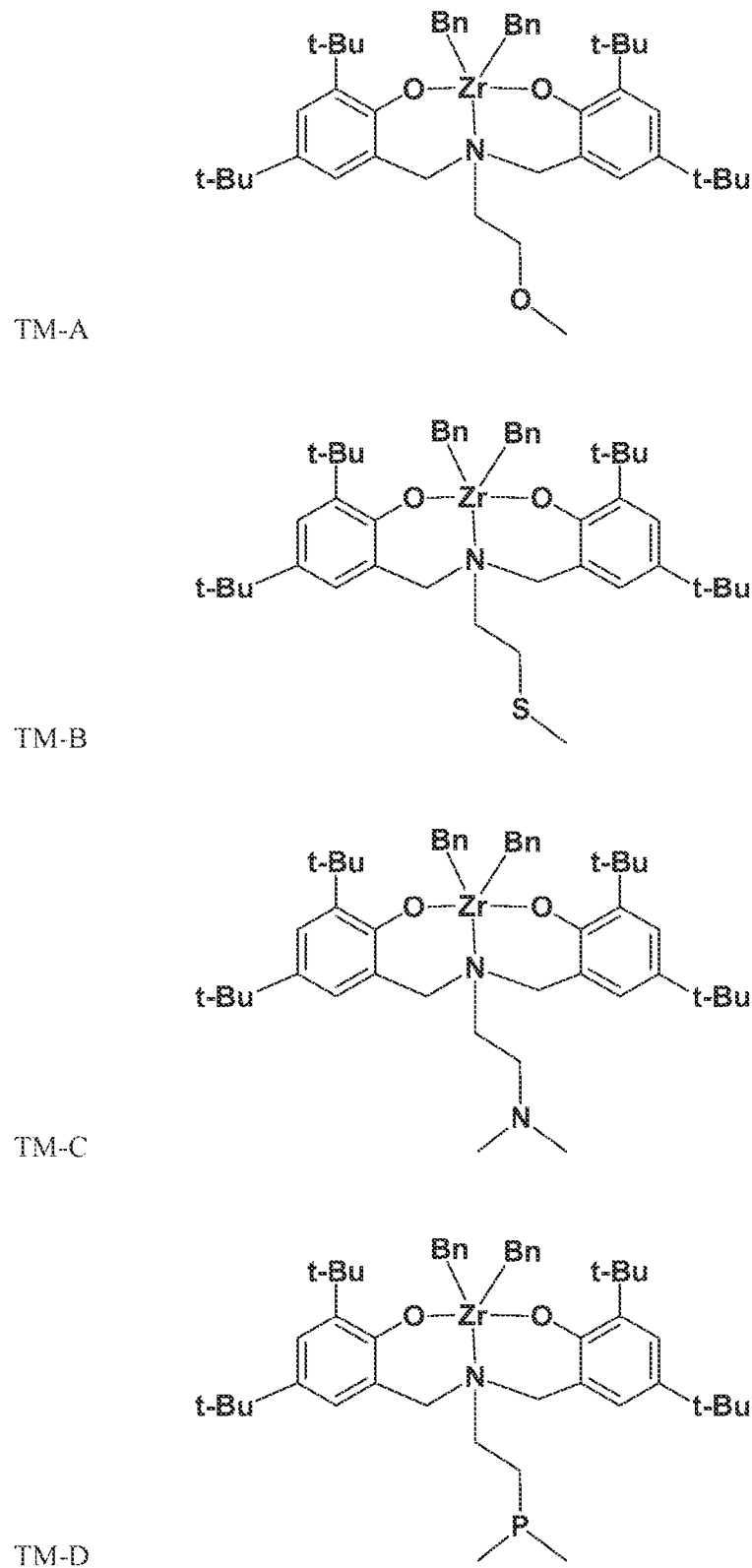
FIG. 2 presents the structures and abbreviations for compounds TM-A, TM-B, TM-C, and TM-D discussed herein.

Illustrative and non-limiting examples of N,N-bis[2-hydroxidebenzyl]amine compounds having formula (IIa) and formula (IIb) can include, but are not limited to, compounds TM-A, TM-B, TM-C, and TM-D illustrated in FIG. 2.

Representative procedures for synthesizing compounds having formula (IIa) and formula (IIb) can be found in U.S. Pat. Nos. 6,333,423 and 6,596,827, the disclosures of which are incorporated herein by reference in their entirety. Using analogous synthesis schemes, transition metal complexes similar to TM-A, TM-B, TM-C, and TM-D, but with monoanionic ligands other than benzyl (e.g., halide, hydrocarbylaminyl, hydrocarbylsilyl, other hydrocarbyl, etc.), and/or with substituents other than tert-butyl (e.g., halide, hydrocarboxy, hydrocarbylsilyl, other hydrocarbyl, etc.), and/or with different L and D groups, can be derived.

In another embodiment of this invention, the N,N-bis[2-hydroxidebenzyl]amine compound can have the formula:

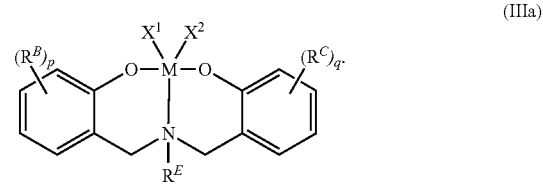

(IIIa)

Within formula (IIIa), M, $X^1$, $X^2$, $R^B$, $R^C$, p, q, and $R^E$ are independent elements of the N,N-bis[2-hydroxidebenzyl]amine compound. Accordingly, the N,N-bis[2-hydroxidebenzyl]amine compound having formula (IIIa) can be described using any combination of M, $X^1$, $X^2$, $R^B$, $R^C$, p, q, and $R^E$ disclosed herein.

The selections for M, $X^1$, $X^2$, $R^B$, $R^C$, p, and q in formula (IIIa) are the same as those described herein above for formula (Ia). For instance, M can be Ti, Zr, or Hf; alternatively, M can be Ti; alternatively, M can be Zr; or alternatively, M can be Hf. $X^1$ and $X^2$ in formula (IIIa) independently can be any monoanionic ligand disclosed herein, and this includes, but is not limited to, H, BH$_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, —OBR$^1$$_2$, or —OSO$_2$R$^1$, wherein R$^1$ is a $C_1$ to $C_{36}$ hydrocarbyl group. In some aspects, it is contemplated that $X^1$ and $X^2$ independently can be a $C_1$ to $C_{18}$ hydrocarbyl group, a $C_1$ to $C_{18}$ hydrocarboxy group, a $C_1$ to $C_{18}$ hydrocarbylaminyl group, a $C_1$ to $C_{18}$ hydrocarbylsilyl group, or a $C_1$ to $C_{18}$ hydrocarbylaminylsilyl group, while in other aspects, $X^1$ and $X^2$ independently can be a halide or a $C_1$ to $C_{18}$ hydrocarbyl group. In formula (IIIa), each $R^B$ and/or $R^C$ independently can be any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group disclosed herein. For example, each $R^B$ and/or $R^C$ independently can be Cl, CF$_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, a naphthyl group, a trimethylsilyl group, a triisopropylsilyl group, a triphenylsilyl group, or an allyldimethylsilyl group. The integers, p and q, independently can be 0, 1, 2, 3, or 4, such as, for instance, p can be 0, 1, or 2, and q can be 0, 1, or 2.

$R^E$ in formula (IIIa) can be any alkenyl group disclosed herein, for instance, any $C_2$ to $C_{36}$ alkenyl group, any $C_2$ to $C_{18}$ alkenyl group, any $C_3$ to $C_{12}$ alkenyl group, any $C_3$ to $C_8$ alkenyl group, or any $C_3$ to $C_6$ alkenyl group disclosed herein. Accordingly, in one aspect, the alkenyl group which can be $R^E$ in formula (IIIa) can be an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. In another aspect, $R^E$ in formula (IIIa) can be an ethenyl group, a propenyl group, a butenyl group, a pentenyl group, a hexenyl group, a heptenyl group, an octenyl group, a nonenyl group, or a decenyl group, while in yet another aspect, $R^E$ in formula (IIIa) can be an ethenyl group, a propenyl group, a butenyl group, a pentenyl group, or a hexenyl group. For example, $R^E$ can be an ethenyl group; alternatively, a propenyl group; alternatively, a butenyl group; alternatively, a pentenyl group; or alternatively, a hexenyl group. In still another aspect, $R^E$ can be a terminal alkenyl group, such as a $C_3$ to $C_{18}$ terminal alkenyl group, a $C_3$ to $C_{12}$ terminal alkenyl group, or a $C_3$ to $C_8$ terminal alkenyl group.

In another embodiment of this invention, the N,N-bis[2-hydroxidebenzyl]amine compound can have the formula:

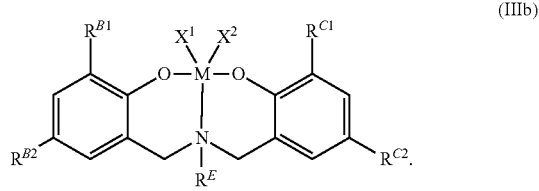

(IIIb)

Within formula (IIIb), M, $X^1$, $X^2$, $R^E$, $R^{B1}$, $R^{B2}$, $R^{C1}$, and $R^{C2}$ are independent elements of the N,N-bis[2-hydroxidebenzyl]amine compound. Accordingly, the N,N-bis[2-hydroxidebenzyl]amine compound having formula (IIIb) can be described using any combination of M, $X^1$, $X^2$, $R^E$, $R^{B1}$, $R^{B2}$, $R^{C1}$, and $R^{C2}$ disclosed herein.

The selections for M, $X^1$, $X^2$, and $R^E$ in formula (IIIb) are the same as those described herein above for formula (IIIa), while the selections for $R^{B1}$, $R^{B2}$, $R^{C1}$, and $R^{C2}$ are the same as those described herein above for formula (Ib). For example, M in formula (IIIb) can be Ti, Zr, or Hf; $X^1$ and $X^2$ independently can be any monoanionic ligand disclosed herein; and $R^E$ can be any alkenyl group disclosed herein (e.g., a propenyl group, a butenyl group, a pentenyl group, a hexenyl group, a heptenyl group, an octenyl group, etc.). In these and other aspects, $R^{B1}$, $R^{B2}$, $R^{C1}$, and $R^{C2}$ in formula (IIIb) independently can be any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group disclosed herein, examples of which can include, but are not limited to, Cl, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, a naphthyl group, a trimethylsilyl group, a triisopropylsilyl group, a triphenylsilyl group, or an allyldimethylsilyl group, and the like.

Illustrative and non-limiting examples of N,N-bis[2-hydroxidebenzyl]amine compounds having formula (IIIa) and formula (IIIb) can include, but are not limited to, compounds TM-1 and TM-2 illustrated in FIG. 1.

Methods of making transition metal complexes having formula (IIIa) and formula (IIIb) also are provided herein. Examples 1-8 that follow provide representative procedures for synthesizing compounds having formula (IIIa) and formula (IIIb), or for synthesizing precursor compounds useful in the subsequent synthesis of compounds having formula (IIIa) and formula (IIIb) Using analogous synthesis schemes to those provided herein, transition metal complexes similar to TM-1 and TM-2, but with monoanionic ligands other than benzyl (e.g., halide, hydrocarbylaminyl, hydrocarbylsilyl, other hydrocarbyl, etc.), and/or with substituents other than tert-butyl (e.g., halide, hydrocarboxy, hydrocarbylsilyl, other hydrocarbyl, etc.), and/or with a different alkenyl group, can be derived.

Activator-Supports

The present invention encompasses various catalyst compositions containing an activator-support. In one embodiment, the activator-support can comprise a chemically-treated solid oxide. Alternatively, in another embodiment, the activator-support can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or combinations thereof.

Generally, chemically-treated solid oxides exhibit enhanced acidity as compared to the corresponding untreated solid oxide compound. The chemically-treated solid oxide also can function as a catalyst activator as compared to the corresponding untreated solid oxide. While the chemically-treated solid oxide can activate a transition metal complex in the absence of co-catalysts, it is not necessary to eliminate co-catalysts from the catalyst composition. The activation function of the activator-support can enhance the activity of catalyst composition as a whole, as compared to a catalyst composition containing the corresponding untreated solid oxide. However, it is believed that the chemically-treated solid oxide can function as an activator, even in the absence of organoaluminum compounds, aluminoxanes, organoboron or organoborate compounds, ionizing ionic compounds, and the like.

The chemically-treated solid oxide can comprise a solid oxide treated with an electron-withdrawing anion. While not intending to be bound by the following statement, it is believed that treatment of the solid oxide with an electron-withdrawing component augments or enhances the acidity of the oxide. Thus, either the activator-support exhibits Lewis or Brønsted acidity that is typically greater than the Lewis or Brønsted acid strength of the untreated solid oxide, or the activator-support has a greater number of acid sites than the untreated solid oxide, or both. One method to quantify the acidity of the chemically-treated and untreated solid oxide materials can be by comparing the polymerization activities of the treated and untreated oxides under acid catalyzed reactions.

Chemically-treated solid oxides of this invention generally can be formed from an inorganic solid oxide that exhibits Lewis acidic or Brønsted acidic behavior and has a relatively high porosity. The solid oxide can be chemically-treated with an electron-withdrawing component, typically an electron-withdrawing anion, to form an activator-support.

According to one aspect of the present invention, the solid oxide used to prepare the chemically-treated solid oxide can have a pore volume greater than about 0.1 cc/g. According to another aspect of the present invention, the solid oxide can have a pore volume greater than about 0.5 cc/g. According to yet another aspect of the present invention, the solid oxide can have a pore volume greater than about 1.0 cc/g.

In another aspect, the solid oxide can have a surface area of from about 100 to about 1000 $m^2/g$. In yet another aspect, the solid oxide can have a surface area of from about 200 to about 800 $m^2/g$. In still another aspect of the present invention, the solid oxide can have a surface area of from about 250 to about 600 $m^2/g$.

The chemically-treated solid oxide can comprise a solid inorganic oxide comprising oxygen and one or more elements selected from Group 2, 3, 4, 5, 6, 7, 8, 9, 10, 11, 12, 13, 14, or 15 of the periodic table, or comprising oxygen and one or more elements selected from the lanthanide or actinide elements (See: Hawley's Condensed Chemical Dictionary, $11^{th}$ Ed., John Wiley & Sons, 1995; Cotton, F. A., Wilkinson, G., Murillo, C. A., and Bochmann, M., Advanced Inorganic Chemistry, $6^{th}$ Ed., Wiley-Interscience, 1999). For example, the inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used to form the chemically-treated solid oxide can include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. For example, the solid oxide can comprise silica, alumina, silica-alumina, silica-coated alumina, aluminum phosphate, aluminophosphate, heteropolytungstate, titania, zirconia, magnesia, boria, zinc oxide, mixed oxides thereof, or any combination thereof.

The solid oxide of this invention encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Examples of mixed oxides that can be used in the activator-support of the present invention, either singly or in combination, can include, but are not limited to, silica-alumina, silica-titania, silica-zirconia, zeolites, various clay minerals, alumina-titania, alumina-zirconia, zinc-aluminate, alumina-boria, silica-boria, aluminophosphate-silica, titania-zirconia, and the like. The solid oxide of this invention also encompasses oxide materials such as silica-coated alumina, as described in U.S. Pat. No. 7,884,163, the disclosure of which is incorporated herein by reference in its entirety.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect of the present invention, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, and the like, including mixtures and combinations thereof. In addition, other ionic or non-ionic compounds that serve as sources for these electron-withdrawing anions also can be employed in the present invention. It is contemplated that the electron-withdrawing anion can be, or can comprise, fluoride, chloride, bromide, phosphate, triflate, bisulfate, or sulfate, and the like, or any combination thereof, in some aspects of this invention. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof.

Thus, for example, the activator-support (e.g., chemically-treated solid oxide) used in the catalyst compositions of the present invention can be, or can comprise, fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In one aspect, the activator-support can be, or can comprise, fluorided alumina, sulfated alumina, fluorided silica-alumina, sulfated silica-alumina, fluorided silica-coated alumina, sulfated silica-coated alumina, phosphated silica-coated alumina, and the like, or any combination thereof. In another aspect, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; or alternatively, fluorided silica-coated alumina.

When the electron-withdrawing component comprises a salt of an electron-withdrawing anion, the counterion or cation of that salt can be selected from any cation that allows the salt to revert or decompose back to the acid during calcining. Factors that dictate the suitability of the particular salt to serve as a source for the electron-withdrawing anion can include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion can include, but are not limited to, ammonium, trialkyl ammonium, tetraalkyl ammonium, tetraalkyl phosphonium, $H^+$, $[H(OEt_2)_2]^+$, and the like.

Further, combinations of one or more different electron-withdrawing anions, in varying proportions, can be used to tailor the specific acidity of the activator-support to the desired level. Combinations of electron-withdrawing components can be contacted with the oxide material simultaneously or individually, and in any order that affords the desired chemically-treated solid oxide acidity. For example, one aspect of this invention can employ two or more electron-withdrawing anion source compounds in two or more separate contacting steps.

Thus, a process by which a chemically-treated solid oxide can be prepared is as follows: a selected solid oxide, or combination of solid oxides, can be contacted with a first electron-withdrawing anion source compound to form a first mixture; this first mixture can be calcined and then contacted with a second electron-withdrawing anion source compound to form a second mixture; the second mixture then can be calcined to form a treated solid oxide. In such a process, the first and second electron-withdrawing anion source compounds can be either the same or different compounds.

According to another aspect of the present invention, the chemically-treated solid oxide can comprise a solid inorganic oxide material, a mixed oxide material, or a combination of inorganic oxide materials, that is chemically-treated with an electron-withdrawing component, and optionally treated with a metal source, including metal salts, metal ions, or other metal-containing compounds. Non-limiting examples of the metal or metal ion can include zinc, nickel, vanadium, titanium, silver, copper, gallium, tin, tungsten, molybdenum, zirconium, and the like, or combinations thereof. Examples of chemically-treated solid oxides that contain a metal or metal ion can include, but are not limited to, chlorided zinc-impregnated alumina, fluorided titanium-impregnated alumina, fluorided zinc-impregnated alumina, chlorided zinc-impregnated silica-alumina, fluorided zinc-impregnated silica-alumina, sulfated zinc-impregnated alumina, chlorided zinc aluminate, fluorided zinc aluminate, sulfated zinc aluminate, silica-coated alumina treated with hexafluorotitanic acid, silica-coated alumina treated with zinc and then fluorided, and the like, or any combination thereof.

Any method of impregnating the solid oxide material with a metal can be used. The method by which the oxide is contacted with a metal source, typically a salt or metal-containing compound, can include, but is not limited to, gelling, co-gelling, impregnation of one compound onto another, and the like. If desired, the metal-containing compound can be added to or impregnated into the solid oxide in solution form, and subsequently converted into the supported metal upon calcining. Accordingly, the solid inorganic oxide can further comprise a metal selected from zinc, titanium, nickel, vanadium, silver, copper, gallium, tin, tungsten, molybdenum, and the like, or combinations of these metals. For example, zinc often can be used to impregnate the solid oxide because it can provide improved catalyst activity at a low cost.

The solid oxide can be treated with metal salts or metal-containing compounds before, after, or at the same time that the solid oxide is treated with the electron-withdrawing anion. Following any contacting method, the contacted mixture of solid compound, electron-withdrawing anion, and the metal ion can be calcined. Alternatively, a solid oxide material, an electron-withdrawing anion source, and the metal salt or metal-containing compound can be contacted and calcined simultaneously.

Various processes can be used to form the chemically-treated solid oxide useful in the present invention. The chemically-treated solid oxide can comprise the contact product of one or more solid oxides with one or more electron-withdrawing anion sources. It is not required that the solid oxide be calcined prior to contacting the electron-withdrawing anion source. Typically, the contact product can be calcined either during or after the solid oxide is contacted with the electron-withdrawing anion source. The solid oxide can be calcined or uncalcined. Various processes to prepare solid oxide activator-supports that can be employed in this invention have been reported. For example, such methods are described in U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, and 6,750,302, the disclosures of which are incorporated herein by reference in their entirety.

According to one aspect of the present invention, the solid oxide material can be chemically-treated by contacting it with an electron-withdrawing component, typically an electron-withdrawing anion source. Further, the solid oxide material optionally can be chemically treated with a metal ion, and then calcined to form a metal-containing or metal-impregnated chemically-treated solid oxide. According to another aspect of the present invention, the solid oxide material and electron-withdrawing anion source can be contacted and calcined simultaneously.

The method by which the oxide is contacted with the electron-withdrawing component, typically a salt or an acid of an electron-withdrawing anion, can include, but is not limited to, gelling, co-gelling, impregnation of one compound onto another, and the like. Thus, following any contacting method, the contacted mixture of the solid oxide, electron-withdrawing anion, and optional metal ion, can be calcined.

The solid oxide activator-support (i.e., chemically-treated solid oxide) thus can be produced by a process comprising:

1) contacting a solid oxide (or solid oxides) with an electron-withdrawing anion source compound (or compounds) to form a first mixture; and 2) calcining the first mixture to form the solid oxide activator-support.

According to another aspect of the present invention, the solid oxide activator-support (chemically-treated solid oxide) can be produced by a process comprising:

1) contacting a solid oxide (or solid oxides) with a first electron-withdrawing anion source compound to form a first mixture;

2) calcining the first mixture to produce a calcined first mixture;

3) contacting the calcined first mixture with a second electron-withdrawing anion source compound to form a second mixture; and 4) calcining the second mixture to form the solid oxide activator-support.

According to yet another aspect of the present invention, the chemically-treated solid oxide can be produced or formed by contacting the solid oxide with the electron-withdrawing anion source compound, where the solid oxide compound is calcined before, during, or after contacting the electron-withdrawing anion source, and where there is a substantial absence of aluminoxanes, organoboron or organoborate compounds, and ionizing ionic compounds.

Calcining of the treated solid oxide generally can be conducted in an ambient atmosphere, typically in a dry ambient atmosphere, at a temperature from about 200° C. to about 900° C., and for a time of about 1 minute to about 100 hours. Calcining can be conducted at a temperature of from about 300° C. to about 800° C., or alternatively, at a temperature of from about 400° C. to about 700° C. Calcining can be conducted for about 30 minutes to about 50 hours, or for about 1 hour to about 15 hours. Thus, for example, calcining can be carried out for about 1 to about 10 hours at a temperature of from about 350° C. to about 550° C. Any suitable ambient atmosphere can be employed during calcining. Generally, calcining can be conducted in an oxidizing atmosphere, such as air. Alternatively, an inert atmosphere, such as nitrogen or argon, or a reducing atmosphere, such as hydrogen or carbon monoxide, can be used.

According to one aspect of the present invention, the solid oxide material can be treated with a source of halide ion, sulfate ion, or a combination of anions, optionally treated with a metal ion, and then calcined to provide the chemically-treated solid oxide in the form of a particulate solid. For example, the solid oxide material can be treated with a source of sulfate (termed a "sulfating agent"), a source of bromide ion (termed a "bromiding agent"), a source of chloride ion (termed a "chloriding agent"), a source of fluoride ion (termed a "fluoriding agent"), or a combination thereof, and calcined to provide the solid oxide activator. Useful acidic activator-supports can include, but are not limited to, bromided alumina, chlorided alumina, fluorided alumina, sulfated alumina, bromided silica-alumina, chlorided silica-alumina, fluorided silica-alumina, sulfated silica-alumina, bromided silica-zirconia, chlorided silica-zirconia, fluorided silica-zirconia, sulfated silica-zirconia, fluorided silica-titania, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of these activator-supports optionally can be treated or impregnated with a metal ion.

The chemically-treated solid oxide can comprise a fluorided solid oxide in the form of a particulate solid. The fluorided solid oxide can be formed by contacting a solid oxide with a fluoriding agent. The fluoride ion can be added to the oxide by forming a slurry of the oxide in a suitable solvent such as alcohol or water including, but not limited to, the one to three carbon alcohols because of their volatility and low surface tension. Examples of suitable fluoriding agents can include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4PF_6$), hexafluorotitanic acid ($H_2TiF_6$), ammonium hexafluorotitanic acid (($NH_4)_2TiF_6$), hexafluorozirconic acid ($H_2ZrF_6$), $AlF_3$, $NH_4AlF_4$, analogs thereof, and combinations thereof. Triflic acid and ammonium triflate also can be employed. For example, ammonium bifluoride ($NH_4HF_2$) can be used as the fluoriding agent, due to its ease of use and availability.

If desired, the solid oxide can be treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Examples of volatile organic fluoriding agents useful in this aspect of the invention can include, but are not limited to, freons, perfluorohexane, perfluorobenzene, fluoromethane, trifluoroethanol, and the like, and combinations thereof. Calcining temperatures generally must be high enough to decompose the compound and release fluoride. Gaseous hydrogen fluoride (HF) or fluorine ($F_2$) itself also can be used with the solid oxide if fluorided while calcining Silicon tetrafluoride ($SiF_4$) and compounds containing tetrafluoroborate ($BF_4^-$) also can be employed. One convenient method of contacting the solid oxide with the fluoriding agent can be to vaporize a fluoriding agent into a gas stream used to fluidize the solid oxide during calcination.

Similarly, in another aspect of this invention, the chemically-treated solid oxide can comprise a chlorided solid oxide in the form of a particulate solid. The chlorided solid oxide can be formed by contacting a solid oxide with a chloriding agent. The chloride ion can be added to the oxide by forming a slurry of the oxide in a suitable solvent. The solid oxide can be treated with a chloriding agent during the calcining step. Any chloriding agent capable of serving as a source of chloride and thoroughly contacting the oxide during the calcining step can be used, such as $SiCl_4$, $SiMe_2Cl_2$, $TiCl_4$, $BCl_3$, and the like, including mixtures thereof. Volatile organic chloriding agents can be used. Examples of suitable volatile organic chloriding agents can include, but are not limited to, certain freons, perchlorobenzene, chloromethane, dichloromethane, chloroform, carbon tetrachloride, trichloroethanol, and the like, or any combination thereof. Gaseous hydrogen chloride or chlorine itself also can be used with the solid oxide during calcining. One convenient method of contacting the oxide with the chloriding agent can be to vaporize a chloriding agent into a gas stream used to fluidize the solid oxide during calcination.

The amount of fluoride or chloride ion present before calcining the solid oxide generally can be from about 1 to about 50% by weight, where the weight percent is based on the weight of the solid oxide, for example, silica-alumina, before calcining. According to another aspect of this invention, the amount of fluoride or chloride ion present before calcining the solid oxide can be from about 1 to about 25% by weight, and according to another aspect of this invention, from about 2 to about 20% by weight. According to yet another aspect of this invention, the amount of fluoride or chloride ion present before calcining the solid oxide can be from about 4 to about 10% by weight. Once impregnated with halide, the halided oxide can be dried by any suitable method including, but not limited to, suction filtration followed by evaporation, drying under vacuum, spray drying, and the like, although it is also possible to initiate the calcining step immediately without drying the impregnated solid oxide.

The silica-alumina used to prepare the treated silica-alumina typically can have a pore volume greater than about 0.5 cc/g. According to one aspect of the present invention, the pore volume can be greater than about 0.8 cc/g, and according to another aspect of the present invention, greater than about 1.0 cc/g. Further, the silica-alumina generally can have a surface area greater than about 100 $m^2/g$. According to another aspect of this invention, the surface area can be greater than about 250 $m^2/g$. Yet, in another aspect, the surface area can be greater than about 350 $m^2/g$.

The silica-alumina utilized in the present invention typically can have an alumina content from about 5 to about 95% by weight. According to one aspect of this invention, the alumina content of the silica-alumina can be from about 5 to about 50%, or from about 8% to about 30%, alumina by weight. In another aspect, high alumina content silica-alumina compounds can be employed, in which the alumina content of these silica-alumina compounds typically ranges from about 60% to about 90%, or from about 65% to about 80%, alumina by weight. According to yet another aspect of this invention, the solid oxide component can comprise alumina without silica, and according to another aspect of this invention, the solid oxide component can comprise silica without alumina.

The sulfated solid oxide can comprise sulfate and a solid oxide component, such as alumina or silica-alumina, in the form of a particulate solid. Optionally, the sulfated oxide can be treated further with a metal ion such that the calcined sulfated oxide comprises a metal. According to one aspect of the present invention, the sulfated solid oxide can comprise sulfate and alumina. In some instances, the sulfated alumina can be formed by a process wherein the alumina is treated with a sulfate source, for example, sulfuric acid or a sulfate salt such as ammonium sulfate. This process generally can be performed by forming a slurry of the alumina in a suitable solvent, such as alcohol or water, in which the desired concentration of the sulfating agent has been added. Suitable organic solvents can include, but are not limited to, the one to three carbon alcohols because of their volatility and low surface tension.

According to one aspect of this invention, the amount of sulfate ion present before calcining can be from about 0.5 to about 100 parts by weight sulfate ion to about 100 parts by weight solid oxide. According to another aspect of this invention, the amount of sulfate ion present before calcining can be from about 1 to about 50 parts by weight sulfate ion to about 100 parts by weight solid oxide, and according to still another aspect of this invention, from about 5 to about 30 parts by weight sulfate ion to about 100 parts by weight solid oxide. These weight ratios are based on the weight of the solid oxide before calcining. Once impregnated with sulfate, the sulfated oxide can be dried by any suitable method including, but not limited to, suction filtration followed by evaporation, drying under vacuum, spray drying, and the like, although it is also possible to initiate the calcining step immediately.

According to another aspect of the present invention, the activator-support used in preparing the catalyst compositions of this invention can comprise an ion-exchangeable activator-support including, but not limited to, silicate and aluminosilicate compounds or minerals, either with layered or non-layered structures, and combinations thereof. In another aspect of this invention, ion-exchangeable, layered aluminosilicates such as pillared clays can be used as activator-supports. When the acidic activator-support comprises an ion-exchangeable activator-support, it can optionally be treated with at least one electron-withdrawing anion such as those disclosed herein, though typically the ion-exchangeable activator-support is not treated with an electron-withdrawing anion.

According to another aspect of the present invention, the activator-support of this invention can comprise clay minerals having exchangeable cations and layers capable of expanding. Typical clay mineral activator-supports can include, but are not limited to, ion-exchangeable, layered aluminosilicates such as pillared clays. Although the term "support" is used, it is not meant to be construed as an inert component of the catalyst composition, but rather can be considered an active part of the catalyst composition, because of its intimate association with the transition metal complex component.

According to another aspect of the present invention, the clay materials of this invention can encompass materials either in their natural state or that have been treated with various ions by wetting, ion exchange, or pillaring. Typically, the clay material activator-support of this invention can comprise clays that have been ion exchanged with large cations, including polynuclear, highly charged metal complex cations. However, the clay material activator-supports of this invention also can encompass clays that have been ion exchanged with simple salts, including, but not limited to, salts of Al(III), Fe(II), Fe(III), and Zn(II) with ligands such as halide, acetate, sulfate, nitrate, or nitrite.

According to another aspect of the present invention, the activator-support can comprise a pillared clay. The term "pillared clay" is used to refer to clay materials that have been ion exchanged with large, typically polynuclear, highly charged metal complex cations. Examples of such ions can include, but are not limited to, Keggin ions which can have charges such as 7+, various polyoxometallates, and other large ions. Thus, the term pillaring can refer to a simple exchange reaction in which the exchangeable cations of a clay material are replaced with large, highly charged ions, such as Keggin ions. These polymeric cations then can be immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure can be maintained and the porosity can be enhanced. The resulting pores can vary in shape and size as a function of the pillaring material and the parent clay material used. Examples of pillaring and pillared clays are found in: T. J. Pinnavaia, Science 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. No. 4,452,910; U.S. Pat. No. 5,376,611; and U.S. Pat. No. 4,060,480; the disclosures of which are incorporated herein by reference in their entirety.

The pillaring process can utilize clay minerals having exchangeable cations and layers capable of expanding. Any pillared clay that can enhance the polymerization of olefins in the catalyst composition of the present invention can be used. Therefore, suitable clay minerals for pillaring can include, but are not limited to, allophanes; smectites, both dioctahedral (Al) and tri-octahedral (Mg) and derivatives thereof such as montmorillonites (bentonites), nontronites, hectorites, or laponites; halloysites; vermiculites; micas; fluoromicas; chlorites; mixed-layer clays; the fibrous clays including but not limited to sepiolites, attapulgites, and palygorskites; a serpentine clay; illite; laponite; saponite; and any combination thereof. In one aspect, the pillared clay activator-support can comprise bentonite or montmorillonite. The principal component of bentonite is montmorillonite.

The pillared clay can be pretreated if desired. For example, a pillared bentonite can be pretreated by drying at about 300° C. under an inert atmosphere, typically dry nitrogen, for about 3 hours, before being added to the polymerization reactor. Although an exemplary pretreatment is described herein, it should be understood that the preheating can be carried out at many other temperatures and times, including any combination of temperature and time steps, all of which are encompassed by this invention.

The activator-support used to prepare the catalyst compositions of the present invention can be combined with other inorganic support materials, including, but not limited to, zeolites, inorganic oxides, phosphated inorganic oxides, and the like. In one aspect, typical support materials that can be used include, but are not limited to, silica, silica-alumina, alumina, titania, zirconia, magnesia, boria, thoria, aluminophosphate, aluminum phosphate, silica-titania, coprecipitated silica/titania, mixtures thereof, or any combination thereof.

According to another aspect of the present invention, one or more of the transition metal complexes can be precontacted with an olefin monomer and an organoaluminum compound for a first period of time prior to contacting this mixture with the activator-support. Once the precontacted mixture of the transition metal complex(es), olefin monomer, and organoaluminum compound is contacted with the activator-support, the composition further comprising the activator-support can be termed a "postcontacted" mixture. The postcontacted mixture can be allowed to remain in further contact for a second period of time prior to being charged into the reactor in which the polymerization process will be carried out.

According to yet another aspect of the present invention, one or more of the transition metal complexes can be precontacted with an olefin monomer and an activator-support for a first period of time prior to contacting this mixture with the organoaluminum compound. Once the precontacted mixture of the transition metal complex(es), olefin monomer, and activator-support is contacted with the organoaluminum compound, the composition further comprising the organoaluminum can be termed a "postcontacted" mixture. The postcontacted mixture can be allowed to remain in further contact for a second period of time prior to being introduced into the polymerization reactor.

Co-Catalysts

In certain embodiments directed to catalyst compositions containing a co-catalyst, the co-catalyst can comprise a metal hydrocarbyl compound, examples of which include non-halide metal hydrocarbyl compounds, metal hydrocarbyl halide compounds, non-halide metal alkyl compounds, metal alkyl halide compounds, and so forth. The hydrocarbyl group (or alkyl group) can be any hydrocarbyl (or alkyl) group disclosed herein. Moreover, in some aspects, the metal of the metal hydrocarbyl can be a group 1, 2, 11, 12, 13, or 14 metal; alternatively, a group 13 or 14 metal; or alternatively, a group 13 metal. Hence, in some aspects, the metal of the metal hydrocarbyl (non-halide metal hydrocarbyl or metal hydrocarbyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some aspects, the metal hydrocarbyl or metal alkyl, with or without a halide, can comprise a lithium hydrocarbyl or alkyl, a magnesium hydrocarbyl or alkyl, a boron hydrocarbyl or alkyl, a zinc hydrocarbyl or alkyl, or an aluminum hydrocarbyl or alkyl.

In particular embodiments directed to catalyst compositions containing a co-catalyst, the co-catalyst can comprise an aluminoxane compound, an organoboron or organoborate compound, an ionizing ionic compound, an organoaluminum compound, an organozinc compound, an organomagnesium compound, or an organolithium compound, and this includes any combinations of these materials. In one aspect, the co-catalyst can comprise an organoaluminum compound. In another aspect, the co-catalyst can comprise an aluminoxane compound, an organoboron or organoborate compound, an ionizing ionic compound, an organozinc compound, an organomagnesium compound, an organolithium compound, or any combination thereof. In yet another aspect, the co-catalyst can comprise an aluminoxane compound; alternatively, an organoboron or organoborate compound; alternatively, an ionizing ionic compound; alternatively, an organozinc compound; alternatively, an organomagnesium compound; or alternatively, an organolithium compound.

Organoaluminum Compounds

In some embodiments, catalyst compositions of the present invention can comprise one or more organoaluminum compounds. Such compounds can include, but are not limited to, compounds having the formula:

where each $R^X$ independently can be an aliphatic group having from 1 to 10 carbon atoms. For example, each $R^X$ independently can be methyl, ethyl, propyl, butyl, hexyl, or isobutyl.

Other organoaluminum compounds which can be used in catalyst compositions disclosed herein can include, but are not limited to, compounds having the formula:

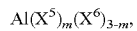

where each $X^5$ independently can be a hydrocarbyl; each $X^6$ independently can be an alkoxide or an aryloxide, a halide, or a hydride; and m can be from 1 to 3, inclusive. Hydrocarbyl is used herein to specify a hydrocarbon radical group and includes, for instance, aryl, alkyl, cycloalkyl, alkenyl, cycloalkenyl, cycloalkadienyl, alkynyl, aralkyl, aralkenyl, and aralkynyl groups.

In one aspect, each $X^5$ independently can be a hydrocarbyl having from 1 to about 18 carbon atoms. In another aspect of the present invention, each $X^5$ independently can be an alkyl having from 1 to 10 carbon atoms. For example, each $X^5$ independently can be methyl, ethyl, propyl, n-butyl, sec-butyl, isobutyl, or hexyl, and the like, in yet another aspect of the present invention.

According to one aspect of the present invention, each $X^6$ independently can be an alkoxide or an aryloxide, any one of which has from 1 to 18 carbon atoms, a halide, or a hydride. In another aspect of the present invention, each $X^6$ can be selected independently from fluorine and chlorine. Yet, in another aspect, $X^6$ can be chlorine.

In the formula, $Al(X^5)_m(X^6)_{3-m}$, m can be a number from 1 to 3, inclusive, and typically, m can be 3. The value of m is not restricted to be an integer; therefore, this formula can include sesquihalide compounds or other organoaluminum cluster compounds.

Examples of organoaluminum compounds suitable for use in accordance with the present invention can include, but are not limited to, trialkylaluminum compounds, dialkylaluminum halide compounds, dialkylaluminum alkoxide compounds, dialkylaluminum hydride compounds, and combinations thereof. Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof.

The present invention contemplates a method of precontacting a transition metal complex with an organoaluminum compound and an olefin monomer to form a precontacted mixture, prior to contacting this precontacted mixture with an activator-support to form a catalyst composition. When the catalyst composition is prepared in this manner, typically, though not necessarily, a portion of the organoaluminum compound can be added to the precontacted mixture and another portion of the organoaluminum compound can be added to the postcontacted mixture prepared when the precontacted mixture is contacted with the solid oxide activator-support. However, the entire organoaluminum compound can be used to prepare the catalyst composition in either the precontacting or postcontacting step. Alternatively, all the catalyst components can be contacted in a single step.

Further, more than one organoaluminum compound can be used in either the precontacting or the postcontacting step. When an organoaluminum compound is added in multiple steps, the amounts of organoaluminum compound disclosed herein include the total amount of organoaluminum compound used in both the precontacted and postcontacted mixtures, and any additional organoaluminum compound added to the polymerization reactor. Therefore, total amounts of organoaluminum compounds are disclosed regardless of whether a single organoaluminum compound or more than one organoaluminum compound is used.

Aluminoxane Compounds

Certain embodiments of the present invention provide a catalyst composition which can comprise an aluminoxane compound. As used herein, the term "aluminoxane" refers to aluminoxane compounds, compositions, mixtures, or discrete species, regardless of how such aluminoxanes are prepared, formed or otherwise provided. For example, a catalyst composition comprising an aluminoxane compound can be prepared in which aluminoxane is provided as the poly(hydrocarbyl aluminum oxide), or in which aluminoxane is provided as the combination of an aluminum alkyl compound and a source of active protons such as water. Aluminoxanes also can be referred to as poly(hydrocarbyl aluminum oxides) or organoaluminoxanes.

The other catalyst components typically can be contacted with the aluminoxane in a saturated hydrocarbon compound solvent, though any solvent that is substantially inert to the reactants, intermediates, and products of the activation step can be used. The catalyst composition formed in this manner can be collected by any suitable method, for example, by filtration. Alternatively, the catalyst composition can be introduced into the polymerization reactor without being isolated.

The aluminoxane compound of this invention can be an oligomeric aluminum compound comprising linear structures, cyclic structures, or cage structures, or mixtures of all three. Cyclic aluminoxane compounds having the formula:

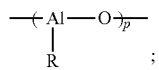

wherein each R in this formula independently can be a linear or branched alkyl having from 1 to 10 carbon atoms, and p in this formula can be an integer from 3 to 20, are encompassed by this invention. The AlRO moiety shown here also can constitute the repeating unit in a linear aluminoxane. Thus, linear aluminoxanes having the formula:

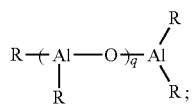

wherein each R in this formula independently can be a linear or branched alkyl having from 1 to 10 carbon atoms, and q in this formula can be an integer from 1 to 50, are also encompassed by this invention.

Further, aluminoxanes can have cage structures of the formula $R^t_{5r+\alpha}R^b_{r-\alpha}Al_{4r}O_{3r}$, wherein each $R^t$ independently can be a terminal linear or branched alkyl group having from 1 to 10 carbon atoms; each $R^b$ independently can be a bridging linear or branched alkyl group having from 1 to 10 carbon atoms; r can be 3 or 4; and $\alpha$ can be equal to $n_{Al(3)}-n_{O(2)}+n_{O(4)}$, wherein $n_{Al(3)}$ is the number of three coordinate aluminum atoms, $n_{O(2)}$ is the number of two coordinate oxygen atoms, and $n_{O(4)}$ is the number of 4 coordinate oxygen atoms.

Thus, aluminoxanes which can be employed in the catalyst compositions of the present invention can be represented generally by formulas such as $(R—Al—O)_p$, $R(R—Al—O)_qAlR_2$, and the like. In these formulas, each R group independently can be a linear or branched $C_1$-$C_6$ alkyl, such as methyl, ethyl, propyl, butyl, pentyl, or hexyl. Examples of aluminoxane compounds that can be used in accordance with the present invention can include, but are not limited to, methylaluminoxane, modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, or any combination thereof. Methylaluminoxane, ethylaluminoxane, and iso-butylaluminoxane can be prepared from trimethylaluminum, triethylaluminum, or triisobutylaluminum, respectively, and sometimes are referred to as poly(methyl aluminum oxide), poly(ethyl aluminum oxide), and poly(isobutyl aluminum oxide), respectively. It is also within the scope of the invention to use an aluminoxane in combination with a trialkylaluminum, such as that disclosed in U.S. Pat. No. 4,794,096, incorporated herein by reference in its entirety.

The present invention contemplates many values of p and q in the aluminoxane formulas $(R—Al—O)_p$ and $R(R—Al—O)_qAlR_2$, respectively. In some aspects, p and q can be at least 3. However, depending upon how the organoaluminoxane is prepared, stored, and used, the value of p and q can vary within a single sample of aluminoxane, and such combinations of organoaluminoxanes are contemplated herein.

In preparing a catalyst composition containing an aluminoxane, the molar ratio of the total moles of aluminum in the aluminoxane (or aluminoxanes) to the total moles of transition metal complex(es) in the composition generally can be between about 1:10 and about 100,000:1. In another aspect, the molar ratio can be in a range from about 5:1 to about 15,000:1. Optionally, aluminoxane can be added to a polymerization zone in ranges from about 0.01 mg/L to about 1000 mg/L, from about 0.1 mg/L to about 100 mg/L, or from about 1 mg/L to about 50 mg/L.

Organoaluminoxanes can be prepared by various procedures. Examples of organoaluminoxane preparations are disclosed in U.S. Pat. Nos. 3,242,099 and 4,808,561, the disclosures of which are incorporated herein by reference in their entirety. For example, water in an inert organic solvent can be reacted with an aluminum alkyl compound, such as $(R^X)_3Al$, to form the desired organoaluminoxane compound. While not intending to be bound by this statement, it is believed that this synthetic method can afford a mixture of both linear and cyclic R—Al—O aluminoxane species, both of which are encompassed by this invention. Alternatively, organoaluminoxanes can be prepared by reacting an aluminum alkyl compound, such as $(R^X)_3Al$, with a hydrated salt, such as hydrated copper sulfate, in an inert organic solvent.

Organoboron & Organoborate Compounds

According to another embodiment of the present invention, the catalyst composition can comprise an organoboron or organoborate compound. Such compounds can include neutral boron compounds, borate salts, and the like, or combinations thereof. For example, fluoroorgano boron compounds and fluoroorgano borate compounds are contemplated.

Any fluoroorgano boron or fluoroorgano borate compound can be utilized with the present invention. Examples of fluoroorgano borate compounds that can be used in the present invention can include, but are not limited to, fluorinated aryl borates such as N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and the like, or mixtures thereof. Examples of fluoroorgano boron compounds that can be used as co-catalysts in the present invention can include, but are not limited to, tris(pentafluorophenyl)boron, tris[3,5-bis(trifluoromethyl)-phenyl]boron, and the like, or mixtures thereof. Although not intending to be bound by the following theory, these examples of fluoroorgano borate and fluoroorgano boron compounds, and related compounds, can form "weakly-coordinating" anions when combined with a transition metal complex (see e.g., U.S. Pat. No. 5,919,983, the disclosure of which is incorporated herein by reference in its entirety). Applicants also contemplate the use of diboron, or bis-boron, compounds or other bifunctional compounds containing two or more boron atoms in the chemical structure, such as disclosed in J. Am. Chem. Soc., 2005, 127, pp. 14756-14768, the content of which is incorporated herein by reference in its entirety.

Generally, any amount of organoboron compound can be used. According to one aspect of this invention, the molar ratio of the total moles of organoboron or organoborate compound (or compounds) to the total moles of transition metal complex (or complexes) in the catalyst composition can be in a range from about 0.1:1 to about 15:1. Typically, the amount of the fluoroorgano boron or fluoroorgano borate compound used can be from about 0.5 moles to about 10 moles of boron/borate compound per mole of transition metal complex (es). According to another aspect of this invention, the amount of fluoroorgano boron or fluoroorgano borate compound can be from about 0.8 moles to about 5 moles of boron/borate compound per mole of transition metal complex (es).

Ionizing Ionic Compounds

In another embodiment, catalyst compositions disclosed herein can comprise an ionizing ionic compound. An ionizing ionic compound is an ionic compound that can function as a co-catalyst to enhance the activity of the catalyst composition. While not intending to be bound by theory, it is believed that the ionizing ionic compound can be capable of reacting with a transition metal complex and converting the transition metal complex into one or more cationic transition metal complexes, or incipient cationic transition metal complexes. Again, while not intending to be bound by theory, it is believed that the ionizing ionic compound can function as an ionizing compound by completely or partially extracting an anionic ligand, such as $X^1$ or $X^2$, from the transition metal complex. However, the ionizing ionic compound can be a co-catalyst regardless of whether it is ionizes the transition metal complex, abstracts a $X^1$ or $X^2$ ligand in a fashion as to form an ion pair, weakens the metal-$X^1$ or metal-$X^2$ bond in the transition metal complex, simply coordinates to a $X^1$ or $X^2$ ligand, or activates the transition metal complex by some other mechanism.

Further, it is not necessary that the ionizing ionic compound activate the transition metal complex only. The activation function of the ionizing ionic compound can be evident in the enhanced activity of catalyst composition as a whole, as compared to a catalyst composition that does not contain an ionizing ionic compound.

Examples of ionizing ionic compounds can include, but are not limited to, the following compounds: tri(n-butyl)ammonium tetrakis(p-tolyl)borate, tri(n-butyl)ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethylphenyl)borate, N,N-dimethylanilinium tetrakis[3,5-bis(trifluoro-methyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(tri fluoromethyl)phenyl]borate, tropylium tetrakis(pentafluorophenyl)borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethyl-phenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis(3,5-dimethylphenyl)aluminate, potassium tetrafluoroaluminate, and the like, or combinations thereof. Ionizing ionic compounds useful in this invention are not limited to these; other examples of ionizing ionic compounds are disclosed in U.S. Pat. Nos. 5,576,259 and 5,807,938, the disclosures of which are incorporated herein by reference in their entirety.

Organozinc, Organomagnesium, & Organolithium Compounds

Other embodiments are directed to catalyst compositions which can include an organozinc compound, an organomagnesium compound, an organolithium compound, or a combination thereof. In some aspects, these compounds have the following general formulas:

$$Zn(X^{10})(X^{11});$$

$$Mg(X^{12})(X^{13}); \text{ and}$$

$$Li(X^{14}).$$

In these formulas, $X^{10}$, $X^{12}$, and $X^{14}$ independently can be a $C_1$ to $C_{18}$ hydrocarbyl group, and $X^{11}$ and $X^{13}$ independently can be H, a halide, or a $C_1$ to $C_{18}$ hydrocarbyl or $C_1$ to $C_{18}$ hydrocarboxy group. It is contemplated $X^{10}$ and $X^{11}$ (or $X^{12}$ and $X^{13}$) can be the same, or that $X^{10}$ and $X^{11}$ (or $X^{12}$ and $X^{13}$) can be different.

In one aspect, $X^{10}$, $X^{11}$, $X^{12}$, $X^{13}$, and $X^{14}$ independently can be any $C_1$ to $C_{18}$ hydrocarbyl group, $C_1$ to $C_{12}$ hydrocarbyl group, $C_1$ to $C_8$ hydrocarbyl group, or $C_1$ to $C_5$ hydrocarbyl group disclosed herein. In another aspect, $X^{10}$, $X^{11}$, $X^{12}$, $X^{13}$, and $X^{14}$ independently can be any $C_1$ to $C_{18}$ alkyl group, $C_2$ to $C_{18}$ alkenyl group, $C_6$ to $C_{18}$ aryl group, or $C_7$ to $C_{18}$ aralkyl group disclosed herein; alternatively, any $C_1$ to $C_{12}$ alkyl group, $C_2$ to $C_{12}$ alkenyl group, $C_6$ to $C_{12}$ aryl group, or $C_7$ to $C_{12}$ aralkyl group disclosed herein; or alternatively, any $C_1$ to $C_5$ alkyl group, $C_2$ to $C_5$ alkenyl group, $C_6$ to $C_8$ aryl group, or $C_7$ to $C_8$ aralkyl group disclosed herein. Thus, $X^{10}$, $X^{11}$, $X^{12}$, $X^{13}$, and $X^{14}$ independently can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, an octadecenyl group, a phenyl group, a naphthyl group, a benzyl group, or a tolyl group, and the like. In yet another aspect, $X^{10}$, $X^{11}$, $X^{12}$, $X^{13}$, and $X^{14}$ independently can be methyl, ethyl, propyl, butyl, or pentyl (e.g., neopentyl), or both $X^{10}$ and $X^{11}$ (or both $X^{12}$ and $X^{13}$) can be methyl, or ethyl, or propyl, or butyl, or pentyl (e.g., neopentyl).

$X^{11}$ and $X^{13}$ independently can be H, a halide, or a $C_1$ to $C_{18}$ hydrocarbyl or $C_1$ to $C_{18}$ hydrocarboxy group (e.g., any $C_1$ to $C_{18}$, $C_1$ to $C_{12}$, $C_1$ to $C_{10}$, or $C_1$ to $C_8$ hydrocarboxy group disclosed herein). In some aspects, $X^{11}$ and $X^{13}$ independently can be H, a halide (e.g., Cl), or a $C_1$ to $C_{18}$ hydrocarbyl or $C_1$ to $C_{18}$ hydrocarboxy group; alternatively, H, a halide, or a $C_1$ to $C_8$ hydrocarbyl or $C_1$ to $C_8$ hydrocarboxy group; or alternatively, H, Br, Cl, F, I, methyl, ethyl, propyl, butyl, pentyl (e.g., neopentyl), hexyl, heptyl, octyl, nonyl, decyl, ethenyl, propenyl, butenyl, pentenyl, hexenyl, heptenyl, octenyl, nonenyl, decenyl, phenyl, benzyl, tolyl, methoxy, ethoxy, propoxy, butoxy, pentoxy, phenoxy, toloxy, xyloxy, or benzoxy.

In other aspects, the organozinc and/or the organomagnesium compound can have one or two hydrocarbylsilyl moieties. Each hydrocarbyl of the hydrocarbylsilyl group can be any hydrocarbyl group disclosed herein (e.g., a $C_1$ to $C_{18}$ alkyl group, a $C_2$ to $C_{18}$ alkenyl group, a $C_6$ to $C_{18}$ aryl group, a $C_7$ to $C_{18}$ aralkyl group, etc.). Illustrative and non-limiting examples of hydrocarbylsilyl groups can include, but are not limited to, trimethylsilyl, triethylsilyl, tripropylsilyl (e.g., triisopropylsilyl), tributylsilyl, tripentylsilyl, triphenylsilyl, allyldimethylsilyl, trimethylsilylmethyl, and the like.

Exemplary organozinc compounds which can be used as co-catalysts can include, but are not limited to, dimethylzinc, diethylzinc, dipropylzinc, dibutylzinc, dineopentylzinc, di(trimethylsilyl)zinc, di(triethylsilyl)zinc, di(triisoproplysilyl)zinc, di(triphenylsilyl)zinc, di(allyldimethylsilyl)zinc, di(trimethylsilylmethyl)zinc, and the like, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, trimethylsilylmethylmagnesium phenoxide, and the like, or any combinations thereof.

Likewise, exemplary organolithium compounds can include, but are not limited to, methyllithium, ethyllithium, propyllithium, butyllithium (e.g., t-butyllithium), neopentyllithium, trimethylsilylmethyllithium, phenyllithium, tolyllithium, xylyllithium, benzyllithium, (dimethylphenyl)methyllithium, allyllithium, and the like, or combinations thereof.

Olefin Monomers

Unsaturated reactants that can be employed with catalyst compositions and polymerization processes of this invention typically can include olefin compounds having from 2 to 30 carbon atoms per molecule and having at least one olefinic double bond. This invention encompasses homopolymerization processes using a single olefin such as ethylene or propylene, as well as copolymerization, terpolymerization, etc., reactions using an olefin monomer with at least one different olefinic compound. For example, the resultant ethylene copolymers, terpolymers, etc., generally can contain a major amount of ethylene (>50 mole percent) and a minor amount of comonomer (<50 mole percent), though this is not a requirement. Comonomers that can be copolymerized with ethylene often can have from 3 to 20 carbon atoms in their molecular chain.

Acyclic, cyclic, polycyclic, terminal ($\alpha$), internal, linear, branched, substituted, unsubstituted, functionalized, and non-functionalized olefins can be employed in this invention. For example, typical unsaturated compounds that can be polymerized with the catalyst compositions of this invention can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described above. Styrene can also be employed as a monomer in the present invention. In an aspect, the olefin monomer can comprise a $C_2$-$C_{10}$ olefin; alternatively, the olefin monomer can comprise ethylene; or alternatively, the olefin monomer can comprise propylene.

When a copolymer (or alternatively, a terpolymer) is desired, the olefin monomer can comprise, for example, ethylene or propylene, which is copolymerized with at least one comonomer. According to one aspect of this invention, the olefin monomer in the polymerization process can comprise ethylene. In this aspect, examples of suitable olefin comonomers an include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to one aspect of the present invention, the comonomer can comprise 1-butene, 1-pentene, 1-hexene, 1-octene, 1-decene, styrene, or any combination thereof; or alternatively, 1-butene, 1-hexene, 1-octene, or any combination thereof.

Generally, the amount of comonomer introduced into a reactor zone to produce a copolymer can be from about 0.01 to about 50 weight percent of the comonomer based on the total weight of the monomer and comonomer. According to another aspect of the present invention, the amount of comonomer introduced into a reactor zone can be from about 0.01 to about 40 weight percent comonomer based on the total weight of the monomer and comonomer. In still another aspect, the amount of comonomer introduced into a reactor zone can be from about 0.1 to about 35 weight percent comonomer based on the total weight of the monomer and comonomer. Yet, in another aspect, the amount of comonomer introduced into a reactor zone can be from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might. According to one aspect of the present invention, at least one monomer/reactant can be ethylene, so the polymerizations are either a homopolymerization involving only ethylene, or copolymerizations with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Catalyst Compositions

Consistent with embodiments disclosed herein are various catalyst systems and compositions. A composition in accordance with an embodiment of the invention can comprise an amine bis(phenolate) transition metal complex (e.g., an N,N-bis[2-hydroxidebenzyl]amine transition metal compound). In another embodiment, a catalyst composition can comprise a transition metal complex, an activator-support, and an optional co-catalyst. In one aspect, the present invention can encompass catalyst compositions comprising a transition metal complex, a chemically-treated solid oxide, and an organoaluminum compound, while in another aspect, the present invention can encompass catalyst compositions comprising a transition metal complex, a chemically-treated solid oxide, and a co-catalyst comprising an aluminoxane compound, an organoboron or organoborate compound, an ionizing ionic compound, an organoaluminum compound, an organozinc compound, an organomagnesium compound, or an organolithium compound, or any combination thereof. These catalyst compositions can be utilized to produce polyolefins—homopolymers, copolymers, and the like—for a variety of end-use applications.

Transition metal complexes or compounds having formulas (Ia), (Ib), (IIa), (IIb), (IIIa), and/or (IIIb) were discussed above. In aspects of the present invention, it is contemplated that the catalyst composition can contain more than one transition metal compound having formula (Ia), (Ib), (IIa), (IIb), (IIIa), and/or (IIIb) Further, additional catalytic compounds (e.g., metallocene compounds)—other than those having formulas (Ia), (Ib), (IIa), (IIb), (IIIa), and/or (IIIb)—can be employed in the catalyst composition and/or the polymerization process, provided that the additional catalytic compound(s) does not detract from the advantages disclosed herein. Additionally, more than one activator-support and/or more than one co-catalyst also can be utilized in the catalyst composition.

Generally, catalyst compositions of the present invention can comprise a transition metal complex having formula (Ia), (Ib), (IIa), (IIb), (IIIa), and/or (IIIb) and an activator-support. In aspects of the invention, the activator-support can comprise a solid oxide treated with an electron-withdrawing anion. Activator-supports useful in the present invention were disclosed above. Optionally, such catalyst compositions can further comprise one or more than one organoaluminum compound or compounds (suitable organoaluminum compounds also were discussed above). Thus, a catalyst composition of this invention can comprise a transition metal complex having formula (Ia), (Ib), (IIa), (IIb), (IIIa), and/or (IIIb), an activator-support, and an organoaluminum compound. For instance, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. Additionally, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof. Accordingly, a catalyst composition consistent with aspects of the invention can comprise (or consist essentially of, or consist of) a transition metal compound having formula (Ia), (Ib), (IIa), (IIb), (IIIa), and/or (IIIb), sulfated alumina (or fluorided silica-alumina, or fluorided silica-coated alumina), and triethylaluminum (or triisobutylaluminum).

In another aspect of the present invention, a catalyst composition is provided which comprises a transition metal complex having formula (Ia), (Ib), (IIa), (IIb), (IIIa), and/or (IIIb), an activator-support, and an organoaluminum compound, wherein this catalyst composition is substantially free of aluminoxanes, organoboron or organoborate compounds, ionizing ionic compounds, and/or other similar co-catalysts; alternatively, substantially free of aluminoxanes; alternatively, substantially free or organoboron or organoborate compounds; or alternatively, substantially free of ionizing ionic compounds. In these aspects, the catalyst composition has catalyst activity, to be discussed below, in the absence of these additional materials. For example, a catalyst composition of the present invention can consist essentially of a transition metal complex having formula (Ia), (Ib), (IIa), (IIb), (IIIa), and/or (IIIb), an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these co-catalysts can be employed. For example, a catalyst composition comprising a transition metal complex having formula (Ia), (Ib), (IIa), (IIb), (IIIa), and/or (IIIb) and an activator-support can further comprise an optional co-catalyst. Suitable co-catalysts in this aspect can include, but are not limited to, aluminoxane compounds, organoboron or organoborate compounds, ionizing ionic compounds, organoaluminum compounds, organozinc compounds, organomagnesium compounds, organolithium compounds, and the like, or any combination thereof.

In a different aspect, a catalyst composition is provided which contains a co-catalyst other than an organoaluminum compound. Such a catalyst composition can comprise a transition metal complex having formula (Ia), (Ib), (IIa), (IIb), (IIIa), and/or (IIIb), an activator-support, and a co-catalyst, wherein the co-catalyst comprises an aluminoxane compound, an organoboron or organoborate compound, an ionizing ionic compound, an organozinc compound, an organomagnesium compound, an organolithium compound, and the like, or any combination thereof.

This invention further encompasses methods of making these catalyst compositions, such as, for example, contacting the respective catalyst components in any order or sequence.

The transition metal complex having formula (Ia), (Ib), (IIa), (IIb), (IIIa), and/or (IIIb) can be precontacted with an olefinic monomer if desired, not necessarily the olefin monomer to be polymerized, and an organoaluminum compound for a first period of time prior to contacting this precontacted mixture with an activator-support. The first period of time for contact, the precontact time, between the transition metal complex, the olefinic monomer, and the organoaluminum compound typically ranges from a time period of about 1 minute to about 24 hours, for example, from about 3 minutes to about 1 hour. Precontact times from about 10 minutes to about 30 minutes also can be employed. Alternatively, the precontacting process can be carried out in multiple steps, rather than a single step, in which multiple mixtures can be prepared, each comprising a different set of catalyst components. For example, at least two catalyst components can be contacted forming a first mixture, followed by contacting the first mixture with at least one other catalyst component forming a second mixture, and so forth.

Multiple precontacting steps can be carried out in a single vessel or in multiple vessels. Further, multiple precontacting steps can be carried out in series (sequentially), in parallel, or a combination thereof. For example, a first mixture of two catalyst components can be formed in a first vessel, a second mixture comprising the first mixture plus one additional catalyst component can be formed in the first vessel or in a second vessel, which is typically placed downstream of the first vessel.

In another aspect, one or more of the catalyst components can be split and used in different precontacting treatments. For example, part of a catalyst component can be fed into a first precontacting vessel for precontacting with at least one other catalyst component, while the remainder of that same catalyst component can be fed into a second precontacting vessel for precontacting with at least one other catalyst component, or can be fed directly into the reactor, or a combination thereof. The precontacting can be carried out in any suitable equipment, such as tanks, stirred mix tanks, various static mixing devices, a flask, a vessel of any type, or combinations of these apparatus.

In another aspect of this invention, the various catalyst components (for example, a transition metal complex having formula (Ia), (Ib), (IIa), (IIb), (IIIa), and/or (IIIb), an activator-support, an organoaluminum co-catalyst, and optionally an unsaturated hydrocarbon) can be contacted in the polymerization reactor simultaneously while the polymerization reaction is proceeding. Alternatively, any two or more of these catalyst components can be precontacted in a vessel prior to entering the reaction zone. This precontacting step can be continuous, in which the precontacted product can be fed continuously to the reactor, or it can be a stepwise or batchwise process in which a batch of precontacted product can be added to make a catalyst composition. This precontacting step can be carried out over a time period that can range from a few seconds to as much as several days, or longer. In this aspect, the continuous precontacting step generally can last from about 1 second to about 1 hour. In another aspect, the continuous precontacting step can last from about 10 seconds to about 45 minutes, or from about 1 minute to about 30 minutes.

Once the precontacted mixture of the transition metal compound having formula (Ia), (Ib), (IIa), (IIb), (IIIa), and/or (IIIb), the olefin monomer, and the organoaluminum co-catalyst is contacted with the activator-support, this composition (with the addition of the activator-support) can be termed the "postcontacted mixture." The postcontacted mixture optionally can remain in contact for a second period of time, the postcontact time, prior to initiating the polymerization process. Postcontact times between the precontacted mixture and the activator-support generally range from about 1 minute to about 24 hours. In a further aspect, the postcontact time can be in a range from about 3 minutes to about 1 hour. The precontacting step, the postcontacting step, or both, can increase the productivity of the polymer as compared to the same catalyst composition that is prepared without precontacting or postcontacting. However, neither a precontacting step nor a postcontacting step is required.

The postcontacted mixture can be heated at a temperature and for a time period sufficient to allow adsorption, impregnation, or interaction of precontacted mixture and the activator-support, such that a portion of the components of the precontacted mixture can be immobilized, adsorbed, or deposited thereon. Where heating is employed, the postcontacted mixture generally can be heated to a temperature of from between about −15° C. to about 70° C., or from about 0° C. to about 40° C.

When a precontacting step is used, the molar ratio of the total moles of olefin monomer to total moles of transition metal compound(s) in the precontacted mixture typically can be in a range from about 1:10 to about 100,000:1. Total moles of each component are used in this ratio to account for aspects of this invention where more than one olefin monomer and/or more than one transition metal complex is employed in a precontacting step. Further, this molar ratio can be in a range from about 10:1 to about 1,000:1 in another aspect of the invention.

Generally, the weight ratio of organoaluminum compound to activator-support can be in a range from about 10:1 to about 1:1000. If more than one organoaluminum compound and/or more than one activator-support is employed, this ratio is based on the total weight of each respective component. In another aspect, the weight ratio of the organoaluminum compound to the activator-support can be in a range from about 3:1 to about 1:100, or from about 1:1 to about 1:50.

In some aspects of this invention, the weight ratio of transition metal compound(s) to activator-support can be in a range from about 1:1 to about 1:1,000,000. If more than one activator-support is employed, this ratio is based on the total weight of the activator-support. In another aspect, this weight ratio can be in a range from about 1:5 to about 1:100,000, or from about 1:10 to about 1:10,000. Yet, in another aspect, the weight ratio of the transition metal compound(s) to the activator-support can be in a range from about 1:20 to about 1:1000.

Catalyst compositions of the present invention generally have a catalyst activity greater than about 2,000 grams of polyethylene (homopolymer, copolymer, etc., as the context requires) per gram of transition metal compound per hour (abbreviated g/g/hr). In one aspect, the catalyst activity of the catalyst composition can be greater than about 3,000, greater than about 3,500, greater than about 4,000, greater than about 4,500, or greater than about 5,000 g/g/hr. In another aspect, catalyst compositions of this invention can be characterized by having a catalyst activity greater than about 5,500, greater than about 7,000, greater than about 10,000, or greater than about 15,000 g/g/hr. Yet, in some aspects, the catalyst activity can be in a range from about 2,000 to about 75,000, from about 4,000 to about 75,000, from about 4,000 to about 50,000, from about 5,000 to about 50,000, from about 5,000 to about 40,000, from about 7,000 to about 50,000, from about 10,000 to about 50,000, or from about 10,000 to about 40,000 g/g/hr. These activities are measured under slurry polymerization conditions using isobutane as the diluent, at a polymerization temperature of about 90° C. and a reactor pressure of about 550 psig (3.8 MPa). Generally, the reactor pressure is largely controlled by the pressure of the monomer, but other contributors to the reactor pressure can include hydrogen (if hydrogen is used), isobutane vapor, and comonomer gas or vapor (if comonomer is used). Moreover, such catalyst activities can be achieved when the catalyst composition contains a co-catalyst, such as an organoaluminum compound (e.g., triethylaluminum, triisobutylaluminum, etc.). Additionally, in some aspects, the activator-support can comprise sulfated alumina, fluorided silica-alumina, or fluorided silica-coated alumina, although not limited thereto.

As discussed above, any combination of the transition metal compound having formula (Ia), (Ib), (IIa), (IIb), (IIIa), and/or (IIIb), the activator-support, the organoaluminum compound, and the olefin monomer, can be precontacted in some aspects of this invention. When any precontacting occurs with an olefinic monomer, it is not necessary that the olefin monomer used in the precontacting step be the same as the olefin to be polymerized. Further, when a precontacting step among any combination of the catalyst components is employed for a first period of time, this precontacted mixture can be used in a subsequent postcontacting step between any other combination of catalyst components for a second period of time. For example, the transition metal compound, the organoaluminum compound, and 1-hexene can be used in a precontacting step for a first period of time, and this precontacted mixture then can be contacted with the activator-support to form a postcontacted mixture that can be contacted for a second period of time prior to initiating the polymerization reaction. For example, the first period of time for contact, the precontact time, between any combination of the transition metal compound, the olefinic monomer, the activator-support, and the organoaluminum compound can be from about 1 minute to about 24 hours, from about 3 minutes to about 1 hour, or from about 10 minutes to about 30 minutes. The postcontacted mixture optionally can be allowed to remain in contact for a second period of time, the postcontact time, prior to initiating the polymerization process. According to one aspect of this invention, postcontact times between the precontacted mixture and any remaining catalyst components can be from about 1 minute to about 24 hours, or from about 5 minutes to about 1 hour.

Polymerization Process

Catalyst compositions of the present invention can be used to polymerize olefins to form homopolymers, copolymers, terpolymers, and the like. One such process for polymerizing olefins in the presence of a catalyst composition of the present invention can comprise contacting the catalyst composition with an olefin monomer and optionally an olefin comonomer (one or more) under polymerization conditions to produce an olefin polymer, wherein the catalyst composition can comprise a transition metal compound having formula (Ia), (Ib), (IIa), (IIb), (IIIa), and/or (IIIb), an activator-support, and an optional co-catalyst. Transition metal complexes having formula (Ia), (Ib), (IIa), (IIb), (IIIa), and/or (IIIb) were discussed above.

In accordance with one aspect of the invention, the polymerization process can employ a catalyst composition comprising a transition metal compound having formula (Ia), (Ib), (IIa), (IIb), (IIIa), and/or (IIIb) and an activator-support. Activator-supports useful in the polymerization processes of the present invention were disclosed above. In another aspect, the catalyst composition can further comprise one or more than one organoaluminum compound or compounds (suitable organoaluminum compounds also were discussed above). Thus, a process for polymerizing olefins in the presence of a catalyst composition can employ a catalyst composition comprising a transition metal compound having formula (Ia), (Ib), (IIa), (IIb), (IIIa), and/or (IIIb), an activator-support, and an organoaluminum compound. In some aspects, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In some aspects, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof.

In accordance with another aspect of the invention, the polymerization process can employ a catalyst composition comprising a transition metal compound having formula (Ia), (Ib), (IIa), (IIb), (IIIa), and/or (IIIb), an activator-support, and an optional co-catalyst, wherein the co-catalyst can comprise an aluminoxane compound, an organoboron or organoborate compound, an ionizing ionic compound, an organoaluminum compound, an organozinc compound, an organomagnesium compound, or an organolithium compound, or any combination thereof. Hence, aspects of this invention are directed to a process for polymerizing olefins in the presence of a catalyst composition, the processes comprising contacting a catalyst composition with an olefin monomer and optionally an olefin comonomer (one or more) under polymerization conditions to produce an olefin polymer, and the catalyst composition can comprise a transition metal compound having formula (Ia), (Ib), (IIa), (IIb), (IIIa), and/or (IIIb), an activator-support, and an aluminoxane compound; alternatively, a transition metal compound having formula (Ia), (Ib), (IIa), (IIb), (IIIa), and/or (IIIb), an activator-support, and an organoboron or organoborate compound; alternatively, a transition metal compound having formula (Ia), (Ib), (IIa), (IIb), (IIIa), and/or (IIIb), an activator-support, and an ionizing ionic compound; alternatively, a transition metal compound having formula (Ia), (Ib), (IIa), (IIb), (IIIa), and/or (IIIb), an activator-support, and an organoaluminum compound; alternatively, a transition metal compound having formula (Ia), (Ib), (IIa), (IIb), (IIIa), and/or (IIIb), an activator-support, and an organozinc compound; alternatively, a transition metal compound having formula (Ia), (Ib), (IIa), (IIb), (IIIa), and/or (IIIb), an activator-support, and an organomagnesium compound; or alternatively, a transition metal compound having formula (Ia), (Ib), (IIa), (IIb), (IIIa), and/or (IIIb), an activator-support, and an organolithium compound. Furthermore, more than one co-catalyst can be employed, e.g., an organoaluminum compound and an aluminoxane compound, an organoaluminum compound and an ionizing ionic compound, etc.

The catalyst compositions of the present invention are intended for any olefin polymerization method using various types of polymerization reactors. As used herein, "polymerization reactor" includes any polymerization reactor capable of polymerizing olefin monomers and comonomers (one or more than one comonomer) to produce homopolymers, copolymers, terpolymers, and the like. The various types of reactors include those that can be referred to as a batch reactor, slurry reactor, gas-phase reactor, solution reactor, high pressure reactor, tubular reactor, autoclave reactor, and the like, or combinations thereof. The polymerization conditions for the various reactor types are well known to those of skill in the art. Gas phase reactors can comprise fluidized bed reactors or staged horizontal reactors. Slurry reactors can comprise vertical or horizontal loops. High pressure reactors can comprise autoclave or tubular reactors. Reactor types can include batch or continuous processes. Continuous processes could use intermittent or continuous product discharge. Processes can also include partial or full direct recycle of unreacted monomer, unreacted comonomer, and/or diluent.

Polymerization reactor systems of the present invention can comprise one type of reactor in a system or multiple reactors of the same or different type. Production of polymers in multiple reactors can include several stages in at least two separate polymerization reactors interconnected by a transfer device making it possible to transfer the polymers resulting from the first polymerization reactor into the second reactor. The desired polymerization conditions in one of the reactors can be different from the operating conditions of the other reactors. Alternatively, polymerization in multiple reactors can include the manual transfer of polymer from one reactor to subsequent reactors for continued polymerization. Multiple reactor systems can include any combination including, but not limited to, multiple loop reactors, multiple gas phase reactors, a combination of loop and gas phase reactors, multiple high pressure reactors, or a combination of high pressure with loop and/or gas phase reactors. The multiple reactors can be operated in series, in parallel, or both.

According to one aspect of the invention, the polymerization reactor system can comprise at least one loop slurry reactor comprising vertical or horizontal loops. Monomer, diluent, catalyst, and comonomer can be continuously fed to a loop reactor where polymerization occurs. Generally, continuous processes can comprise the continuous introduction of monomer/comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including but not limited to, flashing that can include any combination of heat addition and pressure reduction; separation by cyclonic action in either a cyclone or hydrocyclone; or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, and 6,833,415, each of which is incorporated herein by reference in its entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect of this invention, the polymerization reactor can comprise at least one gas phase reactor. Such systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, and 5,436,304, each of which is incorporated by reference in its entirety herein.

According to still another aspect of the invention, a high pressure polymerization reactor can comprise a tubular reactor or an autoclave reactor. Tubular reactors can have several zones where fresh monomer, initiators, or catalysts are added. Monomer can be entrained in an inert gaseous stream and introduced at one zone of the reactor. Initiators, catalysts, and/or catalyst components can be entrained in a gaseous stream and introduced at another zone of the reactor. The gas streams can be intermixed for polymerization. Heat and pressure can be employed appropriately to obtain optimal polymerization reaction conditions.

According to yet another aspect of the invention, the polymerization reactor can comprise a solution polymerization reactor wherein the monomer/comonomer are contacted with the catalyst composition by suitable stirring or other means. A carrier comprising an inert organic diluent or excess monomer can be employed. If desired, the monomer/comonomer can be brought in the vapor phase into contact with the catalytic reaction product, in the presence or absence of liquid material. The polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactors suitable for the present invention can further comprise any combination of at least one raw material feed system, at least one feed system for catalyst or catalyst components, and/or at least one polymer recovery system. Suitable reactor systems for the present invention can further comprise systems for feedstock purification, catalyst storage and preparation, extrusion, reactor cooling, polymer recovery, fractionation, recycle, storage, loadout, laboratory analysis, and process control.

Polymerization conditions that are controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature can be any temperature below the de-polymerization temperature according to the Gibbs Free energy equation. Typically, this includes from about 60° C. to about 280° C., for example, or from about 60° C. to about 120° C., depending upon the type of polymerization reactor. In some reactor systems, the polymerization temperature generally is within a range from about 70° C. to about 100° C., or from about 75° C. to about 95° C.

Suitable pressures will also vary according to the reactor and polymerization type. The pressure for liquid phase polymerizations in a loop reactor is typically less than 1000 psig (6.9 MPa). Pressure for gas phase polymerization is usually at about 200 to 500 psig (1.4 MPa to 3.4 MPa). High pressure polymerization in tubular or autoclave reactors is generally run at about 20,000 to 75,000 psig (138 to 517 MPa). Polymerization reactors can also be operated in a supercritical region occurring at generally higher temperatures and pressures. Operation above the critical point of a pressure/temperature diagram (supercritical phase) may offer advantages.

Aspects of this invention also are directed to olefin polymerization processes conducted in the absence of added hydrogen. In this disclosure, "added hydrogen" will be denoted as the feed ratio of hydrogen to olefin monomer entering the reactor (in units of ppm). An olefin polymerization process of this invention can comprise contacting a catalyst composition with an olefin monomer and optionally an olefin comonomer under polymerization conditions to produce an olefin polymer, wherein the catalyst composition can comprise a transition metal complex and an activator-support, wherein the polymerization process is conducted in the absence of added hydrogen. As disclosed above, the transition metal complex can have formula (Ia), (Ib), (IIa), (IIb), (IIIa), and/or (IIIb) As one of ordinary skill in the art would recognize, hydrogen can be generated in-situ by transition metal catalyst compositions in various olefin polymerization processes, and the amount generated can vary depending upon the specific catalyst composition and transition metal compound(s) employed, the type of polymerization process used, the polymerization reaction conditions utilized, and so forth.

In other aspects, it may be desirable to conduct the polymerization process in the presence of a certain amount of added hydrogen. Accordingly, an olefin polymerization process of this invention can comprise contacting a catalyst composition with an olefin monomer and optionally an olefin comonomer under polymerization conditions to produce an olefin polymer, wherein the catalyst composition comprises a transition metal compound and an activator, wherein the polymerization process is conducted in the presence of added hydrogen. For example, the ratio of hydrogen to the olefin monomer in the polymerization process can be controlled, often by the feed ratio of hydrogen to the olefin monomer entering the reactor. The added hydrogen to olefin monomer ratio in the process can be controlled at a weight ratio which falls within a range from about 25 ppm to about 1500 ppm, from about 50 to about 1000 ppm, or from about 100 ppm to about 750 ppm.

In some aspects of this invention, the feed or reactant ratio of hydrogen to olefin monomer can be maintained substantially constant during the polymerization run for a particular polymer grade. That is, the hydrogen:olefin monomer ratio can be selected at a particular ratio within a range from about 5 ppm up to about 1000 ppm or so, and maintained at the ratio to within about +/−25% during the polymerization run. For instance, if the target ratio is 100 ppm, then maintaining the hydrogen:olefin monomer ratio substantially constant would entail maintaining the feed ratio between about 75 ppm and about 125 ppm. Further, the addition of comonomer (or comonomers) can be, and generally is, substantially constant throughout the polymerization run for a particular polymer grade.

However, in other aspects, it is contemplated that monomer, comonomer (or comonomers), and/or hydrogen can be periodically pulsed to the reactor, for instance, in a manner similar to that employed in U.S. Pat. No. 5,739,220 and U.S. Patent Publication No. 2004/0059070, the disclosures of which are incorporated herein by reference in their entirety.

The concentration of the reactants entering the polymerization reactor can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

This invention is also directed to, and encompasses, the polymers produced by any of the polymerization processes disclosed herein. Articles of manufacture can be formed from, and/or can comprise, the polymers produced in accordance with this invention.

Polymers and Articles

If the resultant polymer produced in accordance with the present invention is, for example, a polymer or copolymer of ethylene, its properties can be characterized by various analytical techniques known and used in the polyolefin industry. Articles of manufacture can be formed from, and/or can comprise, the ethylene polymers of this invention, whose typical properties are provided below.

Polymers of ethylene (copolymers, terpolymers, etc.) produced in accordance with some aspects of this invention generally can have a melt index from 0 to about 100 g/10 min. Melt indices in the range from 0 to about 75 g/10 min, from 0 to about 50 g/10 min, or from 0 to about 30 g/10 min, are contemplated in other aspects of this invention. For example, a polymer of the present invention can have a melt index (MI) in a range from 0 to about 25, from 0 to about 10, from 0 to about 5, from 0 to about 2, or from 0 to about 1 g/10 min.

The density of ethylene-based polymers produced using one or more transition metal compounds of the present invention typically can fall within the range from about 0.88 to about 0.97 g/cc. In one aspect of this invention, the polymer density can be in a range from about 0.90 to about 0.97 g/cc. Yet, in another aspect, the density generally can be in a range from about 0.91 to about 0.96 g/cc.

Ethylene polymers, such as homopolymers, copolymers, and terpolymers, consistent with various aspects of the present invention generally can have a weight-average molecular weight ($M_w$) of greater than about 500,000 g/mol, and more often, greater than about 1,000,000 g/mol. In some aspects, the $M_w$ of the polymer is greater than about 1,500,000 g/mol, while in other aspects, the $M_w$ of the polymer is greater than about 2,000,000 g/mol. Contemplated $M_w$ ranges encompassed by the present invention can include, but are not limited to, from about 1,000,000 to about 20,000,000 g/mol, from about 1,000,000 to about 15,000,000 g/mol, from about 2,000,000 to about 10,000,000 g/mol, from about 2,000,000 to about 7,000,000 g/mol, or from about 3,000,000 to about 15,000,000 g/mol.

The ratio of $M_w/M_n$, or the polydispersity index, for the polymers of this invention often can be less than 50, less than 25, or less than 10. In some aspects disclosed herein, the ratio of $M_w/M_n$ can be less than 8, less than 5, less than 4, less than 3, or less than 2.5. Contemplated ranges for the ratio of $M_w/M_n$ can include, but are not limited to, the following ranges: from about 2 to about 50, from about 2 to about 25, from about 2 to about 10, from about 2 to about 5, from about 2 to about 4, from about 2 to about 3, or from about 2 to about 2.5, and the like.

In one aspect of this invention, the ratio of $M_z/M_w$ for polymers disclosed herein can be less than 5, less than 4 or less than 3, while in another aspect, the ratio of $M_z/M_w$ can be less than 2.5, less than 2, or less than 1.75. Contemplated ranges for the ratio of $M_z/M_w$ can include, but are not limited to, the following ranges: from about 1.5 to about 5, from about 1.5 to about 3, from about 1.5 to about 2.5, from about 1.5 to about 2, or from about 1.5 to about 1.75, and the like.

Generally, polymers produced in aspects of the present invention have low levels of long chain branching, with typically less than about 0.05 long chain branches (LCB) per 1000 total carbon atoms, but greater than zero. In some aspects, the number of LCB per 1000 total carbon atoms is less than about 0.04, less than about 0.03, less than about 0.02, or less than about 0.01. Moreover, polymers of the present invention can have less than about 0.009, less than about 0.008, less than about 0.007, less than about 0.006, or less than about 0.005 LCB per 1000 total carbon atoms, in other aspects of this invention.

Polymers of ethylene, whether homopolymers, copolymers, terpolymers, and so forth, can be formed into various articles of manufacture. Articles which can comprise polymers of this invention include, but are not limited to, an agricultural film, an armor for vehicular use or vest for personal use, an automobile part, a bottle, a drum, a fiber or fabric, a fishing line, a food packaging film or container, a food service article, a fuel tank, a geomembrane, a household container, a liner, a molded product, a medical device or material, a pipe, a rope, a sheet or tape, a toy, and the like. Various processes can be employed to form these articles. Non-limiting examples of these processes can include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Applicants also contemplate a method for forming or preparing an article of manufacture comprising a polymer produced by any of the polymerization processes disclosed herein. For instance, a method can comprise (i) contacting a catalyst composition with an olefin monomer and optionally an olefin comonomer (one or more) under polymerization conditions to produce an olefin polymer, wherein the catalyst composition can comprise a transition metal complex having formula (Ia), (Ib), (IIa), (IIb), (IIIa), and/or (IIIb), an activator-support (e.g., a chemically-treated solid oxide), and an optional co-catalyst (e.g., an organoaluminum compound); and (ii) forming an article of manufacture comprising the olefin polymer. The forming step can comprise blending, melt processing, extruding, molding, or thermoforming, and the like, including combinations thereof

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Unless otherwise noted, all operations were performed under purified nitrogen or vacuum using standard Schlenk or glovebox techniques. Et$_2$O, THF, and N,N-dimethylformamide were obtained as anhydrous from Sigma-Aldrich and used as received. Pentane, hexanes, heptanes, and toluene (obtained from Fischer Scientific) were degassed and stored over activated 13× molecular sieves under nitrogen. 1 M triisobutylaluminum (TIBA) in hexanes, 10% MAO in toluene, 2,4-di-tert-butylphenol, lithium hydroxide hydrate, paraformaldehyde, thionyl chloride, allyl amine, 3-butenylamine, and formaldehyde were obtained from Sigma-Aldrich and used as received. (B(C$_6$F$_5$)$_3$) and [Ph$_3$C][B(C$_6$F$_5$)$_4$] were obtained from Boulder Scientific Company, and ZrBn$_4$ and HfBn$_4$ were obtained from Strem Chemicals, Inc. C$_6$D$_6$ and d$_{12}$-cyclohexane (obtained from Cambridge Isotope Laboratories, Inc.) were degassed and dried over 13× molecular sieves under nitrogen. CDCl$_3$ (obtained from Cambridge Isotope Laboratories, Inc.) was used as received. 2-phenol-3, 5-di-tert-butylbenzyl alcohol, NMe$_2$, OMe, TM-3, TM-A, and TM-C were prepared according to suitable synthesis procedures. The amine bis(phenolate) transition metal compounds TM-3, TM-A, and TM-C were prepared generally as described in U.S. Pat. Nos. 6,333,423 and 6,596,827, the disclosures of which are incorporated herein by reference in their entirety. Chemical shifts (δ) for $^1$H NMR spectra are given relative to residual protium in the deuterated solvent at 7.27 and 7.16 for C$_6$D$_6$ and CDCl$_3$, respectively.

Sulfated alumina activator-supports were prepared as follows. Bohemite was obtained from W.R. Grace & Company under the designation "Alumina A" and having a surface area of about 300 m$^2$/g and a pore volume of about 1.3 mL/g. This material was obtained as a powder having an average particle size of about 100 microns. This material was impregnated to incipient wetness with an aqueous solution of ammonium sulfate to equal about 15% sulfate. This mixture was then placed in a flat pan and allowed to dry under vacuum at approximately 110° C. for about 16 hours. To calcine the resultant powdered mixture, the material was fluidized in a stream of dry air at about 550° C. for about 6 hours. Afterward, the sulfated alumina (abbreviated "AS1" in the tables that follow) was collected and stored under dry nitrogen, and was used without exposure to the atmosphere.

SEC-MALS is a combined method of size exclusion chromatography (SEC) with multi-angle light scattering (MALS). In the SEC-MALS system, a DAWN EOS photometer (Wyatt Technology, CA) was attached to a Waters 150-CV plus GPC system (Waters, MA) through a hot-transfer line controlled at 145° C. Degassed mobile phase 1,2,4-trichlorobenzene (TCB) that contained 0.5 wt % of 2,6-di-tert-butyl-4-methylphenol (BHT) was pumped through an inline filter before passing through SEC columns. Fractionated polymers first eluted through the MALS photometer where light scattering signals were recorded before passing through an IR4 detector (Polymer Char SA, Spain) where their concentrations were quantified.

The DAWN EOS system was calibrated using neat toluene at room temperature to convert the measured voltage to the intensity of scattered light. During the calibration, toluene was filtered with a 0.02 um filter (Whatman) and directly passed through the flowcell of the MALS. At room temperature, the Rayleigh ratio at the given conditions was given by 1.406×10$^{-5}$ cm$^{-1}$. A narrow polystyrene (PS) standard (American Polymer Standards) of a molecular weight of 30,000 g/mol and a concentration of 5-10 mg/mL was employed to normalize the system. At the given chromatographic conditions, radius of gyration ($R_g$) of this PS standard was estimated to be 5.6 nm using Fox-Flory equation coupled with its Mark-Houwink exponent.

At a nominal flow rate set at 0.7 mL/min (the actual flow rate was 0.6-0.7 mL/min), the mobile phase was eluted through three (3) 7.5 mm×300 mm 20 μm mixed A columns (Polymer Labs, now an Agilent Company). Polyethylene solutions with nominal concentrations of 0.5-1.5 mg/mL were prepared at 150° C. for 3-4 hr or longer, depending on the sample, before being transferred to SEC injection vials sitting in the carousel heated at 145° C. In addition to a concentration chromatogram, seventeen light scattering chromatograms at different angles were also acquired for each injection. At each chromatographic slice, the absolute molecular weight (M) was obtained from the reciprocal of the intercept of Debye plots. Refractive index increment (dn/dc) used for polyethylene in TCB at 135° C. was 0.097 mL/g. $M_n$ is the number-average molecular weight (g/mol); $M_w$ is the weight-average molecular weight (g/mol); $M_z$ is the z-average molecular weight (g/mol); and PDI is the polydispersity index, the ratio of $M_w/M_n$.

Example 1

Synthesis of 2-phenol-3,5-di-tert-butylbenzyl chloride

Approximately 20 mL of methylene chloride were added to 2-phenol-3,5-di-tert-butylbenzyl alcohol (3.55 g, 15 mmol) in a 100 mL round-bottomed flask equipped with a stirbar. Thionyl chloride (1.28 ml, 17.5 mmol) was added dropwise to the flask, yielding a yellow solution which was stirred for 30 min. While stirring, a small amount of solid formed and was filtered off. Evacuation of the volatiles produced 2-phenol-3,5-di-tert-butylbenzyl chloride as a pale yellow solid. $^1$H NMR (CDCl$_3$): δ 7.36 (d, J=3.2 Hz, 1H), δ 7.10 (d, J=3.2 Hz, 1H), δ 5.41 (s, J=1.5, 1H, OH), δ 4.73 (s, 2H), δ 1.47 (s, 9H), δ 1.34 (s, 9H).

Examples 2-6

Synthesis of N,N-Bis[2-Hydroxidebenzyl]Amine Compounds TM-1 and TM-2

A representative general synthesis scheme for compounds TM-1 and TM-2 is illustrated below:

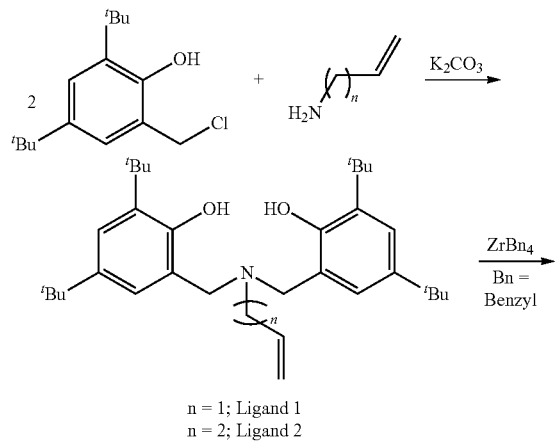

n = 1; Ligand 1
n = 2; Ligand 2

-continued

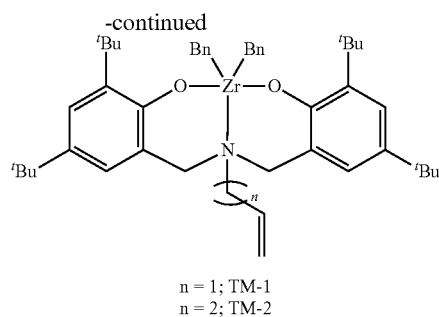

n = 1; TM-1
n = 2; TM-2

Ligand 1 was produced in Example 2. Approximately 25 mL of N,N-dimethylformamide were added to 2-phenol-3,5-di-tert-butylbenzyl chloride (1.0 g, 3.9 mmol) in a 100 mL round-bottomed flask equipped with a stirbar. Under nitrogen flow, allylamine (0.15 mL, 2 mmol) and K$_2$CO$_3$ (1.62 g, 11.8 mmol) were added to the flask, and the resulting suspension was stirred at ambient temperature for 72 hr. The reaction mixture was partitioned between 50 mL of a 1:1 NH$_4$Cl(sat):water mixture and Et$_2$O (75 mL). The organics were separated and washed with water (2×50 mL) and brine (25 mL). The volatiles were evacuated leaving a colorless residue. The colorless crystals were isolated from a saturated MeCN solution of Ligand 1 at −30° C. $^1$H NMR (CDCl$_3$): δ 7.80 (s, 2H, OH), δ 7.25 (s, 2H), δ 6.94 (s, 1H), δ 6.01 (mult, 1H), δ 5.34 (m, 2H), δ 3.72 (s, 4H), δ 3.19 (d, J=6.3 Hz, 2H), δ 1.45 (s, 18H), δ 1.32 (s, 18H).

Ligand 1 was produced via an alternative procedure in Example 3. Approximately 10 mL of MeOH were added to 2,4-di-tert-butylphenol (5 g, 24.2 mmol) in a 50 mL round-bottomed flask equipped with a stirbar. Formaldehyde (3 mL, 36 mmol) was added to the flask, then allylamine (0.91 mL, 12.1 mmol) by syringe. The resultant yellow solution was heated to reflux for 72 hr. Next, the reaction mixture was cooled to ambient temperature, then to −30° C. for several hours. The biphasic solution was decanted, and a thick oil was crystallized from a saturated MeCN solution at −30° C., resulting in Ligand 1.

Ligand 2 was produced in Example 4. Approximately 75 mL of N,N-dimethylformamide were added to 2-phenol-3,5-di-tert-butylbenzyl chloride (3 g, 3.9 mmol) and 3-butenylamine (0.633 g, 5.89 mmol) in a 200 mL round-bottomed flask equipped with a stirbar. Under nitrogen flow, K$_2$CO$_3$ (5.7 g, 41.2 mmol) was added to the flask, and the resulting suspension was stirred at ambient temperature for 72 hr. The reaction mixture was partitioned between 150 mL of a 1:1 NH$_4$Cl(sat):water mixture and Et$_2$O (150 mL). The volatiles were evacuated leaving a pale yellow residue. The pale yellow crystals were isolated from a saturated MeCN solution of Ligand 2 at −30° C. $^1$H NMR (CDCl$_3$): δ 7.69 (s, 2H, OH), δ 7.23 (d, J=2.1 Hz, 2H), δ 6.93 (d, J=2.1 Hz, 2H), δ 5.75 (mult, 1H), δ 5.14 (m, 2H), δ 3.68 (s, 4H), δ 2.66 (t, J=6.6 Hz, 2H), δ 2.42 (q, J=6.6 Hz, 2H), δ 1.44 (s, 18H), δ 1.31 (s, 18H).

Compound TM-1 was produced in Example 5. ZrBn$_4$ (0.4 g, 0.81 mmol) and Ligand 1 (0.369 g, 0.81 mmol) were dissolved in 10 mL of PhMe. The solution was heated to 65° C. for 2 hr. The volatiles were removed, leaving a colorless solid which was crystallized from a saturated pentane solution at −30° C., resulting in TM-1 and colorless crystals. $^1$H NMR (C$_6$D$_6$): δ 7.76 (d, J=8.4 Hz, 2H), δ 7.60 (d, J=2.4 Hz, 2H), δ 7.28 (t, J=7.5 Hz, 2H), δ 7.1 (t, 1H), δ 6.93 (d, J=2.1 Hz, 2H), δ 6.90 (d, J=8.4 Hz, 2H), δ 6.73 (t, J=7.2 Hz, 2H), δ 6.61 (t, J=7.2 Hz, 1H), δ 5.33 (mult, 1H), δ 4.87 (dd, J=2.1, 10.2 Hz, 2H), δ 4.65 (dd, J=1.5, 16.8 Hz, 2H), δ 3.32 (d, J=13.8 Hz, 2H), δ 2.94 (d, J=13.8 Hz, 2H), δ 2.94 (s, 2H, ZrCH$_2$Ph), δ 2.72 (d, J=7.2 Hz, 2H), δ 1.98 (s, 2H, ZrCH$_2$Ph), δ 1.83 (s, 18H), δ 1.38 (s, 18H).

Figure 3:
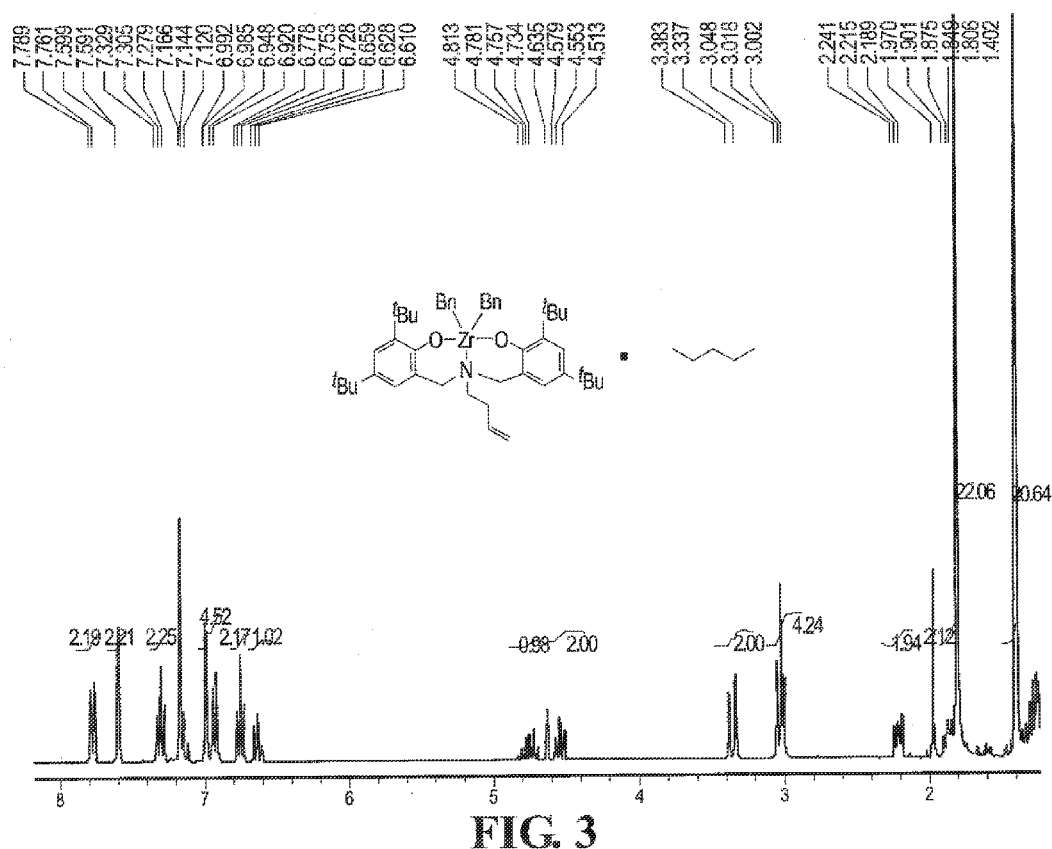
FIG. 3 presents a $^1$H-NMR plot of TM-2 from Example 6.

Compound TM-2 was produced in Example 6. ZrBn$_4$ (0.305 g, 0.6 mmol) and Ligand 2 (0.273 g, 0.6 mmol) were dissolved in 10 mL of PhMe. The solution was heated to 65° C. for 2 hr. The volatiles were removed, leaving a colorless solid which was crystallized from a saturated pentane solution at −30° C., resulting in TM-2 and colorless crystals. FIG. 3 illustrates the $^1$H-NMR analysis of TM-2. $^1$H NMR (C$_6$D$_6$): δ 7.77 (d, J=8.4 Hz, 2H), δ 7.59 (d, J=2.4 Hz, 2H), δ 7.30 (t, J=7.5 Hz, 2H), δ 7.14 (t, J=7.2 Hz, 1H), δ 6.98 (d, J=2.4 Hz, 2H), δ 6.93 (d, J=6.9 Hz, 2H), δ 6.75 (t, J=7.5 Hz, 2H), δ 6.63 (t, J=7.5 Hz, 1H), δ 4.7-4.8 (mult, 1H), δ 4.5-4.6 (mult, 2H), δ 3.36 (d, J=14.1 Hz, 2H), δ 3.02 (d, J=13.8 Hz, 2H), δ 3.01 (s, 2H, ZrCH$_2$Ph), δ 2.21 (t, J=7.8 Hz, 2H), δ 1.96 (s, 2H, ZrCH$_2$Ph), δ 1.86 (q, J=6.6 Hz, 2H), δ 1.80 (s, 18H), δ 1.40 (s, 18H).

Examples 7-8

Synthesis of Hafnium Analogs of Compounds TM-1 and TM-2

The hafnium analog of compound TM-1 was produced in Example 7. HfBn$_4$ (0.11 g, 0.203 mmol) and Ligand 1 (0.1 g, 0.203 mmol) were dissolved in 4 mL of PhMe. The solution was allowed to stand at ambient temperature overnight. The volatiles were removed, resulting in a pale yellow solid of the hafnium analog of TM-1. $^1$H NMR (C$_6$D$_6$): δ 7.70 (d, J=7.2 Hz, 2H), δ 7.66 (d, J=2.4 Hz, 2H), δ 7.20 (t, J=7.6 Hz, 2H), δ 7.05 (t, 7.6 Hz, 1H), δ 7.0 (d, 2H), δ 6.90 (d, J=2.4 Hz, 2H), δ 6.72 (t, J=7.6 Hz, 2H), δ 6.59 (t, J=7.6 Hz, 1H), δ 5.20 (mult, 1H), δ 4.82 (dd, J=1.6, 10 Hz, 2H), δ 4.64 (dd, J=1.6, 17.2 Hz, 2H), δ 3.18 (d, J=14 Hz, 2H), δ 2.85 (d, J=14 Hz, 2H), δ 2.76 (s, 2H, HfCH$_2$Ph), δ 2.47 (d, J=7.6 Hz, 2H), δ 2.24 (s, 2H, HfCH$_2$Ph), δ 1.80 (s, 18H), δ 1.35 (s, 18H).

The hafnium analog of compound TM-2 was produced in Example 8. HfBn$_4$ (0.107 g, 0.197 mmol) and Ligand 2 (0.1 g, 0.197 mmol) were dissolved in 4 mL of PhMe. The solution was allowed to stand at ambient temperature overnight. The volatiles were removed, resulting in a pale yellow gummy solid of the hafnium analog of TM-2 with impurities.

Examples 9-31

Polymerization Experiments Using N,N-Bis[2-Hydroxidebenzyl]Amine Compounds

Polymerization experiments were conducted in a one-gallon (3.875-liter) Autoclave Engineers reactor, equipped with a temperature control system and a flat stirrer operating at 900 rpm. Catalyst components were added to the reactor under a purge of isobutane while the reactor temperature was below 40° C. The reactor was then sealed, 2 L of isobutane were added, and stirring was started at 900 rpm. Reactor heating was initiated, and as the reactor temperature approached the set point, ethylene was added. Hydrogen, when used, was added with the ethylene and measured on a ppm weight basis of the ethylene feed. The set point temperature and pressure were then rapidly attained. Ethylene was fed on demand to maintain the specified reactor pressure for the specified length of the polymerization run. At the end of the run, volatiles were removed, the reactor was cooled and opened, and the polymer product was collected and dried.

Table I summarizes certain polymerization reaction conditions and catalyst activities for Examples 9-22. Reactor pressures and reaction times were 550 psig (3.79 MPa) and 1 hr, respectively. Polymerization reaction temperature was either 80° C. or 90° C. Catalyst activities were based on the grams of polymer produced per gram of transition metal compound (e.g., TM-1, TM-2, TM-3, etc.) per hour (g/g/hr).

As shown in Table I, the catalyst compositions containing TM-1, TM-2, or TM-3 and an activator-support had far superior catalyst activity to comparable catalyst systems containing either an aluminoxane or a fluorinated organoboron compound. Moreover, the catalyst compositions containing TM-1, TM-2, or TM-3 (with alkyl or alkenyl groups on the N atom) had far superior catalyst activity to comparable catalyst systems containing TM-A or TM-C (with heteroatom groups on the N atom). Of the catalyst compositions containing TM-1, TM-2, or TM-3, those with the butenyl substituent on the N atom generally had the higher catalyst activity.

Figure 4:
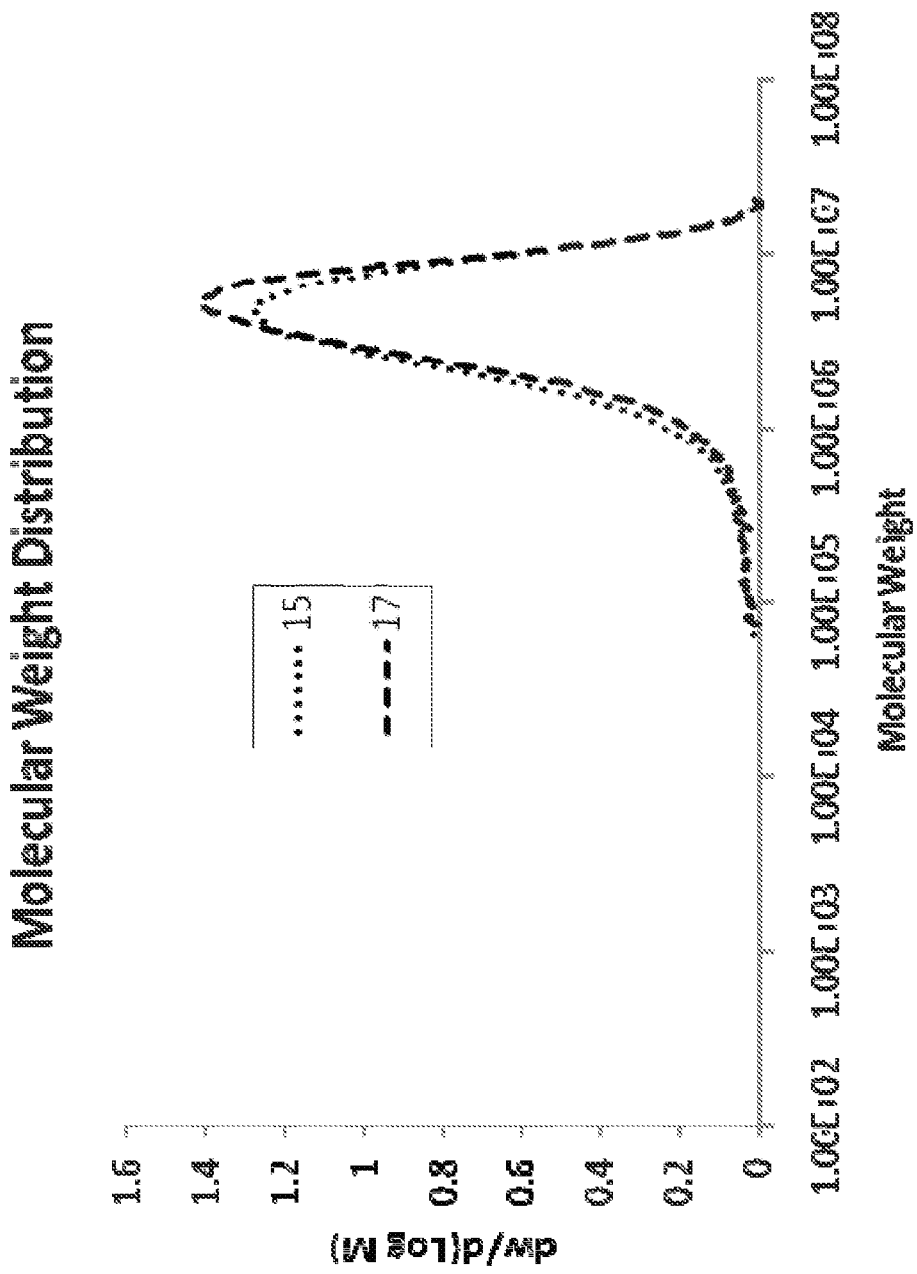
FIG. 4 presents a plot of the molecular weight distributions of the polymers of Examples 15 and 17.
Figure 5:
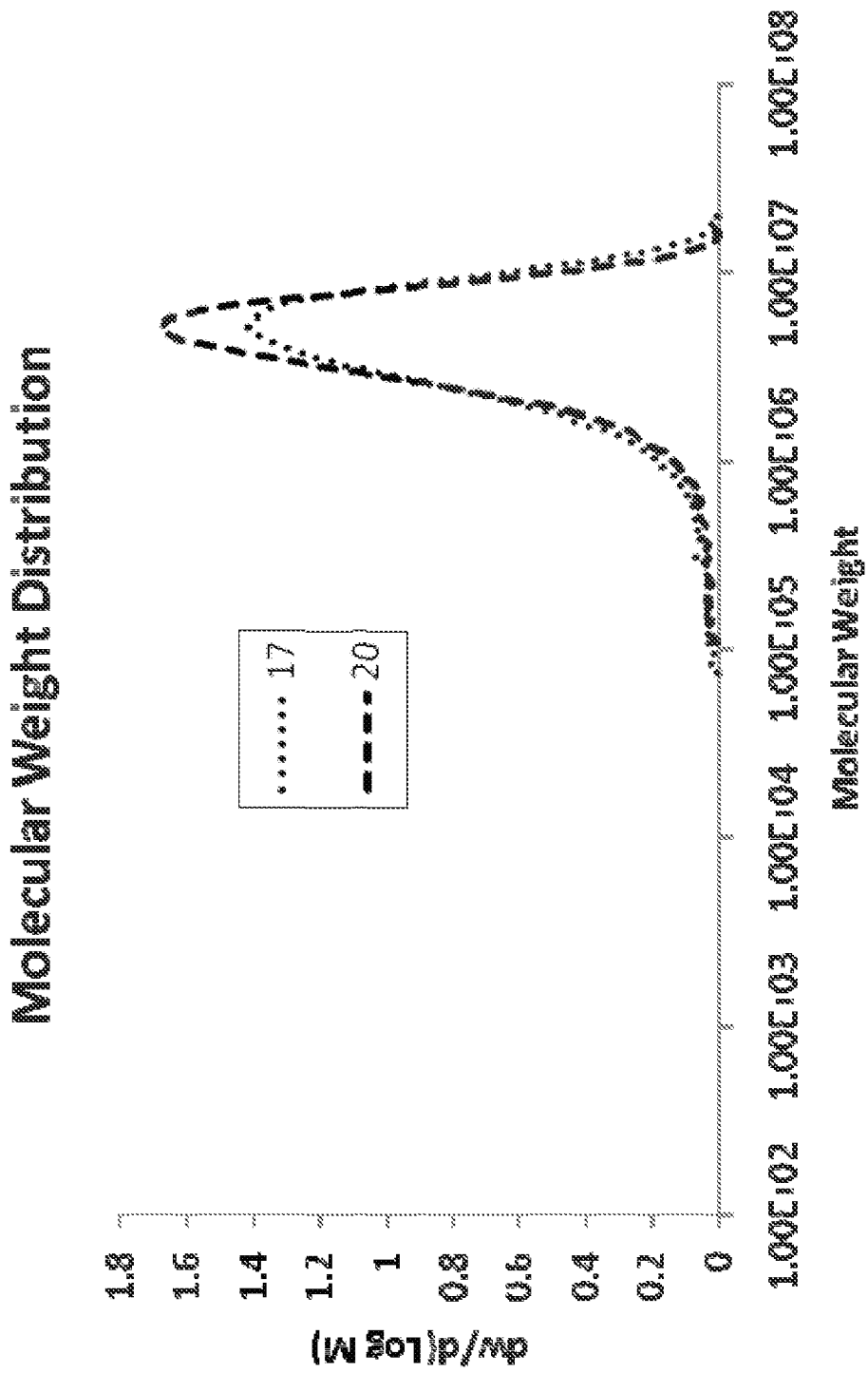
FIG. 5 presents a plot of the molecular weight distributions of the polymers of Examples 17 and 20.
Figure 6:
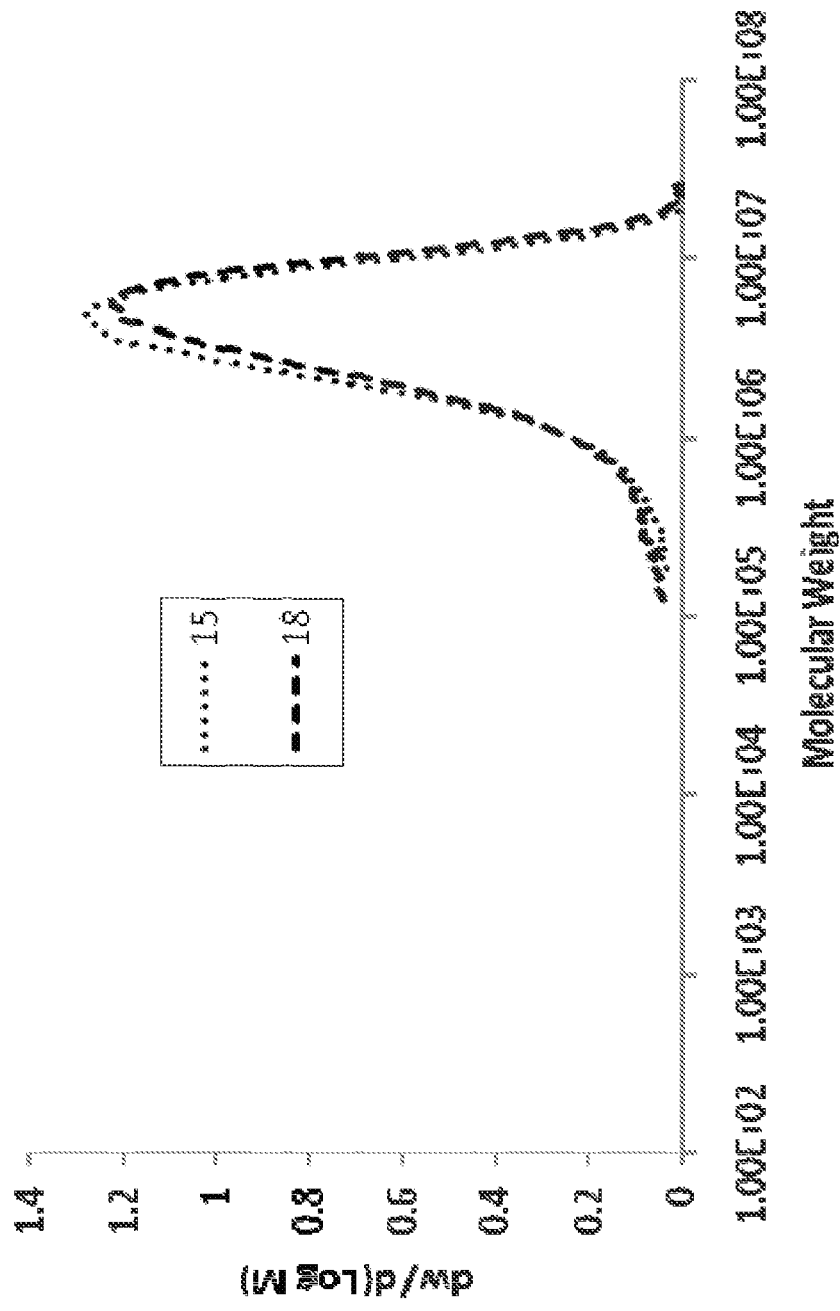
FIG. 6 presents a plot of the molecular weight distributions of the polymers of Example 15 and 18.

FIG. 4 illustrates the molecular weight distributions of the polymers of Examples 15 and 17, FIG. 5 illustrates the molecular weight distributions of the polymers of Examples 17 and 20, and FIG. 6 illustrates the molecular weight distributions of the polymers of Example 15 and 18. The molecular weight distributions for these polymers, and the M$_w$ values listed in Table IV, were determined using SEC-MALS. Unexpectedly, weight average molecular weights (M$_w$'s) were generally in excess of 3,000,000 g/mol, with narrow polydispersities.

Table II summarizes certain polymerization reaction conditions and catalyst activities for Examples 23-28, while Table III summarizes certain polymerization reaction conditions and catalyst activities for Examples 29-31. As with Table I, reactor pressures and reaction times were 550 psig (3.79 MPa) and 1 hr, respectively, and catalyst activities were based on the grams of polymer produced per gram of transition metal compound per hour (g/g/hr). Polymerization reaction temperatures were either 70° C. or 100° C. in Table II, demonstrating that the catalyst systems of Examples 23-28 maintained excellent catalyst activity at both a lower and a higher temperature than shown in Table I.

Figure 7:
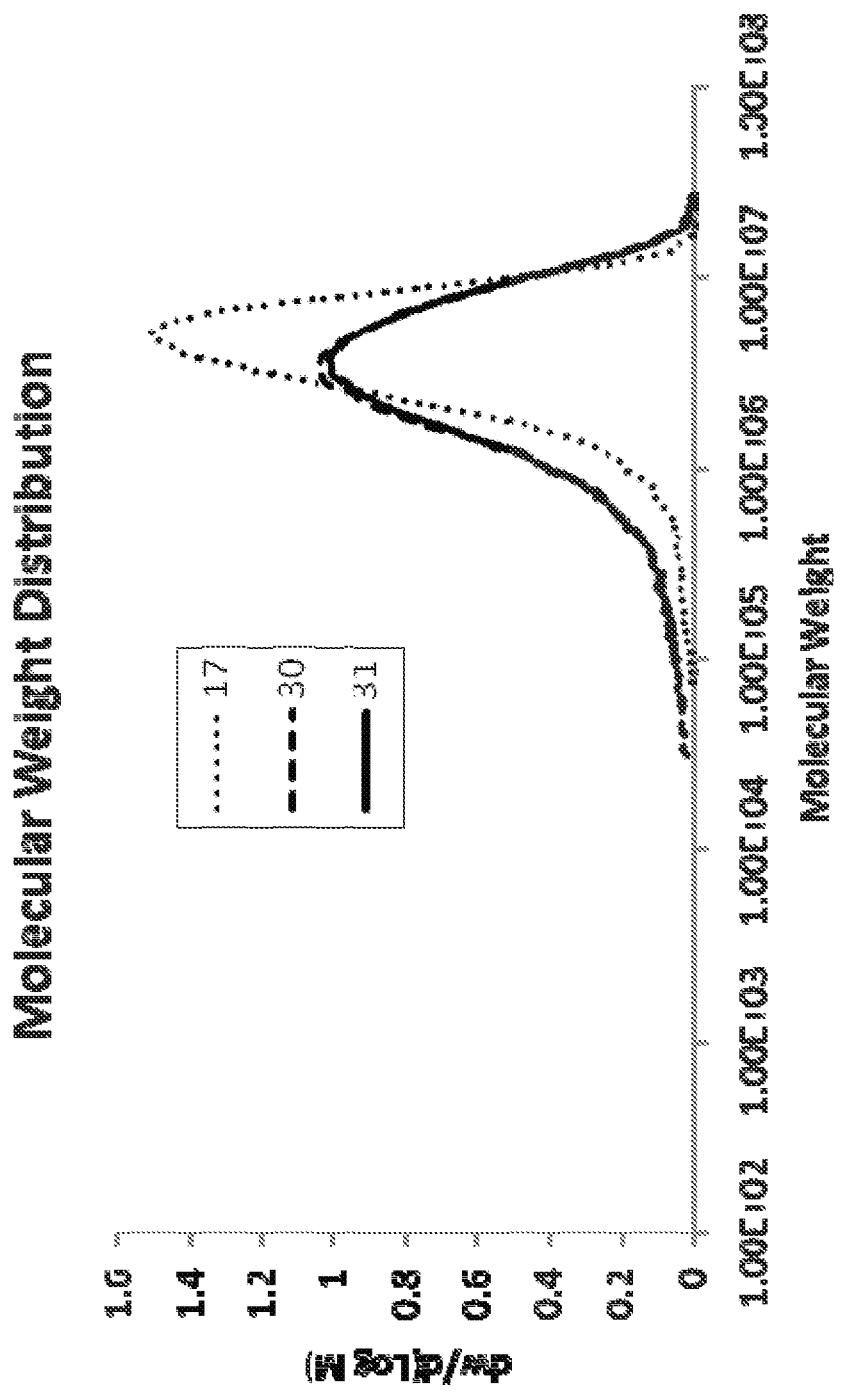
FIG. 7 presents a plot of the molecular weight distributions of the polymers of Examples 17 and 30-31.

Examples 29-31 in Table III demonstrate that the catalyst activity was largely unaffected by the addition of hydrogen on the order of 200 to 600 ppm, while the M$_w$ of the polymer produced (determined via SEC-MALS) decreased slightly due to the addition of hydrogen (see Table IV). FIG. 7 illustrates the molecular weight distributions of the polymers of Examples 30-31, as compared to that of Example 17. The addition of hydrogen resulted in broader molecular weight distributions.

TABLE I

Summary of Examples 9-22.

| Example | Catalyst Composition | Temperature (° C.) | g PE produced | Catalyst Activity (g PE/g TM compound/hr) |
|---|---|---|---|---|
| 9 | 4 mg TM-3/8 mg B(C$_6$F$_5$)$_3$ | 90 | <1 | <250 |
| 10 | 3 mg TM-3/6 mg B(C$_6$F$_5$)$_3$/0.5 mL 1M TIBA | 80 | <1 | <333 |
| 11 | 3 mg TM-3/12 mg B(C$_6$F$_5$)$_3$ | 80 | <1 | <333 |

TABLE I-continued

Summary of Examples 9-22.

| Example | Catalyst Composition | Temperature (° C.) | g PE produced | Catalyst Activity (g PE/g TM compound/hr) |
|---|---|---|---|---|
| 12 | 4 mg TM-3/1 mL 10% MAO/PhMe | 90 | 5 | 1,250 |
| 13 | 4 mg TM-1/1 mL 10% MAO/PhMe | 90 | 3 | 750 |
| 14 | 4 mg TM-2/1 mL 10% MAO/PhMe | 90 | 8 | 2,000 |
| 15 | 4 mg TM-3/0.1 g AS1/0.5 mL 1M TIBA | 90 | 87 | 21,750 |
| 16 | 4 mg TM-1/0.1 g AS1/0.5 mL 1M TIBA | 90 | 28 | 7,000 |
| 17 | 4 mg TM-2/0.1 g AS1/0.5 mL 1M TIBA | 90 | 120 | 30,000 |
| 18 | 4 mg TM-3/0.1 g AS1/0.5 mL 1M TIBA | 80 | 115 | 28,750 |
| 19 | 4 mg TM-1/0.1 g AS1/0.5 mL 1M TIBA | 80 | 31 | 7,750 |
| 20 | 4 mg TM-2/0.1 g AS1/0.5 mL 1M TIBA | 80 | 138 | 34,500 |
| 21 | 4 mg TM-A/0.1 g AS1/0.5 mL 1M TIBA | 80 | <1 | <250 |
| 22 | 4 mg TM-C/0.1 g AS1/0.5 mL 1M TIBA | 80 | 9 | 2,250 |

TABLE II

Summary of Examples 23-28.

| Example | Catalyst Composition | Temperature (° C.) | g PE produced | Catalyst Activity (g PE/g TM compound/hr) |
|---|---|---|---|---|
| 23 | 4 mg TM-3/0.1 g AS1/0.5 mL 1M TIBA | 70 | 87 | 21,750 |
| 24 | 4 mg TM-1/0.1 g AS1/0.5 mL 1M TIBA | 70 | 27 | 6,750 |
| 25 | 4 mg TM-2/0.1 g AS1/0.5 mL 1M TIBA | 70 | 114 | 28,500 |
| 26 | 4 mg TM-3/0.1 g AS1/0.5 mL 1M TIBA | 100 | 63 | 15,750 |
| 27 | 4 mg TM-1/0.1 g AS1/0.5 mL 1M TIBA | 100 | 16 | 4,000 |
| 28 | 4 mg TM-2/0.1 g AS1/0.5 mL 1M TIBA | 100 | 81 | 20,250 |

TABLE III

Summary of Examples 29-31.

| Example | Catalyst Composition | Temperature (° C.) | $H_2$ (ppm) | g PE produced | Catalyst Activity (g PE/g TM compound/hr) |
|---|---|---|---|---|---|
| 29 | Same as Example 17 | 90 | 200 | 111 | 27,750 |
| 30 | Same as Example 17 | 90 | 400 | 110 | 27,500 |
| 31 | Same as Example 17 | 90 | 600 | 103 | 25,750 |

TABLE IV

Molecular weight parameters for Examples 15, 17, 18, 20, 30, and 31.

| Example | Transition Metal Compound | Temperature (° C.) | $H_2$ (ppm) | $M_n$/1000 (g/mol) | $M_w$/1000 (g/mol) | $M_z$/1000 (g/mol) | $M_w/M_n$ | $M_z/M_w$ |
|---|---|---|---|---|---|---|---|---|
| 15 | TM-3 | 90 | 0 | 1,953 | 4,784 | 7,082 | 2.45 | 1.48 |
| 17 | TM-2 | 90 | 0 | 2,214 | 4,757 | 6,553 | 2.15 | 1.38 |
| 18 | TM-3 | 80 | 0 | 2,426 | 4,590 | 6,558 | 1.89 | 1.43 |
| 20 | TM-2 | 80 | 0 | 2,623 | 4,633 | 5,592 | 1.77 | 1.28 |
| 30 | TM-2 | 90 | 400 | 1,087 | 3,828 | 6,469 | 3.52 | 1.69 |
| 31 | TM-2 | 90 | 600 | 1,211 | 3,868 | 6,505 | 3.19 | 1.68 |

The invention claimed is:

1. An olefin polymerization process, the process comprising:
contacting a catalyst composition with an olefin monomer and optionally an olefin comonomer under polymerization conditions to produce an olefin polymer, wherein the catalyst composition comprises:
(i) an N,N-bis[2-hydroxidebenzyl]amine compound having formula (Ia):

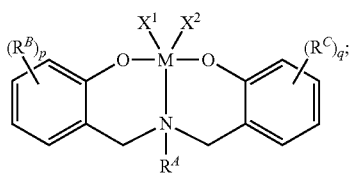

(Ia)

wherein:
M is Ti, Zr, or Hf;
$X^1$ and $X^2$ independently are a monoanionic ligand;
each $R^B$ and $R^C$ independently is a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group, wherein p and q independently are 0, 1, 2, 3, or 4; and
$R^A$ is a $C_1$ to $C_{36}$ hydrocarbyl group or $C_1$ to $C_{36}$ halogenated hydrocarbyl group;
(ii) an activator-support comprising a solid oxide treated with an electron-withdrawing anion; and
(iii) optionally, a co-catalyst.

2. The process of claim 1, wherein the process is conducted in a batch reactor, slurry reactor, gas-phase reactor, solution reactor, high pressure reactor, tubular reactor, autoclave reactor, or a combination thereof.

3. The process of claim 1, wherein the olefin monomer comprises ethylene or propylene.

4. The process of claim 1, wherein the olefin monomer comprises ethylene, and the olefin comonomer comprises 1-butene, 1-hexene, 1-octene, or a mixture thereof.

5. The process of claim 1, wherein the olefin polymer has a $M_w$ greater than about 1,000,000 g/mol.

6. The process of claim 1, wherein:
$X^1$ and $X^2$ independently are a halide or a $C_1$ to $C_{18}$ hydrocarbyl group;
each $R^B$ and $R^C$ independently is a halide, a $C_1$ to $C_{18}$ hydrocarbyl group, or a $C_1$ to $C_{18}$ hydrocarbylsilyl group, wherein p and q independently are 0, 1, or 2;
$R^A$ is a $C_1$ to $C_{18}$ hydrocarbyl group;
the activator-support comprises a fluorided solid oxide, a sulfated solid oxide, or a combination thereof; and
the olefin monomer comprises ethylene or propylene.

7. The process of claim 6, wherein:
the catalyst composition comprises a co-catalyst; and
the olefin polymer has a $M_w$ in a range from about 2,000,000 to about 7,000,000 g/mol.

8. The process of claim 6, wherein:
M is Zr or Hf;
$X^1$ and $X^2$ independently are a halide, methyl, benzyl, or phenyl;
each $R^B$ and $R^C$ independently is a $C_1$ to $C_5$ alkyl group;
the process is conducted in a slurry reactor, gas-phase reactor, solution reactor, or a combination thereof; and
the catalyst composition is contacted with ethylene and an olefin comonomer comprising 1-butene, 1-hexene, 1-octene, or a mixture thereof 9. The process of claim 8, wherein:
$R^A$ is a $C_3$ to $C_8$ terminal alkenyl group; and
the catalyst composition comprises an organoaluminum co-catalyst.

10. An olefin polymerization process, the process comprising:
contacting a catalyst composition with an olefin monomer and optionally an olefin comonomer under polymerization conditions to produce an olefin polymer, wherein the catalyst composition comprises:
(i) an N,N-bis[2-hydroxidebenzyl]amine compound having formula (Ib):

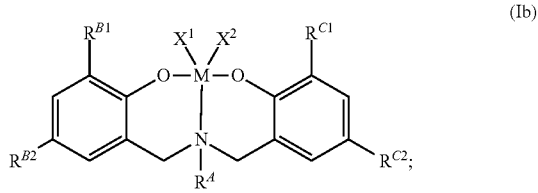

(Ib)

wherein:
M is Ti, Zr, or Hf;
$X^1$ and $X^2$ independently are a monoanionic ligand;
$R^{B1}$, $R^{B2}$, $R^{C1}$, and $R^{C2}$ independently are a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group; and
$R^A$ is a $C_1$ to $C_{36}$ hydrocarbyl group or $C_1$ to $C_{36}$ halogenated hydrocarbyl group;
(ii) an activator-support comprising a solid oxide treated with an electron-withdrawing anion; and
(iii) optionally, a co-catalyst.

11. The process of claim 10, wherein:
the process is conducted in a slurry reactor, gas-phase reactor, solution reactor, or a combination thereof; and
the catalyst composition is contacted with ethylene and an olefin comonomer comprising 1-butene, 1-hexene, 1-octene, or a mixture thereof 12. The process of claim 11, wherein:
the catalyst composition comprises a co-catalyst;
M is Zr or Hf;
$X^1$ and $X^2$ independently are a halide or a $C_1$ to $C_{18}$ hydrocarbyl group;
$R^{B1}$, $R^{B2}$, $R^{C1}$, and $R^{C2}$ independently are a halide, a $C_1$ to $C_{18}$ hydrocarbyl group, or a $C_1$ to $C_{18}$ hydrocarbylsilyl group; and
$R^A$ is a $C_1$ to $C_{18}$ hydrocarbyl group.

13. The process of claim 12, wherein the olefin polymer has a $M_w$ in a range from about 2,000,000 to about 7,000,000 g/mol.

14. The process of claim 12, wherein:
the activator-support comprises a fluorided solid oxide, a sulfated solid oxide, or a combination thereof;
the catalyst composition comprises an organoaluminum co-catalyst; and
$R^A$ is a $C_3$ to $C_8$ terminal alkenyl group.

15. The process of claim 12, wherein:
the activator-support comprises fluorided alumina, sulfated alumina, fluorided silica-alumina, sulfated silica-alumina, fluorided silica-coated alumina, sulfated silica-coated alumina, or any combination thereof; and $R^{B1}$, $R^{B2}$, $R^{C1}$, and $R^{C2}$ independently are a $C_1$ to $C_5$ alkyl group.

16. The process of claim 10, wherein:

the olefin monomer comprises ethylene or propylene; and the process is conducted in a batch reactor, slurry reactor, gas-phase reactor, solution reactor, high pressure reactor, tubular reactor, autoclave reactor, or a combination thereof.

17. The process of claim 16, wherein:

the catalyst composition comprises a co-catalyst;

M is Zr or Hf;

$X^1$ and $X^2$ independently are a halide or a $C_1$ to $C_{18}$ hydrocarbyl group;

$R^{B1}$, $R^{B2}$, $R^{C1}$, and $R^{C2}$ independently are a halide, a $C_1$ to $C_{18}$ hydrocarbyl group, or a $C_1$ to $C_{18}$ hydrocarbylsilyl group; and $R^A$ is a $C_1$ to $C_{18}$ hydrocarbyl group.

18. The process of claim 17, wherein:

the activator-support comprises a fluorided solid oxide, a sulfated solid oxide, or a combination thereof; and the olefin polymer has a $M_w$ in a range from about 2,000,000 to about 7,000,000 g/mol.

19. The process of claim 17, wherein:

$X^1$ and $X^2$ independently are a halide, methyl, benzyl, or phenyl; and $R^{B1}$, $R^{B2}$, $R^{C1}$, and $R^{C2}$ independently are a $C_1$ to $C_5$ alkyl group.

20. The process of claim 19, wherein:

$R^A$ is a $C_3$ to $C_8$ terminal alkenyl group;

the activator-support comprises a fluorided solid oxide, a sulfated solid oxide, or a combination thereof;

the catalyst composition comprises an organoaluminum co-catalyst; and the catalyst composition is contacted with ethylene and a comonomer comprising 1-butene, 1-hexene, 1-octene, or a mixture thereof.

* * * * *